US012807948B2

(12) United States Patent
Carninci et al.

(10) Patent No.: US 12,807,948 B2
(45) Date of Patent: Nov. 24, 2026

(54) MODIFIED FUNCTIONAL NUCLEIC ACID MOLECULES

(71) Applicant: FONDAZIONE ISTITUTO ITALIANO DI TECNOLOGIA, Genoa (IT)

(72) Inventors: Piero Carninci, Royston (GB); Hazuki Takahashi, Royston (GB); Naoko Toki, Royston (GB); Stefano Gustincich, Genoa (IT); Bianca Pierattini, Genoa (IT); Paola Valentini, Genoa (IT)

(73) Assignee: Fondazione Istituto Italiano Di Technologia, Genoa (IT)

( * ) Notice: Subject to any disclaimer, the term of this patent is extended or adjusted under 35 U.S.C. 154(b) by 651 days.

(21) Appl. No.: 18/245,902

(22) PCT Filed: Sep. 24, 2021

(86) PCT No.: PCT/GB2021/052502
§ 371 (c)(1),
(2) Date: Mar. 20, 2023

(87) PCT Pub. No.: WO2022/064221
PCT Pub. Date: Mar. 31, 2022

(65) Prior Publication Data

US 2023/0383293 A1 Nov. 30, 2023

(30) Foreign Application Priority Data

Sep. 24, 2020 (EP) .................................... 20425038

(51) Int. Cl.
*C12N 15/113* (2010.01)

(52) U.S. Cl.
CPC ........ *C12N 15/113* (2013.01); *C12N 2310/11* (2013.01); *C12N 2310/321* (2013.01); *C12N 2310/333* (2013.01)

(58) Field of Classification Search
None
See application file for complete search history.

(56) References Cited

U.S. PATENT DOCUMENTS

2018/0291400 A1* 10/2018 Zhang ...................... C12N 5/10

FOREIGN PATENT DOCUMENTS

WO 2012/133947 A1 10/2012
WO WO-2019058304 A1 * 3/2019 ............ C12N 15/67
WO 2019/150346 A1 8/2019

OTHER PUBLICATIONS

Podbevsek et al. Scientific Reports. 2018. 8:3189. (Year: 2018).*
Wesselhoeft et al. Nature Communications. 2018. 9:2629. (Year: 2018).*

(Continued)

*Primary Examiner* — Joseph G. Dauner
(74) *Attorney, Agent, or Firm* — Lathrop GPM LLP; Malaika Tyson

(57) ABSTRACT

The invention relates to functional nucleic acid molecules comprising a target determinant sequence and a regulatory sequence wherein the functional nucleic acid molecule comprises one or more chemical modifications, particularly for use in methods of increasing target protein synthesis efficiency.

1 Claim, 24 Drawing Sheets

Specification includes a Sequence Listing.

(56) References Cited

OTHER PUBLICATIONS

International Preliminary Report on Patentability from PCT/GB2021/052502, mailed Apr. 6, 2023, 7 pages.
International Search Report from PCT/GB2021 /052502, mailed Jan. 20, 2022, 6 pages.
Written Opinion from PCT/GB2021 /052502, mailed Jan. 20, 2022, 5 pages.
Bartosik et al. (2020) "Synthesis of Nucleobase-Modified RNA Oligonucleotides by Post-Synthetic Approach" Molecules, vol. 25, No. 15, Article 3344. (37 pages).
Bedell et al. (2000) "MaskerAid: a performance enhancement to RepeatMasker" BioInformatics, vol. 16, No. 11, pp. 1040-1041.
Boiziau et al. (1995) "Antisense 2'-O-alkyl oligoribonucleotides are efficient inhibitors of reverse transcription" Nucleic Acids Research, vol. 23, No. 1, pp. 64-71.
Carrieri et al. (2012) "Long non-coding antisense RNA controls Uchl1 translation through an embedded SINEB2 repeat" Nature, vol. 491, No. 7424, pp. 454-457.
Castellanos-Rubio et al. (2019) "A novel RT-QPCR-based assay for the relative quantification of residue specific m6A RNA methylation" Sci Rep, vol. 9, No. 1, Article 4220. (7 pages).
Indrieri et al. (2016) "Synthetic long non-coding RNAs [SINEUPs] rescue defective gene expression in vivo" Sci Rep, vol. 6, No. 1, Article 27315 (8 pages).
Kierzek et al. (2014) "The contribution of pseudouridine to stabilities and structure of RNAs" Nucleic Acids Research vol. 42, No. 5, pp. 3492-3501.
Kypr et al. (2009) "Circular dichroism and conformational polymorphism of DNA" Nucleic Acids Research, vol. 37, No. 6, pp. 1713-1725.
Kypr et al. (2012) "Circular Dichroism Spectroscopy of Nucleic Acids" at pp. 575-586 in Comprehensive Chiroptical Spectroscopy, vol. 2, Editors Berova et al., John Wiley & Sons, Hoboken, New Jersey USA.
Leger et al. (2019) "RNA modifications detection by comparative Nanopore direct RNA sequencing" bioRxiv, Article 10.110/843136. (29 pages).
Leger et al. (2021) "RNA modifications detection by comparative Nanopore direct RNA sequencing" Nat Commun, vol. 12, No. 1, Article 7198. (17 pages).
Mandal et al. (2013) "Reprogramming human fibroblasts to pluripotency using modified mRNA" Nat Protoc., vol. 8, No. 3, pp. 568-582.
Nowakowski et al. (1997) "RNA Structure and Stability" Seminars in Virology, vol. 8, No. 3, pp. 153-165.
Ranjbar et al. (2009) "Circular Dichroism Techniques: Biomolecular and Nanostructural Analyses—A Review" Chem Biol Drug Des, vol. 74, No. 2, pp. 101-120.
Schein et al. (2016) "Identification of antisense long noncoding RNAs that function as SINEUPs in human cells" Sci Rep, vol. 6, Article 33605. (8 pages).
Sekine et al. (2011) "Synthesis and hybridization properties of 2'-O-methylated oligoribonucleotides incorporating 2'-O-naphthyluridines" Org Biomol Chem, vol. 9, No. 1, pp. 210-218.
Sosnick (2001) "Characterization of tertiary folding of RNA by circular dichroism and urea" Curr Protoc Nucleic Acid Chem, Chapter 11, Unit 11.5.
Sumita et al. (2005) "Effects of nucleotide substitution and modification on the stability and structure of helix 69 from 28S rRNA" RNA, vol. 11, No. 9, pp. 1420-1429.
Szabat et al. (2015) "Structural Aspects of the Antiparallel and Parallel Duplexes Formed by DNA, 2'-O-Methyl RNA and RNA Oligonucleotides" PloS One, vol. 10, No. 11, Article 0143354. (16 pages).
Takahashi et al. (2018) "Identification of functional features of synthetic SINEUPs, antisense IncRNAs that specifically enhance protein translation" PloS One, vol. 13, No. 2, Article 0183229. (17 pages).
Toki et al. (2019) "SINEUP long non-coding RNA acts via PTBP1 and HNRNPK to promote translational initiation assemblies" bioRxiv, Article 10.1101/664029. (39 pages).
Toki et al. (2020) "SINEUP long non-coding RNA acts via PTBP1 and HNRNPK to promote translational initiation assemblies" Nucleic Acids Res, vol. 48, No. 20, pp. 11626-11644.
Toki et al. (2020) "Synthetic in vitro transcribed IncRNAs (SINEUPs) with chemical modifications enhance target mRNA translation" FEBS Lett, vol. 594, pp. 4357-4369.
Werner et al. (1998) "Investigations on the influence of 2'-O-alkyl modifications on the base pairing properties of oligonucleotides" Pharmaceutica Acta Helvetiae, vol. 73, No. 1, pp. 3-10.
Zucchelli et al. (2015) "SINEUPs are modular antisense long non-coding RNAs that increase synthesis of target proteins in cells" Front Cell Neurosci, vol. 9, Article 174. (12 pages).
Zucchelli et al. (2015) "SINEUPs: A new class of natural and synthetic antisense long non-coding RNAs that activate translation" RNA Biology, vol. 12, No. 8, pp. 771-779.
Zucchelli et al. (2016) "Engineering Translation in Mammalian Cell Factories to Increase Protein Yield: The Unexpected Use of Long Non-Coding SINEUP RNAs" Comput Struct Biotechnol J, vol. 14, pp. 404-410.

* cited by examiner (A)

(B)

miniSINEUP-SOX9

CTCGAGTCATACGCGAGCCCGGGGCAGGGGGCGGGTGGCCGGATGCGGCCGCCACTGTGCTGGA
ATTCCAGTGCTAGAGGAGGTCAGAAGAGGGCATTGGATCCCCCAGAACTGGAGTTATACGGTAACC
TCGTGGTGGTTGTGAACCACCATGTGGATGGATATTGAGTTCCAAACACTGGTCCTGTGCAAGAGC
ATCCAGTGCTCTTAAGTGCTGAGCCATCTCTTTAGCTCCAGTCTCTTAAGCTTTCTAGA (D)

(E)

Thermal stability

| SINEUP | Tm (°C) |
|---|---|
| unmodified | 68.1 ± 0.2 |
| m6A | 73.6 ± 0.5 |
| ψ | 81.1 ± 0.5 |
| m6A + ψ | 81.5 ± 0.3 |
| Am | 85.6 ± 0.4 |
| Am + m6A | 67.2 ± 0.2 |

(F)

(G)

MODIFIED FUNCTIONAL NUCLEIC ACID MOLECULES

CROSS-REFERENCE TO RELATED APPLICATIONS

The present application is a 35 U.S.C. § 371 National Stage patent application of International patent application PCT/GB2021/052502, filed on Sep. 24, 2021, which claims priority to EP patent application No. 20425038.5, filed on Sep. 24, 2020.

SEQUENCE LISTING

The instant application contains a Sequence Listing which has been electronically submitted via and is hereby incorporated by reference in its entirety. Said.txt file, created on Jun. 8, 2026, is named 765316_STT-032_sequence listing.txt and is 19,146 bytes in size.

FIELD OF THE INVENTION

The present invention relates to functional nucleic acid molecules, particularly functional RNA molecules, for use in upregulating target mRNA expression.

BACKGROUND OF THE INVENTION

With the development of genomics technologies, it became widely recognized that an emerging class of long non-coding RNAs (IncRNAs), which constitute the majority of types of transcripts and do not encode proteins, play key regulatory roles in the physiology of normal cells, as well as in the development of diseases including cancer and neurodegenerative diseases.

The discovery of increasing numbers of functional IncRNAs has prompted novel therapeutic applications, including the treatment of human genetic diseases. A new class of long non-coding RNAs (IncRNAs), known as SINEUPs, were previously described to be able to selectively enhance their targets' translation. SINEUP activity relies on the combination of two domains: the overlapping region, or binding domain (BD), that confers specificity, and an embedded inverted SINE B2 element, or effector domain (ED), enhancing target mRNA translation. WO 2012/133947 and WO 2019/150346 disclose functional nucleic acid molecules including SINEUPs. Another class of IncRNAs that use effector domains comprising an internal ribosome entry site (IRES) sequence to provide trans-acting functional nucleic acid molecules are described in WO 2019/058304.

In previous studies, plasmid transfection has been used to deliver the SINEUP technology, however this requires export of RNA transcribed in the nuclei for co-localisation with target mRNAs in the cytoplasm. Therefore, it is desirable to provide functional IncRNAs which are suitable for direct transfection into the cytoplasm.

SUMMARY OF THE INVENTION

According to a first aspect of the invention, there is provided a functional nucleic acid molecule comprising:

(a) at least one target determinant sequence comprising a sequence reverse complementary to a target mRNA sequence for which protein translation is to be enhanced; and (b) at least one regulatory sequence comprising a SINE B2 element or a functionally active fragment of a SINE B2 element, wherein the functional nucleic acid molecule comprises one or more chemical modifications.

According to a further aspect of the invention, there is provided a composition comprising the functional nucleic acid molecule described herein.

According to a further aspect of the invention, there is provided a method for increasing the protein synthesis efficiency of a target in a cell comprising administering the functional nucleic acid molecule or the composition described herein, to the cell.

Translational up-regulation of SOX9 protein by transfection of miniSINEUP-SOX9 or miniSINEUP-Random (Rd), which contains a random sequence instead of the miniSINEUP-SOX9 BD. Western blot image shows representative images of the effect of SINEUPs on the SOX9 protein level. Quantification of SOX9 levels compared with non-transfected cells (Cont.) shown as means+SD of at least 3 independent experiments. ** $p<0.01$; * $p<0.05$; ns: not significant (two-tailed Student's t-test). (C) Quantification of the SOX9 mRNA and miniSINEUP RNA levels following transfection with SINEUP plasmid. ns: not significant (two-tailed Student's t-test). Data are shown as means+S.D. from at least 3 independent experiments.

Figure 5:
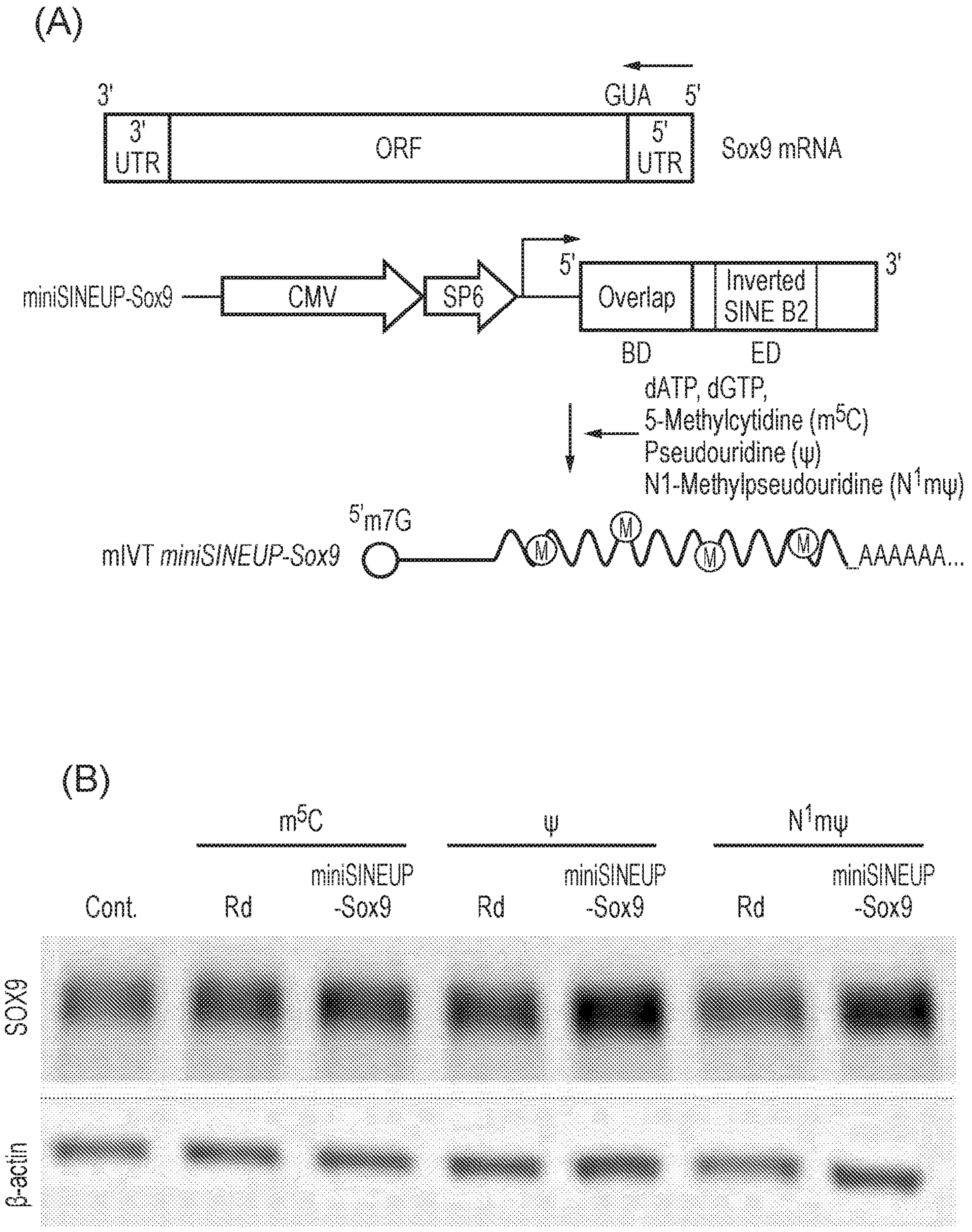
Figure 5:
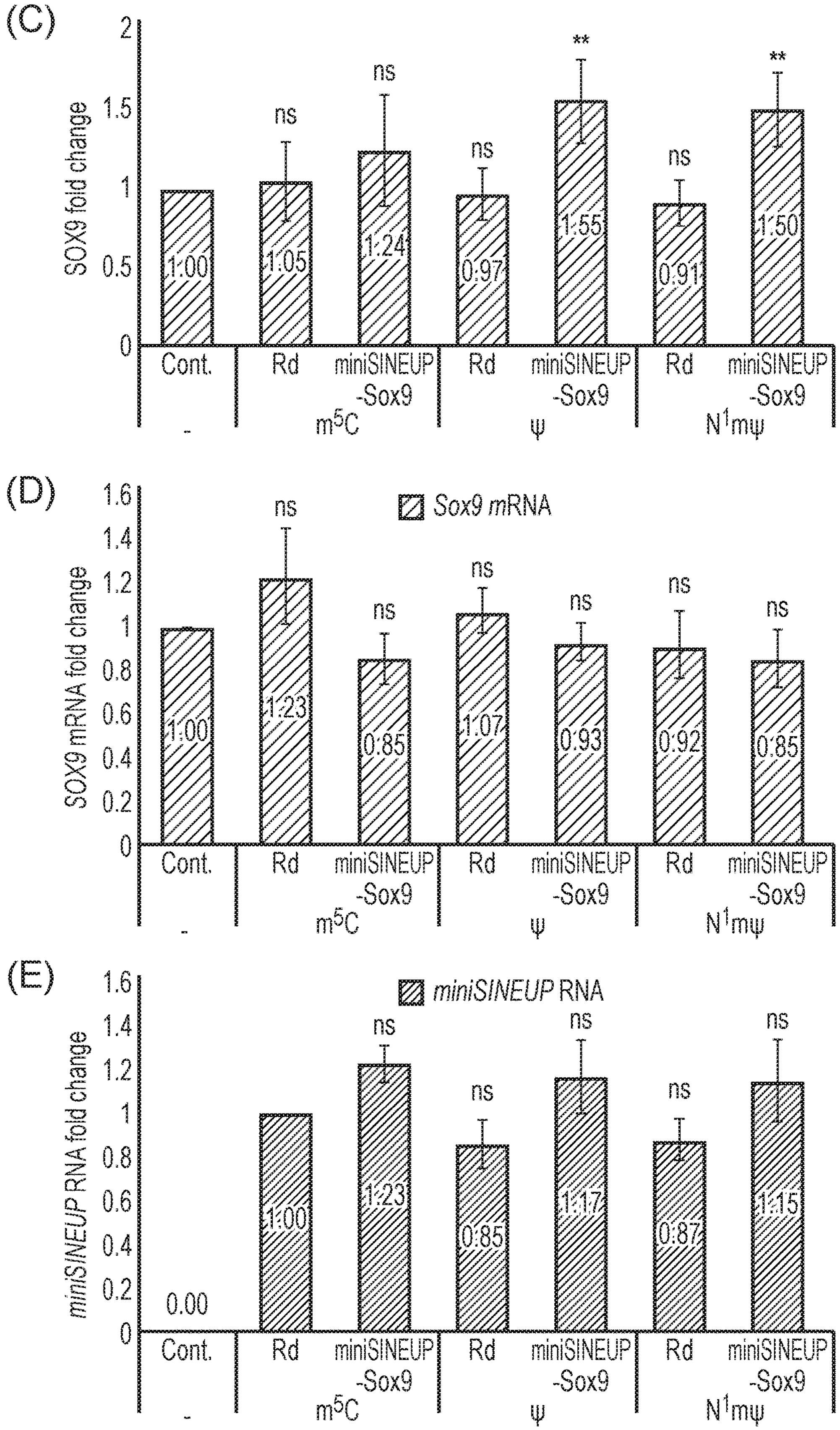

FIG. 5: Transfection of modified IVT miniSINEUP-SOX9 in HepG2 cells. (A) Diagram of nucleotide modifications in the miniSINEUP-SOX9 constructs with 5-Methylcytidine-5'-Tri phosphate (m5C), Pseudouridine-5'-Tri phosphate (ψ) or N1-Methylpseudouridine-5'-Triphosphate (N1mψ). MiniSINEUP-SOX9 contains the overlapping region with SOX9 mRNA as a binding domain (BD) and SINEB2 element as an effector domain (ED). (B-C) Translational up-regulation of SOX9 by transfection of modified in vitro transcribed (mIVT) SINEUP RNAs. Western blot image shows representative images of the effect of mIVT SINEUPs on the SOX9 protein level. Quantification of SOX9 levels compared with non-transfected cells (Cont.) shown as means±S.D. of at least 3 independent experiments. ** $p<0.01$; * $p<0.05$; ns: not significant (two-tailed Student's t-test). (D-E) Quantification of the SOX9 mRNA and the miniSINEUP RNA levels following transfection with mIVT SINEUPs. ns: not significant (two-tailed Student's t-test). Data are shown as means±S.D. from at least 3 independent experiments.

Figure 6:
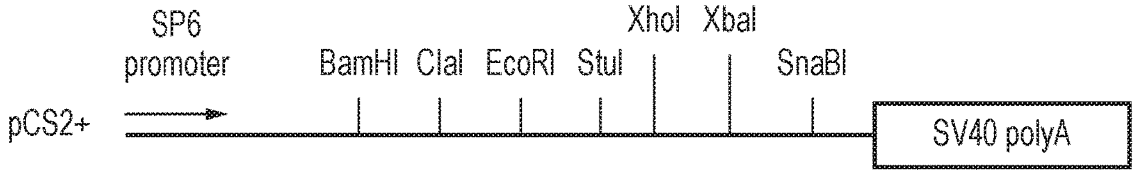
Figure 6:
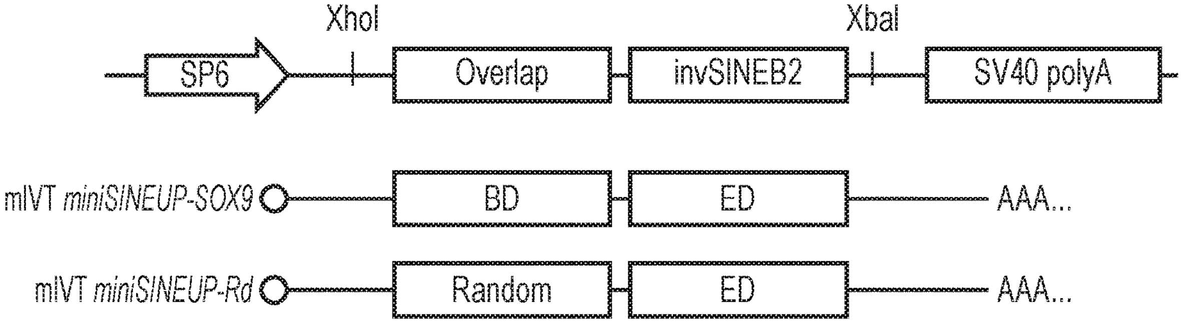

FIG. 6: (A) Schematic diagram of the multicloning region in pCS2+. (B) miniSINEUP-SOX9 construct (SEQ ID NO: 54). The SINEUP targeting mouse SOX9 consists of a binding domain (BD) that overlaps the SOX9 mRNA sequence and an effector domain (ED) containing an inverted SINEB2 sequence from mouse AS-Uchl1 RNA. The SINEUP was cloned into the XhoI and XbaI sites of pCS2+ (A). Underlining highlights BD of SOX9 mRNA; ED is italicized, and restriction sites are at each end of the sequence (XhoI, CTCGAG; XbaI, TCTAGA).

Figure 7:
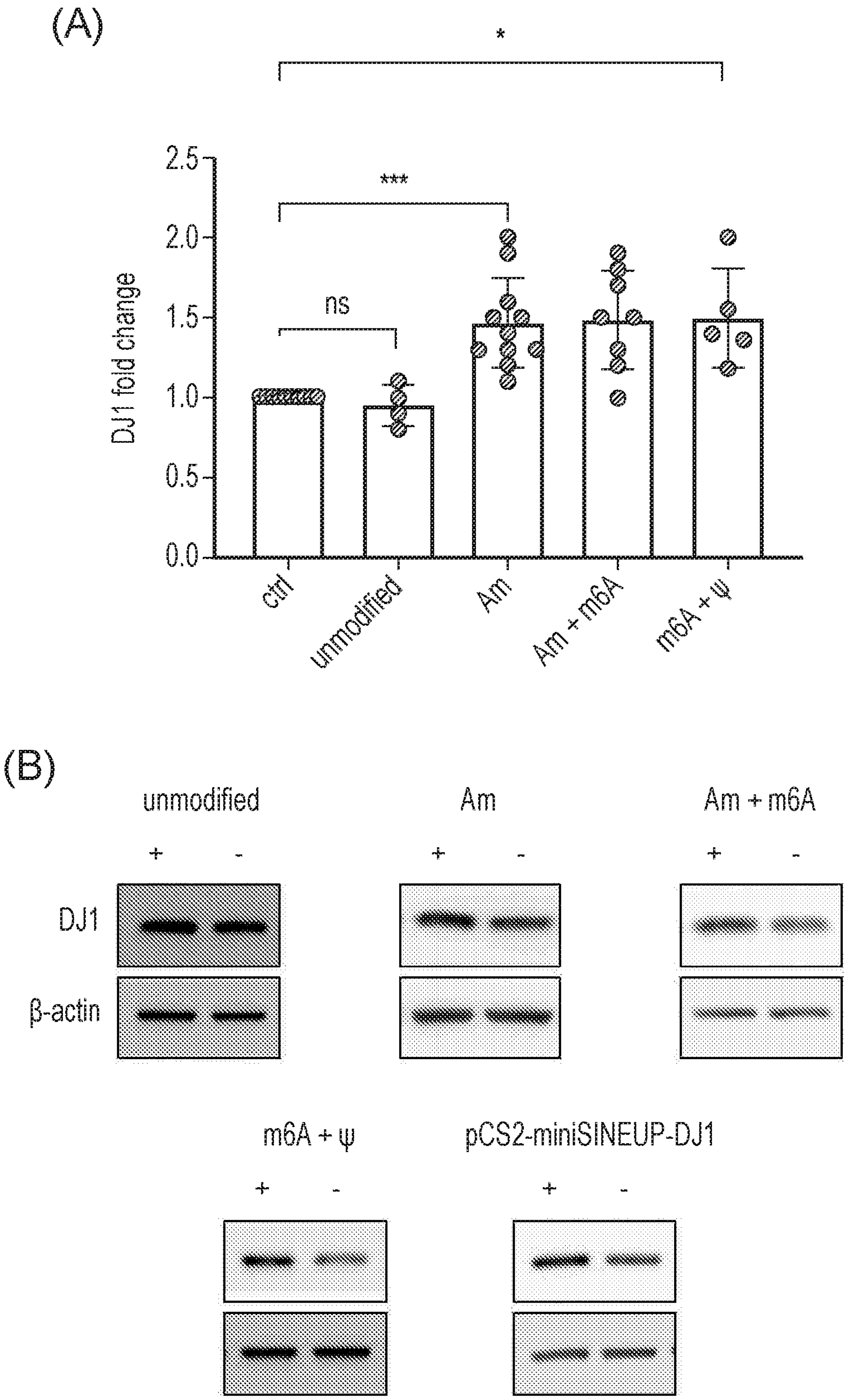

FIG. 7: SINEUP effect is restored in modified IVT RNA. Different combinations of modifications are suitable to preserve the functionality of miniSINEUP DJ1. (A) DJ1 fold change from Western blot quantification of at least 3 different experiments. (B) Representative Western blot images of cells transfected with miniSINEUP RNA carrying different modifications or with control miniSINEUP plasmid.

Figure 8:
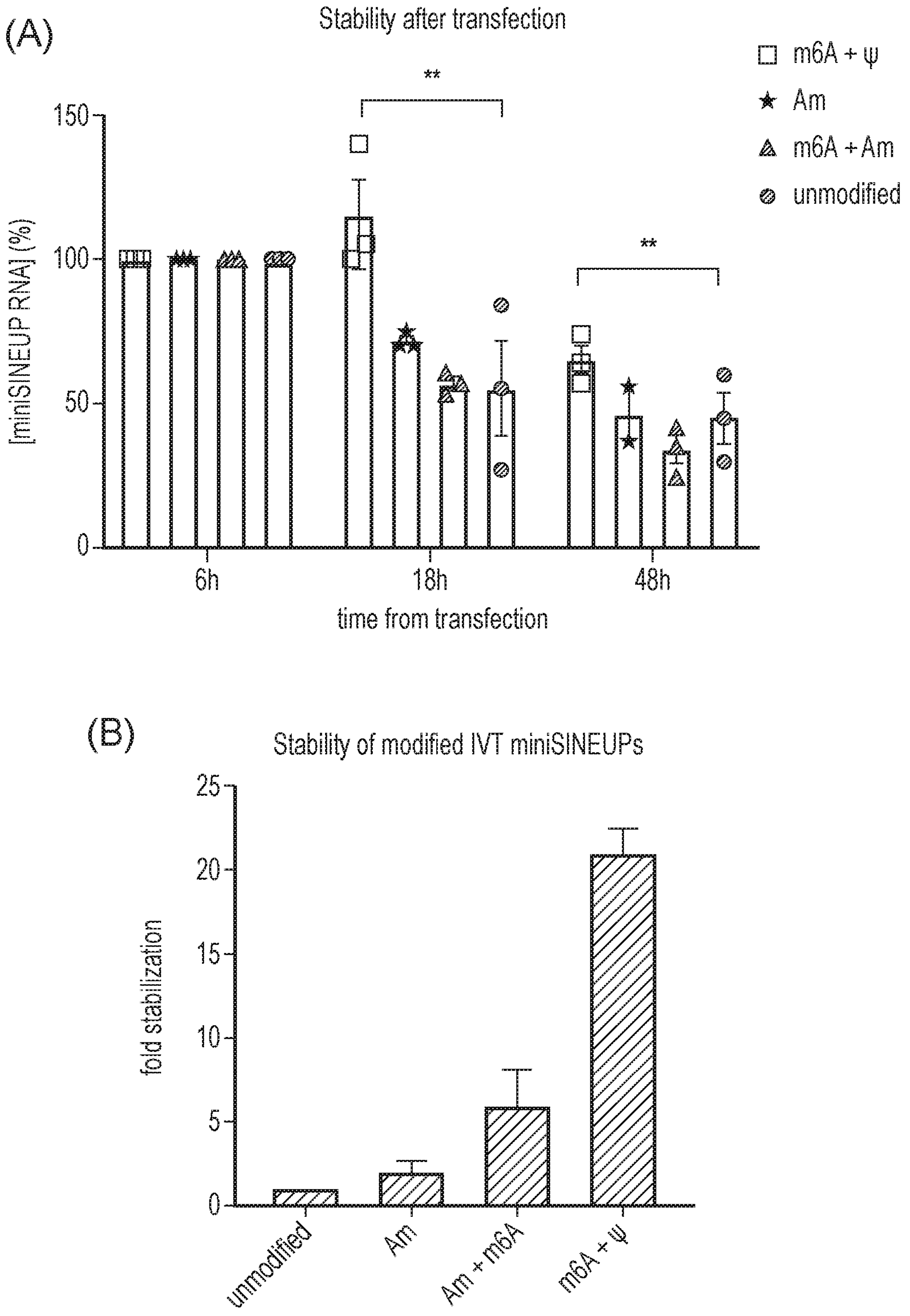

FIG. 8: Stability of unmodified and modified RNA after transfection. (A) Time course experiment showing amount of unmodified and modified IVT RNA over 48 hours following transfection, compared to the 6 hour time-point. (B) Fold stabilization of modified IVT RNA as compared to unmodified RNA. Data calculated as a ratio of normalized gene expression to fold RT efficiency (data not shown).

Figure 9:
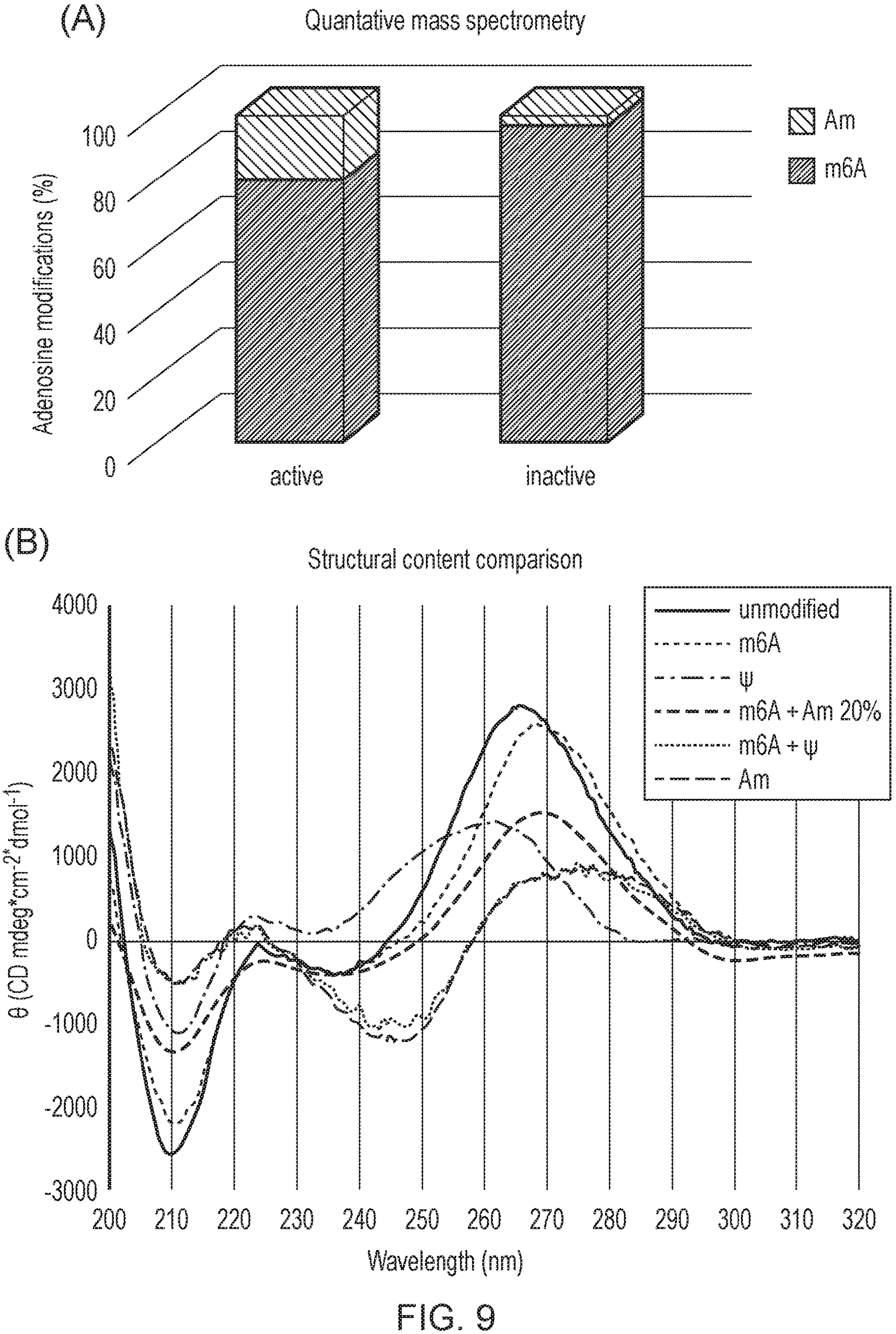
Figure 9:
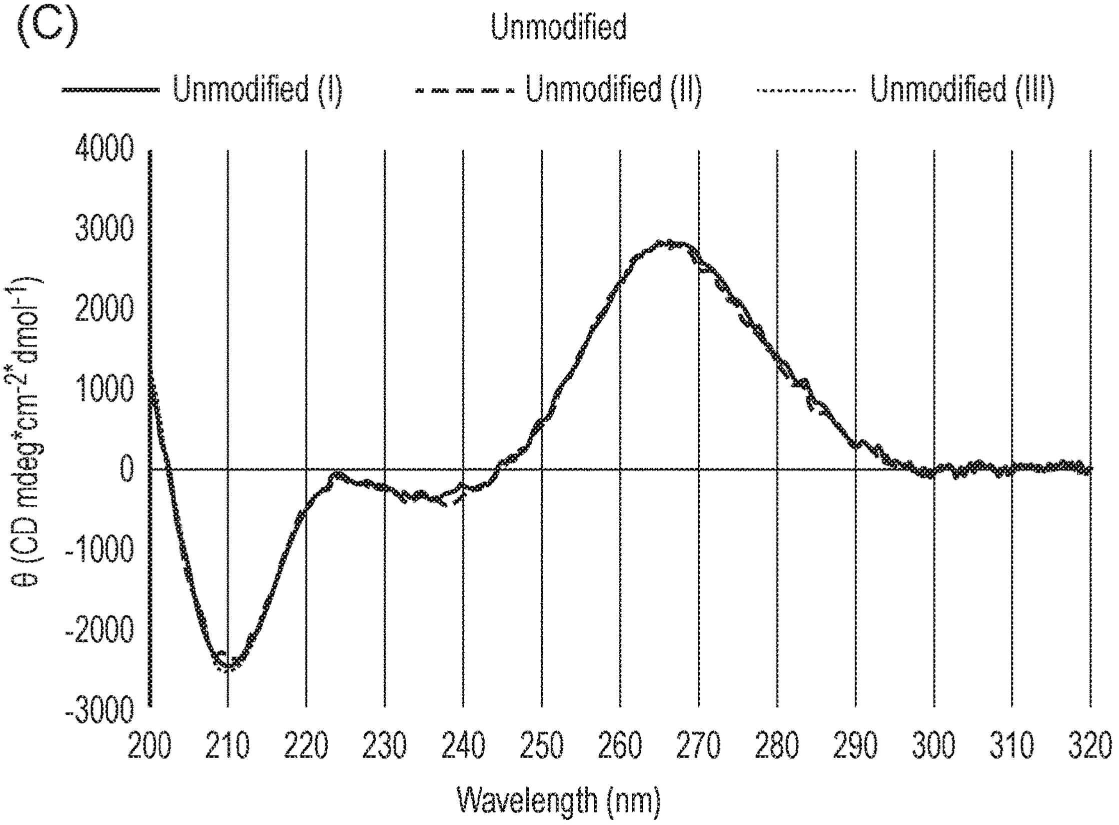
Figure 9:
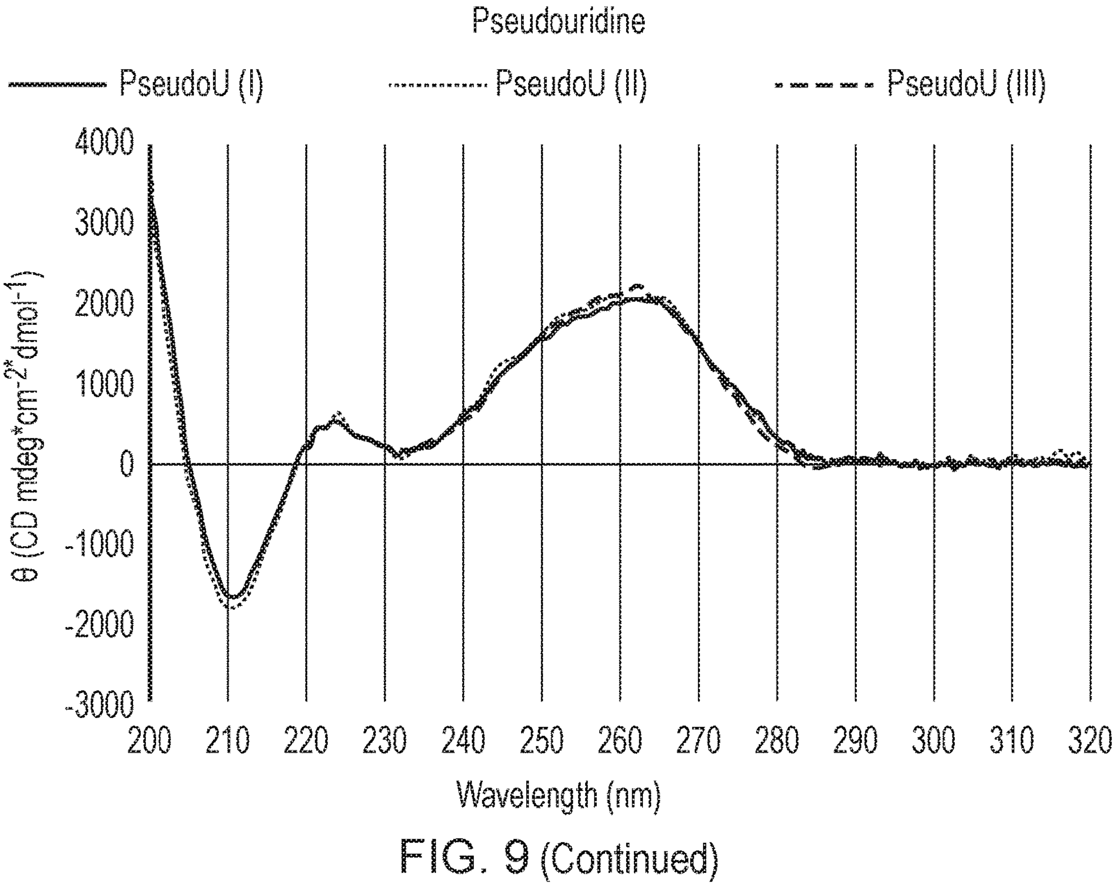
Figure 9:
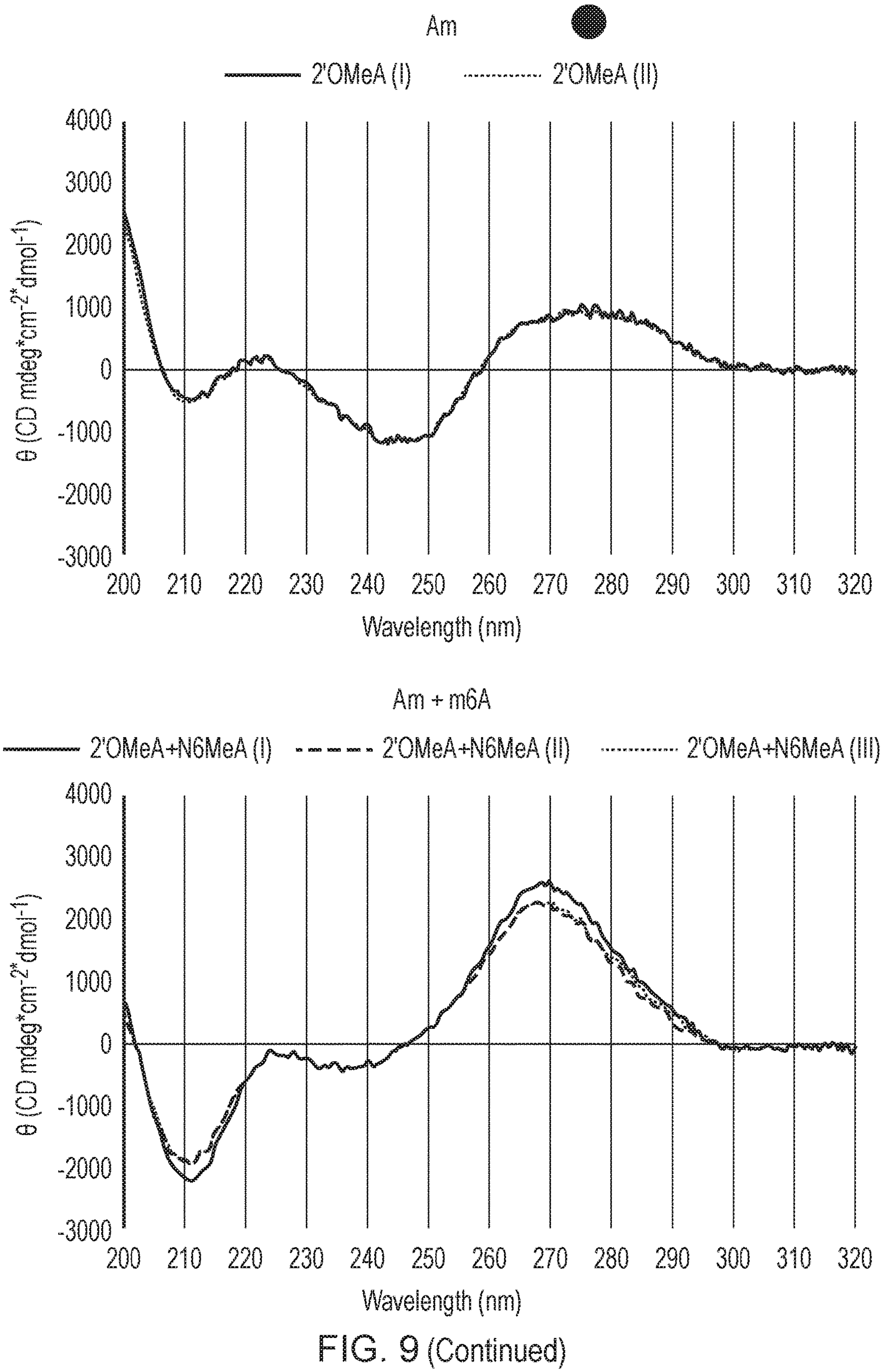
Figure 9:
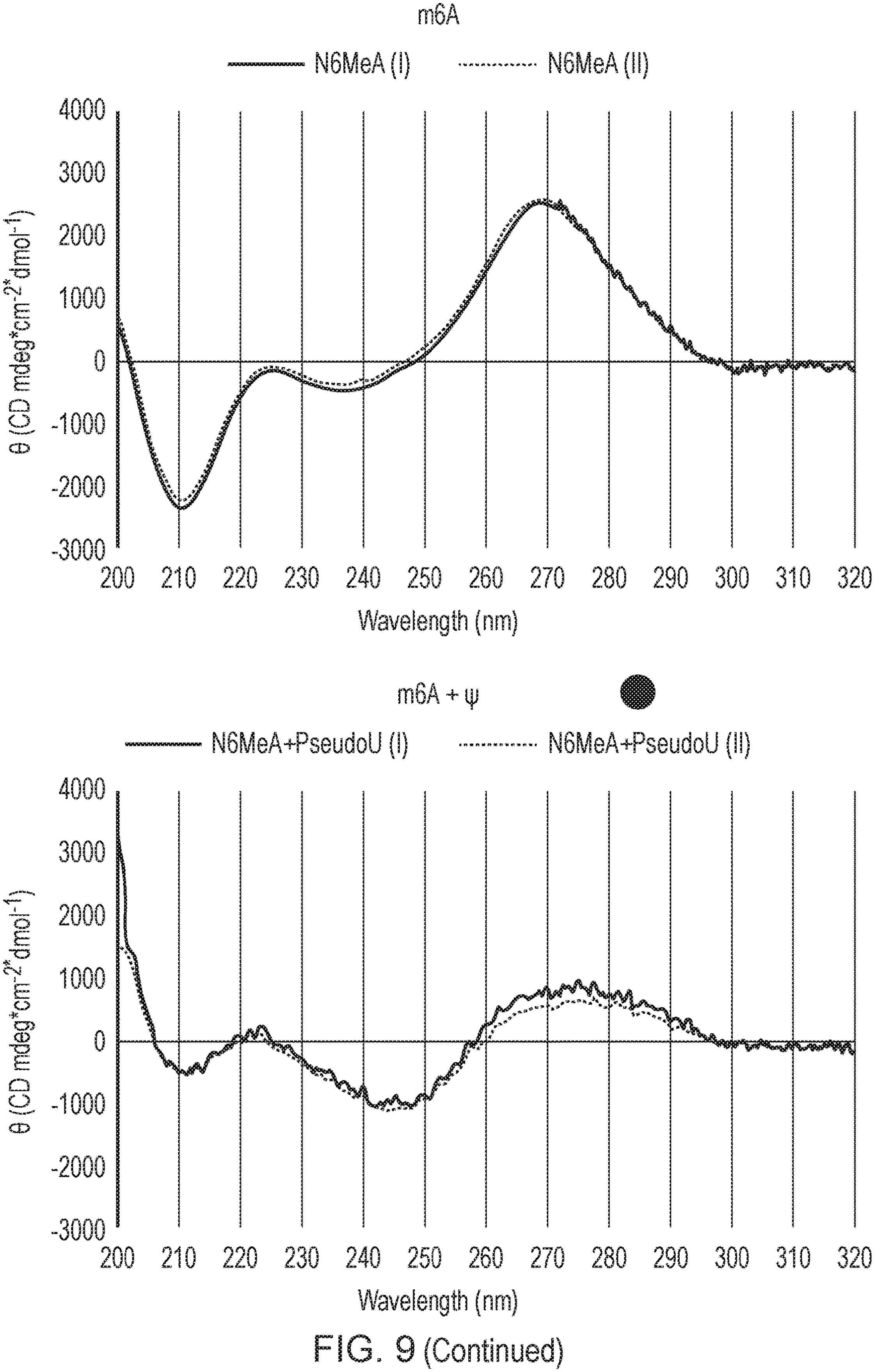
Figure 9:
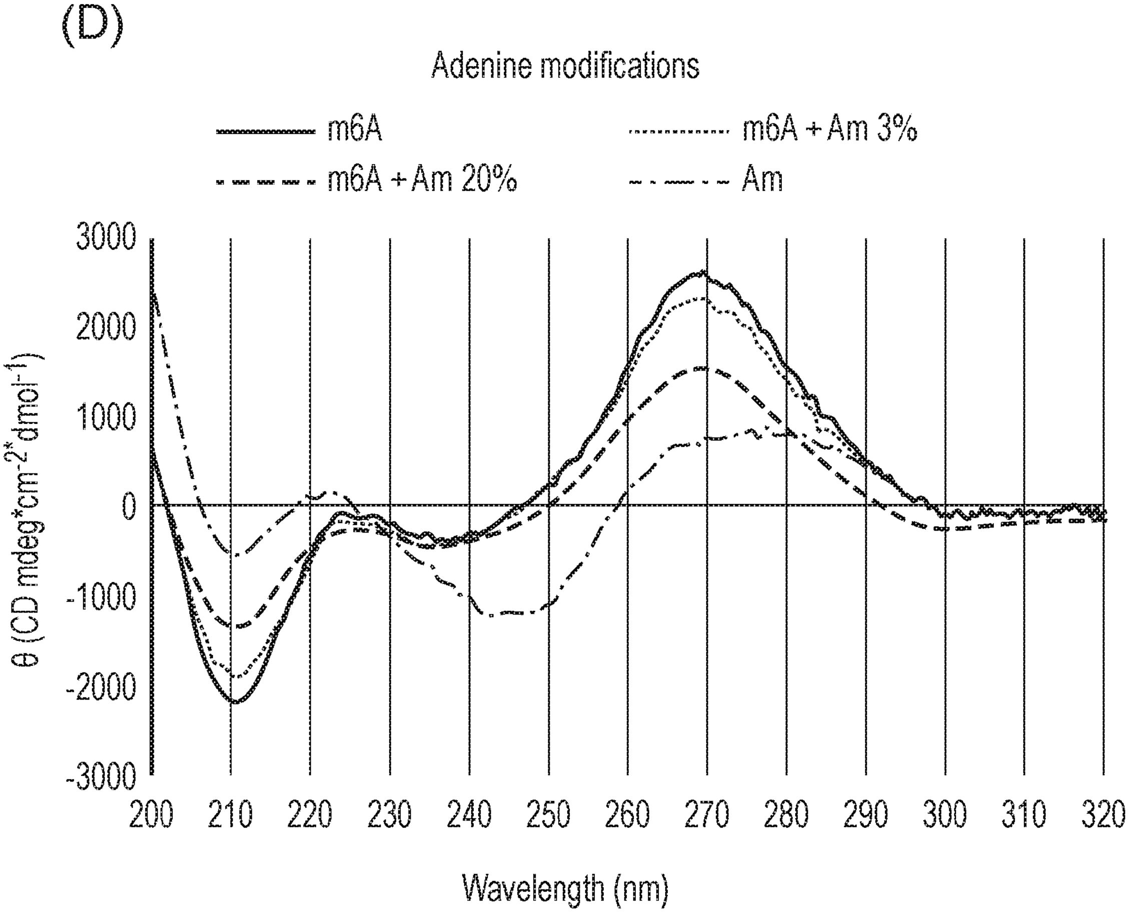

FIG. 9: Secondary structure of modified IVT SINEUP and structure-activity relationship. (A) Mass spectrometry quantification of the relative content of adenosine modifications in different IVT miniSINEUPs modified with Am+m6A mixtures, and their correlation with SINEUP activity. (B) Circular dichroism (CD) spectra of IVT miniSINEUP with various modifications showing possible structural determinants of activity; the spectra of the active modified IVT SINEUP RNA overlap (those containing Am or m6A+w) while inactive modified IVT SINEUP overlap with the spectra of inactive unmodified IVT SINEUP. (C) Individual CD spectra plots for unmodified and modified IVT SINEUP RNA. Dots mark functional miniSINEUPs (Am alone or m6A+ψ modified). (D) Comparison of CD spectra of IVT miniSINEUPs containing different proportions of adenosine modifications. (E) Thermal stability of unmodified and modified IVT miniSINEUPs.

Figure 10:
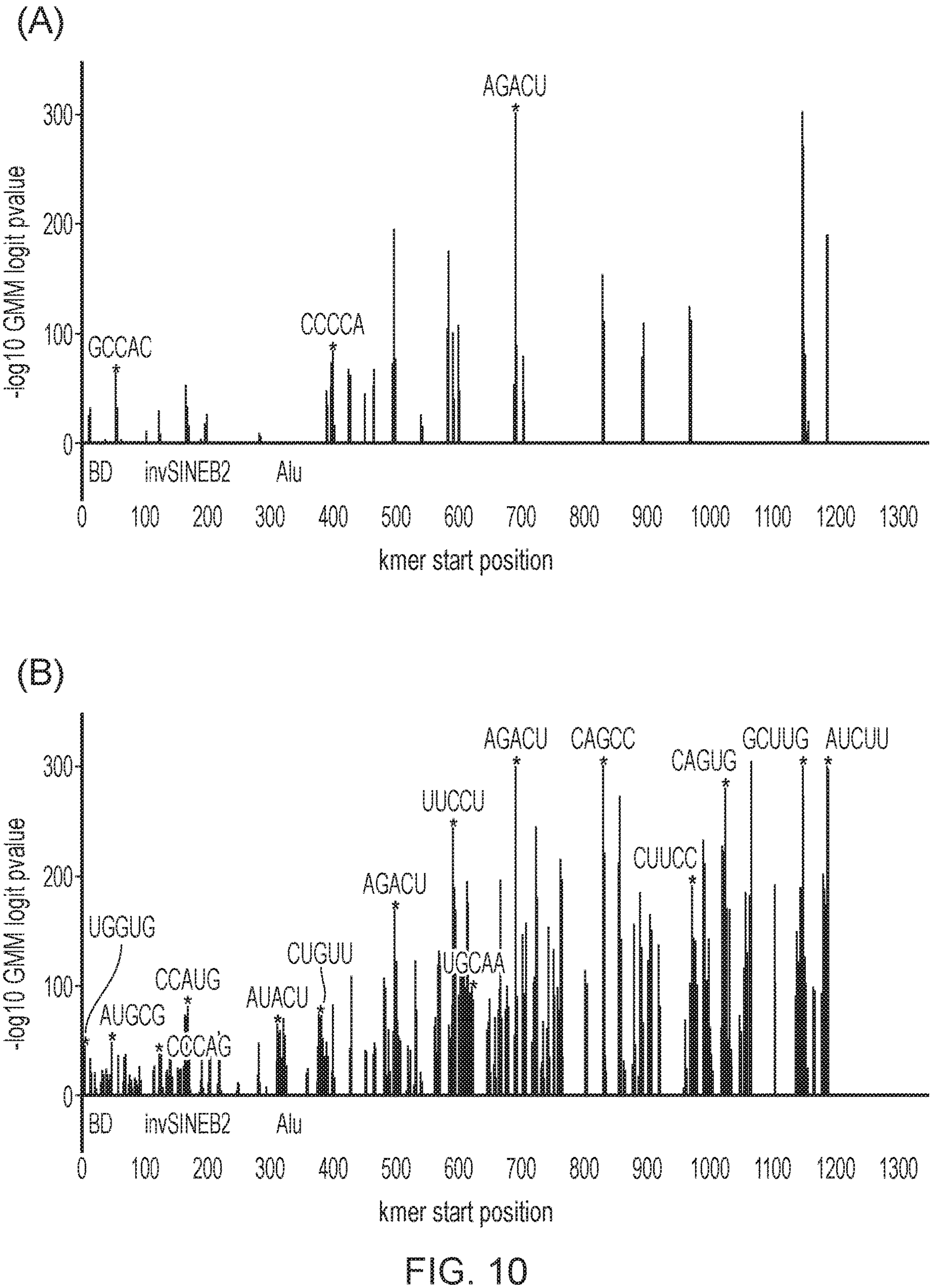

FIG. 10: Modification profile of mICT SINEUP-GFP RNA from an analysis of unmodified and modified IVT SINEUP-GFP. RNA modification profile of SINEUP-GFP, showing the Nanocompore GMM-logit p-value (y axis,-log 10) across the transcript length. The GMM-logit p-value was generated by the comparison between either (A) 0% modified IVT SINEUP-GFP and mICT SINEUP-GFP RNAs or (B) 20% pseudouridine-5'-triphosphate (w) mIVT SINEUP-GFP RNAs and mICT SINEUP-GFP RNAs. The enriched kmer peaks are indicated on the figures with an asterisk and the corresponding 5-mer sequence stated.

Figure 11:
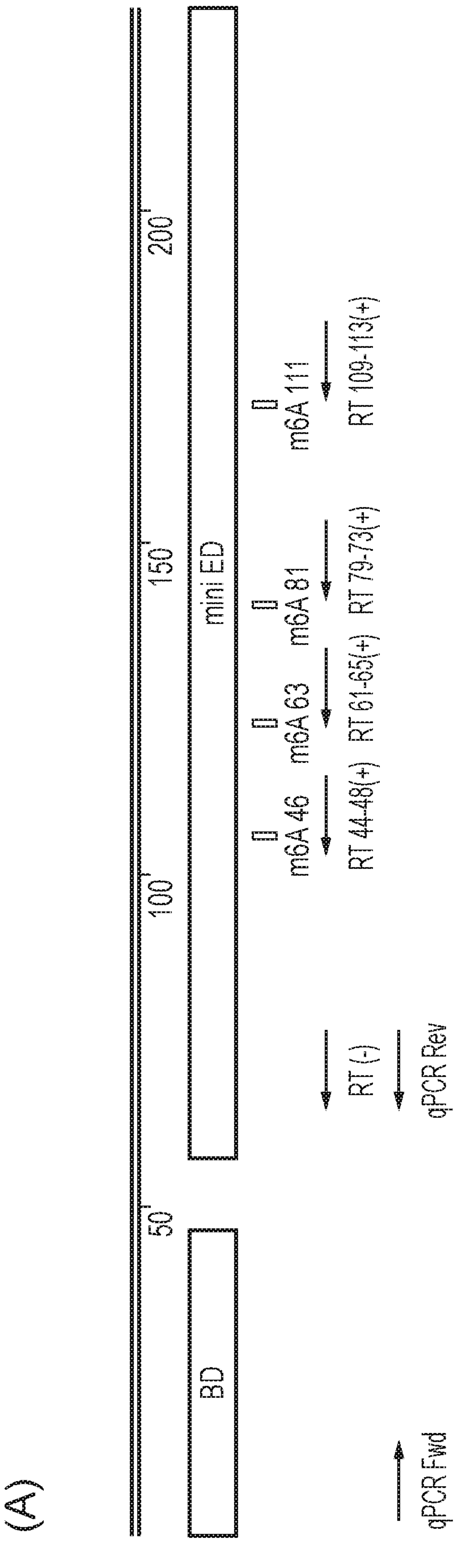
Figure 11:
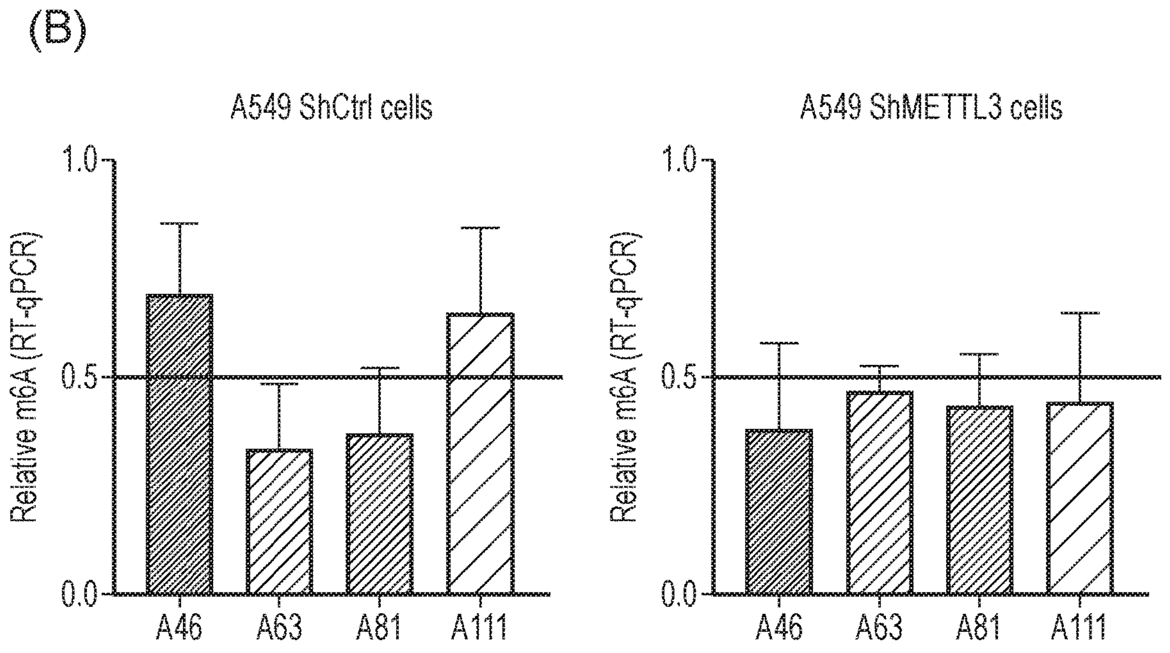
Figure 11:
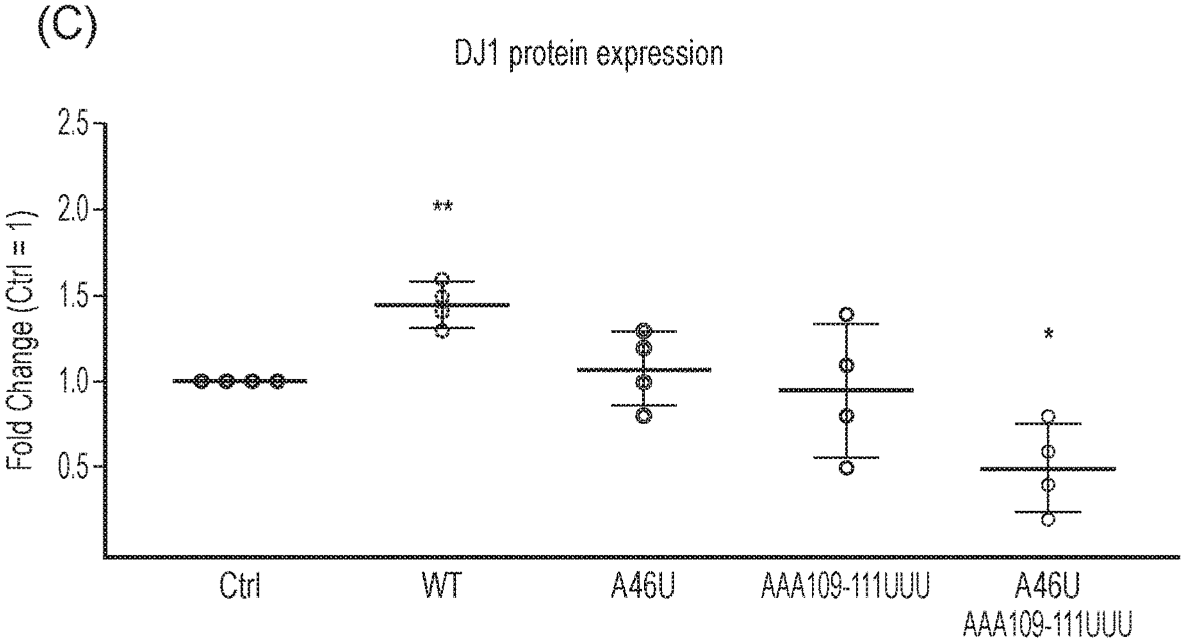
Figure 11:
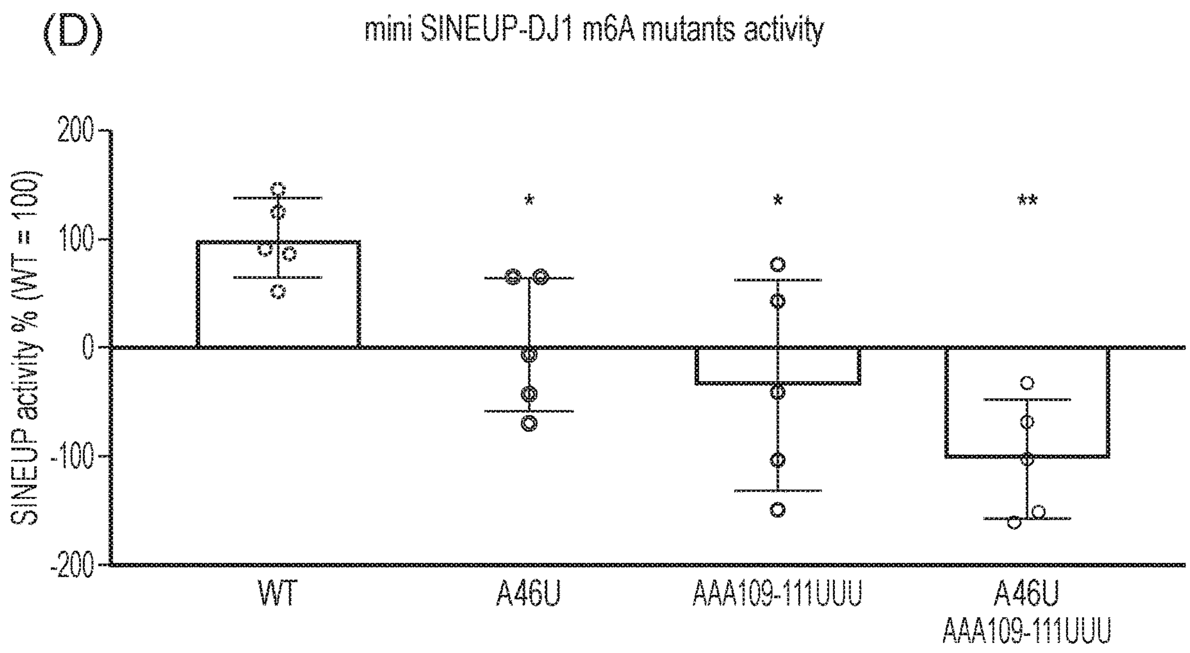
Figure 11:
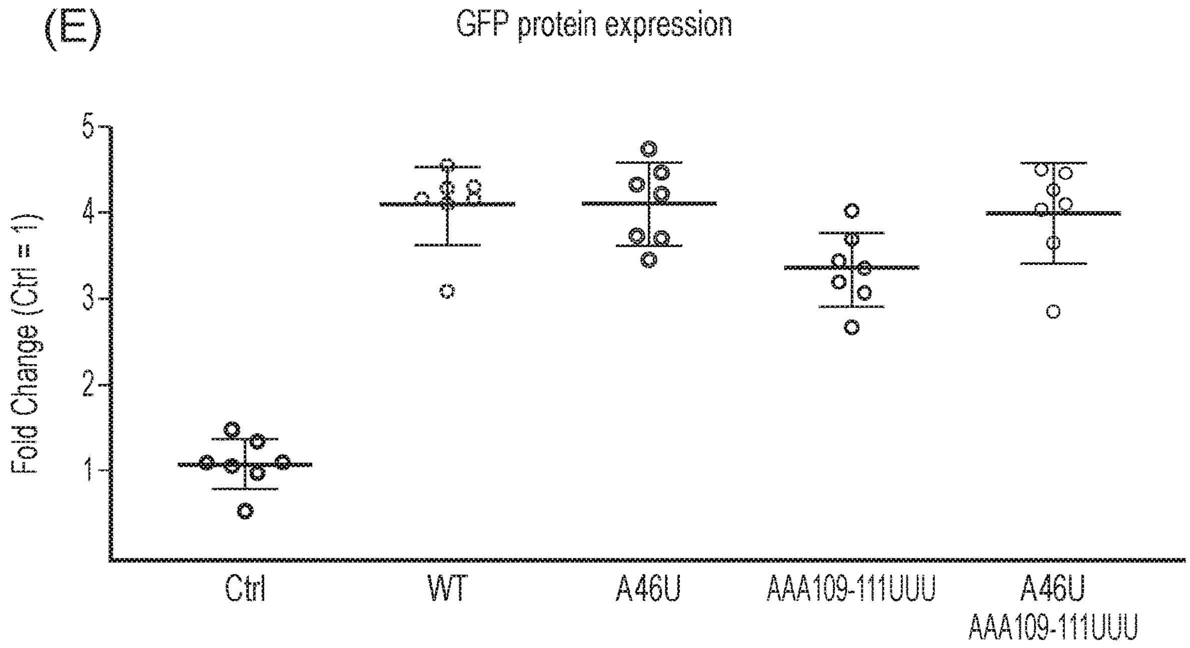
Figure 11:
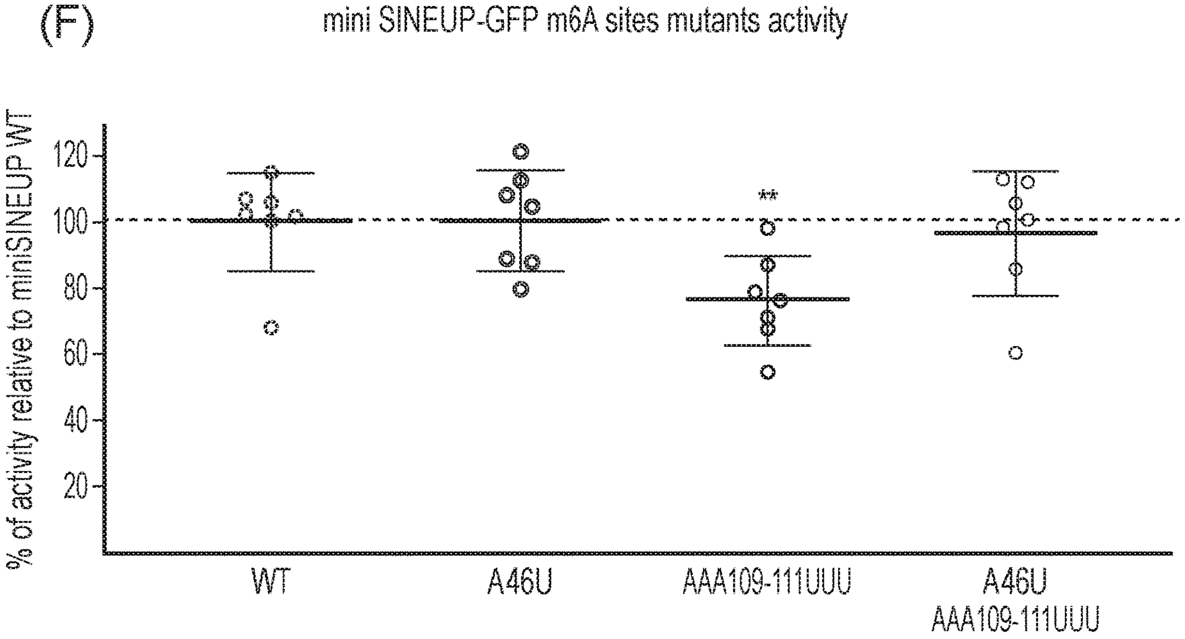
Figure 11:
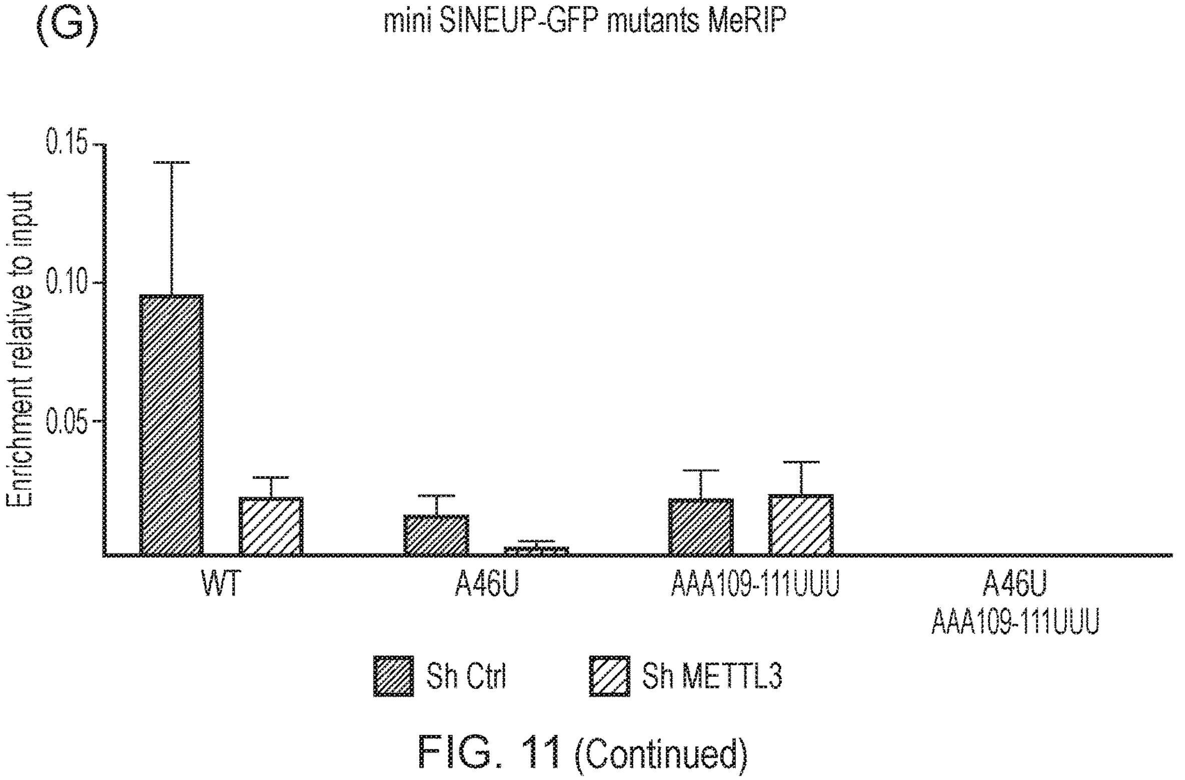

FIG. 11: Modification profile of mICT miniSINEUP RNA and effect of mutating methylation sites on SINEUP activity. (A) Schematic diagram showing relative positions of candidate m6A sites identified by RT-qPCR using BstI retrotranscriptase. (B) Results of m6A sites retro-transcription assay. Graph show the ratio of retro-transcription efficiency between BstI and standard retrotranscriptase in METTL3 knock-down (right panel) or control cells (left panel). (C) Fold change in DJ1 protein expression following transfection of either control, unmutated (WT) mini-SINEUP-DJ1 or miniSINEUP-DJ1 in which the indicated candidate m6A site was mutated to uracil to prevent methylation. (D) Percentage of SINEUP activity relative to unmutated (WT) miniSINEUP-DJ1 as in (B). (E) Fold change in GFP protein expression following transfection of either control, unmutated (WT) mini-SINEUP-GFP or miniSINEUP-GFP in which the indicated candidate m6A site was mutated to uracil to prevent methylation. (F) Percentage of SINEUP activity relative to unmutated (WT) miniSINEUP-GFP as in (D). (G) MeRIP of methylated miniSINEUP-GFP RNA of the indicated SINEUP RNA mutants in control or METLL3 knock-down cells.

DETAILED DESCRIPTION OF THE INVENTION

It is an object of the present invention to provide functional nucleic acid molecules that are suitable for direct administration, particularly for use as therapeutics (i.e. as nucleic acid therapeutics). Adding to current, DNA-based gene therapy approaches, an RNA-based druggable system has several advantages, such as avoiding the risk of foreign gene integration to the host genome and insertional mutations that may lead to unexpected side effects. In vitro transcribed (IVT) SINEUP RNAs can be used as an RNA-based drug tool to stimulate only specific target mRNA translation without altering the endogenous mRNA itself, reducing the incidence of unexpected immune responses by introducing nucleotide modifications into IVT SINEUPs. Additionally, IVT SINEUP RNAs can be easily reduced down to the smallest size of functional SINEUP RNA, which can be transported to the target organs while minimizing invasive effects to the host. Another example of producing RNA-based drug tools is by direct chemical synthesis, such as using an automated synthesiser, to produce an RNA-based oligonucleotide (also referred to as oligoribonucleotide). However, it will be appreciated that IVT will be preferred over direct chemical synthesis when producing long RNA-oligonucleotides due to the low coupling efficiency of RNA in direct chemical synthesis methods. The evidence provided herein shows that synthetic, chemically modified IVT (mIVT) SINEUPs have potential as an efficient, protein-producing tool in nucleic-acid-based therapies, and would aid those with diseases that are currently difficult to treat using conventional treatments including DNA-based gene therapy.

Definitions

The "functional nucleic acid molecule" referred to herein is a synthetic molecule described by the invention. In particular, "functional nucleic acid molecule" describes a nucleic acid molecule (e.g. DNA or RNA) that is capable of enhancing translation of a target mRNA of interest. The term "functional RNA molecule" refers to wherein the functional nucleic acid molecule is formed of RNA and the RNA molecule is capable of enhancing the translation of a target mRNA of interest. The functional molecules described herein may be referred to as trans-acting molecules.

The term "SINE" (Short Interspersed Nuclear Element) may be referred to as a non-LTR (long terminal repeat) retrotransposon, and is an interspersed repetitive sequence whose complete or incomplete copy sequences exist abundantly in genomes of living organisms.

The term "SINE B2 element" is defined in WO 2012/133947, where specific examples are also provided (see table starting on page 69 of the PCT publication). The term is intended to encompass both SINE B2 elements in direct orientation and in inverted orientation relative to the 5' to 3' orientation of the functional nucleic acid molecule. SINE B2 elements may be identified, for example, using programs like RepeatMask as published (Bedell et al. Bioinformatics. 2000 November; 16 (11): 1040-1. MaskerAid: a performance enhancement to RepeatMasker). A sequence may be recognizable as a SINE B2 element by returning a hit in a Repbase database with respect to a consensus sequence of a SINE B2, with a Smith-Waterman (SW) score of over 225, which is the default cutoff in the RepeatMasker program. Generally a SINE B2 element is not less than 20 bp and not more than 400 bp. Preferably, the SINE B2 is derived from tRNA.

By the term "functionally active fragment of a SINE B2 element" there is intended a portion of sequence of a SINE B2 element that retains protein translation enhancing efficiency. This term also includes sequences which are mutated in one or more nucleotides with respect to the wild-type sequences, but retain protein translation enhancing efficiency. The term is intended to encompass both SINE B2 elements in direct orientation and in inverted orientation relative to the 5' to 3' orientation of the functional nucleic acid molecule.

The terms "internal ribosome entry site (IRES) sequence" and "internal ribosome entry site (IRES) derived sequence" are defined in WO 2019/058304. IRES sequences recruit the 40S ribosomal subunit and promote cap-independent translation of a subset of protein coding mRNAs. IRES sequences are generally found in the 5' untranslated region of cellular mRNAs coding for stress-response genes, thus stimulating their translation in cis. It will be understood by the term "IRES derived sequence" there is intended a sequence of nucleic acid with a homology to an IRES sequence so as to retain the functional activity thereof, i.e. a translation enhancing activity. In particular, the IRES derived sequence can be obtained from a naturally occurring IRES sequence by genetic engineering or chemical modification, e.g. by isolating a specific sequence of the IRES sequence which remains functional, or mutating/deleting/introducing one or more nucleotides in the IRES sequence, or replacing one or more nucleotides in the IRES sequence with structurally modified nucleotides or analogs. More in particular, the skilled in the art would know that an IRES derived sequence is a nucleotide sequence capable of promoting translation of a second cistron in a bicistronic construct. Typically, a dual luciferase (Firefly luciferase, *Renilla* Luciferase) encoding plasmid is used for experimental tests. A major database exists, namely IRESite, for the annotation of nucleotide sequences that have been experimentally validated as IRES, using dual reporter or bicistronic assays (iresite.org/IRESite_web.php). Within the I RESite, a web-based tool is available to search for sequence-based and structure-based similarities between a query sequence of interest and the entirety of annotated and experimentally validated IRES sequences within the database. The output of the program is a probability score for any nucleotide sequence to be able to act as IRES in a validation experiment with bicistronic constructs. Additional sequence-based and structure-based web-based browsing tools are available to suggest, with a numerical predicting value, the IRES activity potentials of any given nucleotide sequence (ma.informatik.unit-freiburg.de/; regma.mbc.nctu.edu.tw/index1.php).

By the term "miniSINEUP" there is intended a nucleic acid molecule comprising (or consisting of) a binding domain (i.e. a complementary sequence to target mRNA), optionally a spacer sequence, and any SINE or SINE-derived sequence or IRES or IRES-derived sequence as the effector domain (Zucchelli et al., Front Cell Neurosci., 9:174, 2015).

By the term "microSINEUP" there is intended a nucleic acid molecule comprising (or consisting of) a binding domain (i.e. a complementary sequence to target mRNA), optionally a spacer sequence, and a functionally active fragment of the SINE or SINE-derived sequence or IRES-derived sequence. For example, the functionally active fragment may be a 77 bp sequence corresponding to nucleotides 44 to 120 of the SINE B2 element in AS Uchl1.

By the term "nanoSINEUP" there is intended a nucleic acid molecule comprising (or consisting of) a binding domain (i.e. a complementary sequence to target mRNA), optionally a spacer sequence, and a functionally active fragment of the SINE or SINE-derived sequence. For example, the functionally active fragment may be a 29 bp sequence corresponding to nucleotides 64 to 92 of the inverted SINE B2 element in AS Uchl1 (as defined in WO 2019/150346).

Polypeptide or polynucleotide sequences are said to be the same as or "identical" to other polypeptide or polynucleotide sequences, if they share 100% sequence identity over their entire length. Residues in sequences are numbered from left to right, i.e. from N- to C-terminus for polypeptides; from 5' to 3' terminus for polynucleotides.

For the purposes of comparing two closely-related polynucleotide sequences, the "% sequence identity" between a first nucleotide sequence and a second nucleotide sequence may be calculated using NCBI BLAST, using standard settings for nucleotide sequences (BLASTN). For the purposes of comparing two closely-related polypeptide sequences, the "% sequence identity" between a first polypeptide sequence and a second polypeptide sequence may be calculated using NCBI BLAST, using standard settings for polypeptide sequences (BLASTP). A "difference" between sequences refers to an insertion, deletion or substitution of a single nucleotide in a position of the second sequence, compared to the first sequence. Two sequences can contain one, two or more such differences. Insertions, deletions or substitutions in a second sequence which is otherwise identical (100% sequence identity) to a first sequence result in reduced % sequence identity.

Functional Molecules

According to a first aspect of the invention, there is provided a functional nucleic acid molecule (e.g. functional RNA molecule) comprising:

(a) at least one target determinant sequence comprising a sequence reverse complementary to a target mRNA sequence for which protein translation is to be enhanced; and (b) at least one regulatory sequence comprising a SINE B2 element or a functionally active fragment of a SINE B2 element, wherein the functional nucleic acid molecule comprises one or more chemical modifications.

The functional nucleic acid molecules provided herein are chemically modified prior to administration to the cell. This has been shown by the Examples provided herein to improve stability, especially for the development of in vitro transcribed (IVT) functional RNA molecules. Therefore, in one embodiment, the functional RNA molecule is an in vitro transcribed RNA molecule. It has also been shown by the Examples provided herein that in-cell transcribed (ICT) functional RNA molecules comprise such modifications. Thus, in another embodiment the functional nucleic acid molecule is in-cell transcribed, such as from an oligonucleotide comprising a sequence encoding the functional RNA molecule.

Evidence provided herein shows that chemically modified SINEUP RNAs are an efficient approach to enhance target protein level by direct transfection of synthetic RNA. The term "modification" or "chemical modification" refers to a structural change in, or on, the most common, natural ribonucleotides: adenosine, guanosine, cytidine, or uridine ribonucleotides. In particular, the chemical modifications described herein may be changes in or on a nucleobase (i.e. a chemical base modification), or in or on a sugar (i.e. a chemical sugar modification). The chemical modifications may be introduced co-transcriptionally (e.g. by substitution of one or more nucleotides with a modified nucleotide during synthesis), or post-transcriptionally (e.g. by the action of an enzyme).

Chemical modifications are known in the art, for example as described in The RNA Modification Database provided by The RNA Institute (mods.ma.albany.edu/mods/). Many modifications occur in nature, such as chemical modifications to natural transfer RNAs (tRNAs), which include, for example: 2'-O-Methyl (such as 2'-O-Methyladenosine, 2'-O-Methylguanosine and 2'-O-Methylpseudouridine), 1-Methyladenosine, 2-Methyladenosine, 1-Methylguanosine, 7-Methylguanosine, 2-Thiocytidine, 5-Methylcytidine, 5-Formylcytidine, Pseudouridine, Dihydrouridine, or the like.

In some embodiments, the functional nucleic acid molecule is uniformly modified (e.g. fully modified, modified throughout the entire sequence) for a particular modification. For example, the molecule can be uniformly modified with Pseudouridine (ψ), meaning that all uridine residues in the RNA sequence are replaced with Pseudouridine. Similarly, a nucleic acid can be uniformly modified for any type of nucleoside residue present in the sequence by replacement with a modified residue. The functional molecules may be partially or fully modified along the entire length of the molecule. For example, one or more or all or a given type of nucleotide (e.g. purine or pyrimidine, or any one or more or all of A, G, U, C) may be uniformly modified in a RNA molecule, or in a predetermined sequence region thereof (e.g. in the target determinant sequence and/or the regulatory sequence, including or excluding other sequences that may be present, such as the linker or the polyA tail).

The functional nucleic acid molecule may contain from about 1% to about 100% chemically modified bases and/or sugars (either in relation to overall nucleotide content, or in relation to one or more types of nucleotide, i.e. any one or more of A, U, C or G) or any intervening percentage thereof (e.g. from 1% to 20%, from 1% to 30%, from 1% to 40%, from 1% to 50%, from 1% to 60%, from 1% to 70%, from 1% to 80%, from 1% to 90%, from 1% to 95%, from 10% to 20%, from 10% to 30%, from 10% to 40%, from 10% to 50%, from 10% to 60%, from 10% to 70%, from 10% to 80%, from 10% to 90%, from 10% to 95%, from 10% to 100%, from 20% to 30%, from 20% to 40%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of unmodified A, U, C or G.

In one embodiment, at least 20% of the functional nucleic acid molecule contains chemical base modifications, such as at least 30%, 40%, 50%, 60%, 70%, 80%, 90%, 95% or 100% of the functional RNA molecule. In one embodiment, at least 20% of the functional RNA molecule contains chemical sugar modifications, such as at least 30%, 40%, 50%, 60%, 70%, 80%, 90%, 95% or 100% of the functional molecule.

In one embodiment, the chemical modification is a chemical base modification. The chemical base modification may be selected from a modification of an adenine, cytosine, guanine and/or uracil base.

In one embodiment, at least 20% of the uracil bases of the functional nucleic acid molecule are chemically modified, such as at least 30%, 40%, 50%, 60%, 70%, 80%, 90%, 95% or 100% of the uracil bases. In a further embodiment, 20% of the uracil bases of the functional nucleic acid molecule are chemically modified. In another embodiment, 50% of the uracil bases of the functional nucleic acid molecule are chemically modified. In a yet further embodiment, 100% of the uracil bases of the functional nucleic acid molecule are chemically modified. In one embodiment, at least 20% of the adenine bases of the functional molecule are chemically modified, such as at least 30%, 40%, 50%, 60%, 70%, 80%, 90%, 95% or 100% of the adenine bases. In a particular embodiment, 20% or more of the adenine bases of the functional nucleic acid molecule are chemically modified. Thus, in a further embodiment, 20% of the adenine bases of the functional nucleic acid molecule are chemically modified. In a yet further embodiment, 50% of the adenine bases of the functional nucleic acid molecule are chemically modified. In a still further embodiment, 100% of the adenine bases of the functional nucleic acid molecule are chemically modified. In one embodiment, at least 20% of the cytosine bases of the functional molecule are chemically modified, such as at least 30%, 40%, 50%, 60%, 70%, 80%, 90%, 95% or 100% of the cytosine bases. In one embodiment, at least 20% of the guanine bases of the functional molecule are chemically modified, such as at least 30%, 40%, 50%, 60%, 70%, 80%, 90%, 95% or 100% of the guanine bases.

In one embodiment, the chemical base modification is selected from methylation and/or isomerisation. In a further embodiment, the chemical base modification is selected from the group consisting of: Pseudouridine (ψ), N1-Methylpseudouridine (N1mψ), 5-Methylcytidine (m5C) and N6-Methyladenosine (m6A). In a further embodiment, the chemical base modification is selected from the group consisting of: Pseudouridine, N1-Methylpseudouridine and N6-Methyladenosine.

In one embodiment, the chemical modification is a chemical sugar modification. In one embodiment, the chemical sugar modification is methylation. In one embodiment, the chemical sugar modification is a 2' modification, such as a 2'-O-Methyl modification. In a further embodiment, the chemical sugar modification is 2'-O-Methyladenosine (Am), such as wherein 100% of the adenine bases of the functional nucleic acid molecule are 2'-O-Methyladenosine.

It will be understood that the functional nucleic acid molecule may comprise combinations of chemical modifications, such as one or more types of chemical base modification and one or more types of chemical sugar modification. For example, in one embodiment, the functional nucleic acid molecule comprises N6-Methyladenosine and 2'-O-Methyladenosine modifications. In a further embodiment, the amount of 2'-O-Methyladenosine compared to N6-Methyladenosine (Am: m6A) is greater than 3:97, such as greater than 4:96, greater than 5:95, greater than 6:94, greater than 7:93, greater than 8:92, greater than 9:91, greater than 10:90, greater than 11:89, greater than 12:88, greater than 13:87, greater than 14:86, greater than 15:85, greater than 16:84, greater than 17:83, greater than 18:82 or greater than 19:81. In a yet further embodiment, the functional nucleic acid molecule comprises 2'-O-Methyladenosine and N6-Methyladenosine modifications at an Am: m6A ratio of 20:80. Thus, in one embodiment the functional nucleic acid molecule comprises 20% or more, such as 20%, of adenosine bases modified to 2'-O-Methyladenosine (Am). In a further embodiment, the functional nucleic acid molecule comprises 80% or less, such as 80%, of adenosine bases modified to N6-Methyladenosine (m6A). Thus, in a yet further embodiment 100% of the adenine bases of the functional nucleic acid molecule are chemically modified, wherein 20% or more are 2'-O-Methyladenosine and 80% or less are N6-Methyladenosine. In a still further embodiment, 20% of the chemically modified adenosine bases are 2'-O-Methyladenosine and 80% are N6-Methyladenosine. In other embodiments, the functional nucleic acid molecule comprises N6-Methyladenosine and Pseudouridine modifications. For example, wherein 100% of the adenine bases of the functional nucleic acid molecule are N6-Methyladenosine and 100% of the uracil bases are Pseudouridine.

In one embodiment, the target determinant sequence comprises one or more chemical base and/or sugar modifications. In an alternative embodiment, the target determinant sequence does not comprise any chemical base and/or sugar modifications.

In one embodiment, the regulatory sequence comprises one or more chemical base and/or sugar modifications.

In one embodiment, both the target determinant sequence and regulatory sequence comprise one or more chemical base and/or sugar modifications.

In one embodiment, the one or more chemical base or sugar modifications are at the 5'-end, the 3'-end, or both ends of said functional nucleic acid molecule. In one embodiment, the one or more chemical base or sugar modifications are located throughout the functional nucleic acid molecule.

In one embodiment, the functional nucleic acid molecule further comprises at least one linker sequence between the target determinant sequence and the regulatory sequence. SEQ ID NO: 50 is a non-limiting example of the spacer/linker sequence. In a further embodiment, the linker sequence comprises one or more chemical base and/or sugar modifications.

It is known that chemical modifications such as the chemical base and/or sugar modifications described herein are naturally introduced into nucleic acids during transcription in cells. Such in-cell transcribed (ICT) nucleic acids may therefore be referred to as modified in-cell transcribed (mICT) nucleic acids. Thus, in some embodiments the functional nucleic acid molecule comprises one or more chemical base and/or sugar modifications caused by in-cell transcription. In other embodiments, the functional nucleic acid molecule comprises one or more chemical base and/or sugar modifications found in an ICT functional nucleic acid molecule, such as a mICT functional nucleic acid molecule. For example, wherein the functional nucleic acid molecule is an in vitro transcribed (IVT) or directly synthesised SINEUP RNA, one or more chemical modifications may be introduced into the IVT/directly synthesised SINEUP RNA in order to mimic the chemical modifications found in an ICT SINEUP RNA, such as a mICT SINEUP RNA. It will be appreciated that IVT and directly synthesised functional nucleic acid molecules, such as IVT SINEUP RNA, which comprise modifications mimicking those found in mICT nucleic acids will likely have similar stability to mICT nucleic acids when transfected into cells. Thus, introducing modifications found in mICT functional nucleic acid molecules into IVT or directly synthesised functional nucleic acid molecules may lead to the generation of stable and functional nucleic acid molecules. In one embodiment, the modifications in a mICT functional nucleic acid molecule, such as a mICT SINEUP RNA, are identified using sequencing. An example of a suitable sequencing technique is the Oxford Nanopore method, and comparison of mICT functional nucleic acids with modified or unmodified IVT functional nucleic acid molecules may be by Nanocompore. In another embodiment, the modifications are identified using RT-qPCR. An example of a suitable RT-qPCR technique for identifying modifications is the method described in Castellanos-Rubio et al. (2019) Sci. Rep., 9 (4220) (doi: doi.org/10.1038/s41598-019-40018-6) which uses the diminished capacity of the Bstl enzyme to retrotranscribe m6A residues to identify candidate positions for methylation and m6A residues.

Thus, in some embodiments the chemical modification and/or combination of chemical modifications is specific to the functional nucleic acid molecule, e.g. to the sequence of the SINEUP RNA. Such functional nucleic acid molecule-specific chemical modifications and/or combinations may be identified by sequencing of a mICT functional nucleic acid or by performing RT-qPCR as described herein. Chemical modifications and/or combinations may then be introduced into an IVT or directly synthesised functional nucleic acid molecule having the same sequence as the sequenced mICT functional nucleic acid in order to mimic those identified in the mICT functional nucleic acid molecule.

In one embodiment, the functional nucleic acid molecule is circular. This conformation leads to a much more stable molecule that is degraded with greater difficulty within the cell (exonucleases cannot degrade circular molecules) and therefore remains active for a longer time.

In one embodiment, the functional nucleic acid molecule comprises a 3'-polyadenylation (polyA) tail. A "3'-polyA tail" refers to a long chain of adenine nucleotides added to the 3'-end of the transcription which provides stability to the RNA molecule and can promote translation.

In one embodiment the functional nucleic acid molecule comprises a 5'-cap. A "5'-cap" refers to an altered nucleotide at the 5'-end of the transcript which provides stability to the molecule, particularly from degradation from exonucleases, and can promote translation. Most commonly, the 5'-cap is a 7-methylguanylate cap (m7G), i.e. a guanine nucleotide connected to the RNA via a 5' to 5' triphosphate linkage and methylated on the 7 position.

Regulatory Sequence

The regulatory sequence has protein translation enhancing efficiency. The increase of the protein translation efficiency indicates that the efficiency is increased as compared to a case where the functional nucleic acid molecule according to the present invention is not present in a system. In one embodiment, expression of the protein encoded by the target mRNA is increased by at least 1.2 fold, such as at least 1.5 fold, in particular at least 2 fold. In a further embodiment, expression of the protein encoded by the target mRNA is increased between 1.2 to 3 fold, such as between 1.2 and 1.7 fold.

In one embodiment, the regulatory sequence is located 3' of the target binding sequence. The regulatory sequence may be in a direct or inverted orientation relative to the 5' to 3' orientation of the functional nucleic acid molecule. Reference to "direct" refers to the situation in which the regulatory sequence is embedded (inserted) with the same 5' to 3' orientation as the functional nucleic acid molecule. Instead, "inverted" refers to the situation in which the regulatory sequence is 3' to 5' oriented relative to the functional nucleic acid molecule.

In one embodiment, the regulatory sequence comprises a SINE B2 element or a functionally active fragment of a SINE B2 element. The SINE B2 element is preferably in an inverted orientation relative to the 5' to 3' orientation of the functional nucleic acid molecule, i.e. an inverted SINE B2 element. As mentioned in the definitions section, inverted SINE B2 elements are disclosed and exemplified in WO 2012/133947.

Short fragments of the regulatory sequence (such as a SINE B2 element) are particularly useful when providing functional RNA molecules for use as a nucleic acid therapeutic. RNA molecules are highly unstable in living organisms, therefore stability provided by the chemical modifications as described herein, is more effective for shorter RNA molecules. Therefore, in one embodiment, the regulatory sequence comprises a functionally active fragment which is less than 250 nucleotides, such as less than 100 nucleotides.

Preferably, the at least one regulatory sequence comprises a sequence with at least 90% sequence identity, preferably at least 95% sequence identity, more preferably 100% sequence identity with a sequence selected from the group consisting of SEQ ID NO: 1-49. In one embodiment, the at least one regulatory sequence consists of a sequence with at least 90% sequence identity, preferably at least 95% sequence identity, more preferably 100% sequence identity with a sequence selected from the group consisting of SEQ ID NO: 1-49.

SEQ ID NO: 1 provides the full length inverted SINE B2 transposable element derived from AS Uchl1. Functional fragments derived from the inverted SINE B2 element are particularly preferred, such as SEQ ID NO: 2 (the 167 nucleotide inverted SINE B2 element in AS Uchl1), SEQ ID NO: 3 (the 77 nucleotide variant of the inverted SINE B2 element in AS Uchl1 that includes nucleotides 44 to 120), SEQ ID NO: 4 (the 38 nucleotide variant of the inverted SINE B2 element in AS Uchl1 that includes nucleotides 59 to 96) or SEQ ID NO: 5 (the 29 nucleotide variant of the inverted SINE B2 element in AS Uchl1 that includes nucleotides 64 to 92).

Other exemplary SINE B2 elements are provided. SEQ ID NO: 6-21 are further functionally active fragments of inverted SINE B2 transposable element derived from AS Uchl1 to those described above. SEQ ID NO: 22-33 are mutated functionally active fragments of inverted SINE B2 transposable element derived from AS Uchl1. SEQ ID NO: 34-49 are different SINE B2 transposable elements.

Alternatively, the regulatory sequence comprises an IRES sequence or an IRES derived sequence. Therefore, in one embodiment, the regulatory sequence comprises an IRES sequence or an IRES derived sequence. Said sequence enhances translation of the target mRNA sequence.

Several IRESs having sequences ranging from 48 to 576 nucleotides have been tested with success, e.g. human Hepatitis C Virus (HCV) IRESs, human poliovirus IRESs, human encephalomyocarditis (EMCV) virus, human cricket paralysis (CrPV) virus, human Apaf-1, human ELG-1, human c-MYC, human dystrophin (DMD). Such sequences have been disclosed, defined and exemplified in WO 2019/058304.

In a further embodiment, the regulatory sequence comprises a short free right Alu monomer repeat element (FRAM) sequence, such as that found in the R12A-AS1 natural antisense transcript of the human protein phosphatase 1 regulatory subunit 12A (PPP1R12A; Schein et al. (2016) Scientific Reports, 6(33605), doi: doi.org/10.1038/srep33605)

Target Determinant Sequence

The target determinant sequence (also referred to as the target binding sequence) is the portion of the functional RNA molecule that binds to the target mRNA.

In WO 2012/133947 it was already shown that the target binding sequence needs to have only about 60% similarity with a sequence reverse complementary to the target mRNA. As a matter of fact, the target binding sequence can even display a large number of mismatches and retain activity.

The target binding sequence comprises a sequence which is sufficient in length to bind to the target mRNA transcript. Therefore, the target binding sequence may be at least 10 nucleotides long, such as at least 14 nucleotides long, such as least 18 nucleotides long. Furthermore, the target binding sequence may be less than 250 nucleotides long, preferably less than 200 nucleotides long, less than 150 nucleotides long, less than 100 nucleotides long, less than 80 nucleotides long, less than 60 nucleotides long or less than 50 nucleotides long. In one embodiment, the target binding sequence is between 4 and 50 nucleotides in length, such as between 18 and 44 nucleotides long.

The target binding sequence may be designed to hybridise with the 5'-untranslated region (5' UTR) of the target mRNA sequence. In one embodiment, the sequence is reverse complementary to 0 to 50 nucleotides, such as 0 to 40, 0 to 30, 0 to 21 or 0 to 14 nucleotides of the 5' UTR. Alternatively, or in combination, the target binding sequence may be designed to hybridise to the coding sequence (CDS) of the target mRNA sequence. In one embodiment, the sequence is reverse complementary to 0 to 40 nucleotides, such as 0 to 32, 0 to 18 or 0 to 4 nucleotides of the CDS.

The target binding sequence may be designed to hybridise to a region upstream of an AUG site (start codon), such as a start codon within the CDS, of the target mRNA sequence.

In one embodiment, the sequence is reverse complementary to 0 to 80 nucleotides, such as 0 to 70 or 0 to 40 nucleotides of the AUG site. Alternatively, or in combination, the target binding sequence may be designed to hybridise to the target mRNA sequence downstream of said AUG site. In one embodiment, the sequence is reverse complementary to 0 to 40 nucleotides, such as 0 to 4 nucleotides of the target mRNA sequence downstream of said AUG site.

In one embodiment, the target determinant sequence is at least 10 nucleotides long and comprises, from 3' to 5':

- a sequence reverse complementary to 0 to 50 nucleotides of the 5' untranslated region (5' UTR) and 0 to 40 nucleotides of the coding sequence (CDS) of the target mRNA sequence; or
- a sequence reverse complementary to 0 to 80 nucleotides of the region upstream of an AUG site (start codon) of the target mRNA and 0 to 40 nucleotides of the CDS of the target mRNA sequence downstream of said AUG site.

In one embodiment, the target determinant sequence is at least 14 nucleotides long and comprises, from 3' to 5':

- a sequence reverse complementary to 0 to 40 nucleotides of the 5' UTR and 0 to 32 nucleotides of the CDS of the target mRNA sequence; or
- a sequence reverse complementary to 0 to 70 nucleotides of the region upstream of an AUG site (start codon) of the target mRNA and 0 to 4 nucleotides of the CDS of the target mRNA sequence downstream of said AUG site.

Compositions and Methods

The functional nucleic acid molecule of the invention may be administered as naked or unpackaged RNA. Alternatively, the functional nucleic acid molecule may be administered as part of a composition, for example compositions comprising a suitable carrier. In certain embodiments, the carrier is selected based upon its ability to facilitate the transfection of a target cell with one or more functional nucleic acid molecules.

Therefore, according to a further aspect of the invention, there is provided a composition comprising the functional nucleic acid molecule described herein.

A suitable carrier may include any of the standard pharmaceutical carriers, vehicles, diluents or excipients known in the art and which are generally intended for use in facilitating the delivery of nucleic acids, such as RNA. Liposomes, exosomes, lipidic particles or nanoparticles are examples of suitable carriers that may be used for the delivery of RNA. In a preferred embodiment, the carrier or vehicle delivers its contents to the target cell such that the functional nucleic acid molecule is delivered to the appropriate subcellular compartment, such as the cytoplasm.

The functional nucleic acid molecule as described herein may also be administered by administering an RNA-based oligonucleotide (also referred to as an oligoribonucleotide) comprising the modified functional nucleic acid molecule. Thus, according to a further aspect of the invention there is provided an RNA-based oligonucleotide comprising the modified functional nucleic acid described herein. As described hereinbefore, such RNA-based oligonucleotides may be produced by direct chemical synthesis. Direct chemical synthesis of modified RNA-based oligonucleotides may involve two strategies: i) the provision of a modified phosphoramidite building block and its subsequent incorporation into the RNA chain/oligonucleotide; and/or ii) post-synthesis RNA modification based on selective reactions of bases within the full length oligonucleotide, which allows for site-specific and controlled incorporation of modifications into the oligonucleotide sequence (see Bartosik et al. (2020) Molecules, 25:3344, doi: 10.3390/molecules25153344). Post-synthetic modification also allows the possibility for one building block within an RNA oligonucleotide to react with a wide variety of reagents, providing several differently modified oligonucleotides from the same starting sequence. In one embodiment, the RNA-based oligonucleotide comprising the functional nucleic acid molecule is modified, i.e. it comprises chemical modifications as described herein. In a further embodiment, the RNA-based oligonucleotide comprises site-specific modifications in the functional nucleic acid sequence as described herein. In a yet further embodiment, the site-specific modifications mimic those found in an ICT SINEUP RNA, such as a mICT SINEUP RNA. Thus, in some embodiments the directly synthesised RNA-based oligonucleotide comprises site-specific chemical base and/or sugar modifications, such as modifications introduced post-synthesis, found in an ICT functional nucleic acid molecule, such as a mICT functional nucleic acid molecule. In other embodiments, the site-specific modifications are non-natural chemical modifications. Thus, in one embodiment the directly synthesised RNA-based oligonucleotide comprises non-natural chemical modifications and/or naturally occurring chemical modifications.

Another method of administration of the functional nucleic acid molecule is by an oligonucleotide encoding the functional nucleic acid, for example by administering a plasmid comprising a sequence encoding the functional nucleic acid to a cell. In this context, the terms "administration" and "delivery" are interchangeable. Thus, according to another aspect of the invention there is provided an oligonucleotide comprising a sequence encoding for the functional nucleic acid molecule described herein, such as the chemically modified functional RNA molecule as described herein.

As described hereinbefore, chemical modifications are naturally introduced into nucleic acids during transcription in cells. Thus, in some embodiments the oligonucleotide comprises a sequence encoding the chemically modified functional nucleic acid molecule as described herein when transcribed in a cell. In a further embodiment, the sequence encodes a modified functional nucleic acid molecule comprising one or more chemical modifications described herein. In some embodiments, the site-specific modifications are non-natural chemical modifications. Thus, in one embodiment the oligonucleotide comprises non-natural chemical modifications and/or naturally occurring chemical modifications. It will be appreciated that any herein described chemical modification, including combination, amount, proportion, ratio or region of the functional nucleic acid molecule comprising the chemical modification may be applied to these aspects and embodiments of the invention relating to oligonucleotides comprising a functional nucleic acid molecule-encoding sequence and directly synthesised RNA-based oligonucleotides.

The functional nucleic acid molecules of the invention can enhance translation of the target gene of interest with no effect on mRNA quantities of the target gene. Therefore they can successfully be used as molecular tools to validate gene function in cells, as well as to implement the pipelines of recombinant protein production.

According to a further aspect of the invention, there is provided a method for increasing the protein synthesis efficiency of a target in a cell comprising administering the functional nucleic acid molecule or the composition described herein, to the cell. Preferably the cell is a mammalian cell, such as a human or a mouse cell.

Methods of the invention result in increased levels of target protein in a cell and therefore find use, for example, in methods of treatment for diseases which are associated with gene defects (i.e. reduced protein levels and/or loss-of-function mutations of the encoding gene). Methods of the invention find particular use in diseases caused by a quantitative decrease in the predetermined, normal protein level. Methods of the invention can be performed in vitro, ex vivo or in vivo.

It will be understood that the embodiments described herein may be applied to all aspects of the invention, i.e. the embodiment described for the functional nucleic acid molecules may equally apply to the claimed methods and so forth.

The invention will now be illustrated with reference to the following non-limiting examples.

EXAMPLES

Example 1—Materials and Methods

Cell Culture

Human Embryonic Kidney (HEK) 293T/17 cells, human hepatocellular carcinoma cells (HepG2) and mouse hepatocellular carcinoma cells (Hepa1-6) were obtained from ATCC and cultured in Dulbecco's modified Eagle's (DMEM) (1×)+GlutaMAX-1 supplemented with 10% fetal bovine serum and 1% Penicillin-Streptomycin at 37° C., 5% CO2.

Plasmid and Constructs

The pEGFP-C2 plasmid was purchased. The pCS2+_SINEUP-GFP plasmid was described in previous studies (e.g. see Carrieri et al. (2012) Nature 491 (7424): 454-457 and Toki et al. (2019) bioRxiv, 664029). The binding domain (BD) of the SINEUP targeting GFP, A5'-32 nt, has a deletion of 28 bases from the 5' end of the original 60 nucleotide (nt) SINEUP-GFP and corresponds to the mRNA positions-28 to +4 (see FIG. 1B in Takahashi et al. (2018) PLOS One 13, e0183229). The pcDNA3.1_EGFP plasmid was constructed by cloning a fragment encoding full-length EGFP (-40 bp to the stop codon) from the plasmid pEGFP-C2 into pcDNA3.1 (-). The SINEUP targeting mouse SOX9 (named miniSINEUP-SOX9) consists of a BD overlapping with mouse SOX9 mRNA in an antisense manner, or a control without the BD (named miniSINEUP-Random; Rd) containing a random sequence instead of the SOX9 binding domain, and an effector domain (ED) containing an inverted SINE B2 sequence from mouse AS-Uchl1 RNA (167 nt), cloned into a pCS2+vector (FIG. 6).

For Example 6, miniSINEUP-DJ1 (Zucchelli et al. (2015) Front. Cell Neurosci. 9:174) was excised from a pCS2 scaffold using XhoI and SnaBI and cloned downstream the T7 promoter in pCMV6 by using SalI and PmeI restriction sites to obtain pCMV6-miniSINEUP-DJ1. A miniSINEUP-DJ1 cloned into pCS2 (pCS2-miniSINEUP-DJ1) and the corresponding pCS2-empty vector were used as control DNA in RNA transfections experiments.

In Vitro Transcribed (IVT) RNAS

SINEUP RNAs were synthesized using mMESSAGE mMACHINE SP6 Transcription Kit and as modified from protocol described in Mandal & Rossi ((2013)

Nature Protocols 8:568-82) by using the following nucleotide modifications: CTP was replaced with 5-methylcytidine-5'-triphosphate (m5C), and UTP was replaced with pseudouridine-5'-triphosphate (ψ) or N1-methylpseudouridine-5'-triphosphate (N1mψ). Modified nucleotides were all from TriLink (final concentration, 7.5 mM). The regents were mixed with 40 ng/μL (final concentration) of linearized SINEUP plasmid. A poly A tail was added to the in vitro transcribed (IVT) RNAs using *E. coli* poly A polymerase (5000 U/mLat 37° C. for 30 minutes. Resulting modified in vitro transcribed (mIVT) RNAs were extracted by using RNeasy Mini kit.

For Example 6, unmodified and modified RNA molecules were transcribed in vitro using the Megascript T7 kit. Modified nucleotides triphosphates (2'-O-methyl-ATP, N6 methyl-ATP, Pseudouridine) were purchased. In vitro transcription reactions were assembled according to recommendation from the kit manufacturer and incubated overnight (16 hours) at 37° C. All transcripts were treated with DNAse I for 15 minutes at 37° C. and immediately purified using the RNeasy mini Kit. All transcripts were checked for purity and integrity by UV-vis spectrophotometry and denaturing polyacrylamide gel electrophoresis (PAGE).

Plasmid and RNA Transfection Conditions

HEK293T/17 cells were plated into 12-well plates ($1\times10^5$ cells/well), followed 24 hours later by transfection of plasmid or RNA (IVT, or mlVT). To detect EGFP, 1380 ng SINEUP-GFP plasmid or 720 ng (m) IVT SINEUP-GFP RNA was co-transfected with 300 ng pEGFP-C2 in each well by using Lipofectamine 2000 with A reduced-serum cell culture medium formulated to support cell viability and transfection efficiency under conditions of decreased serum supplementation (1×) Reduced Serum Medium. The cells were harvested at 24 hours after transfection. To detect endogenous SOX9, HEK293T/17 cells were plated into 12-well plates ($1\times10^5$ cells), followed 24 hours later by transfection of 2 μg miniSINEUP-SOX9 plasmid or 100 ng of mlVT miniSINEUP-SOX9 RNA per well. Cells were harvested at 24 and 48 hours after plasmid transfection and at 24 hours after mlVT transfection.

For Example 6, HEK293T/17 cells purchased by ATCC were cultured in DMEM high glucose (4.5 g/L D-glucose) with L-Glutamine, completed with 10% Fetal Bovine Serum and 1% Penicillin/Streptomycin antibiotics mix and 1% HEPES buffer. HEK293T/17 cells were passaged 1:5 to 1:10 and cell lines were used within passage number 10. RNA was transfected using Polyethylenimine (PEI) (MW 25000, branched) according to the following protocol. Cells were plated at a density of 250,000/well in a six-wells plate 24 hours before transfection, in DMEM complete. The day after, immediately before transfection, medium was replaced with 1 ml A reduced-serum cell culture medium formulated to support cell viability and transfection efficiency under conditions of decreased serum supplementation per well. A transfection mix was prepared, containing 400 ng of RNA in 160 μl of DMEM without serum and antibiotics, at room temperature. 2.5 μl of 40 UM PEI was added to the reaction, the tube was briefly vortexed for 1 second and incubated at room temperature for 10 minutes. The tube was vortexed again for 1 second and added to the cells. Cells were harvested at 48 hours for Western blot and RT-qPCR analyses. Finally, DNA control transfections were carried out in parallel using 1 μg of plasmid DNA (pCS2-miniSINEUP-DJ1 or pCS2 empty) and 3 μl of Lipofectamine 2000 in 200 μl of A reduced-serum cell culture medium formulated to support cell viability and transfection efficiency under conditions of decreased serum supplementation. In this case, transfection medium was changed 6 hours after transfection and replaced with 2 ml of DMEM complete per well. Cells were harvested at 48 hours.

Western Blotting (WB)

Transfected cells were lysed with Cell Lysis buffer and incubated at 4° C. for 1 hour. Cell lysates were applied to a 10% precast polyacrylamide gel, separated by SDS-PAGE, and transferred to a nitrocellulose membrane. All primary and secondary antibodies were used at 1:1000 dilution. To detect EGFP, anti-GFP rabbit polyclonal and anti-GFP mouse monoclonal (clone JL-8) antibodies for RRL cell-free system were used.

For endogenous SOX9 detection, rabbit monoclonal anti-SOX9 antibody (clone EPR14335,) was used. To detect DJ1, anti-DJ1 mouse monoclonal antibody was used. The membranes were incubated with primary antibodies at 4° C. overnight, followed by incubation for 45 minutes at room temperature with secondary anti-rabbit IgG conjugated with HRP. Bands were visualized by ECL Detection Reagent. As a control, primary anti-β actin mouse monoclonal antibody was used as primary antibody and anti-mouse IgG conjugated HRP was used as secondary antibody. Bands were detected using a gel imaging system and associated analysis software configured for chemiluminescent signal acquisition and quantitative analysis.

For Example 6, cell pellets were lysed in lysis buffer (PBS+1% of a nonionic surfactant detergent) with complete protease inhibitor on ice, briefly sonicated on ice and centrifuged at maximum speed for 20 minutes at 4° C. Supernatants containing total lysates were collected on ice and quantified for total protein contents using BCA assay kit. 10 μg of total lysate were loaded onto a pre-cast polyacrylamide gel (approximately 10% acrylamide, about 1.5 mm thickness, with multiple sample wells) and run at 120 V for approximately 90 minutes for SDS-PAGE. Gels were transferred to a 0.2 μm nitrocellulose membrane at 250 mA for 90 minutes. DJ1 was detected with mouse anti-DJ1 primary antibody and actin was detected with rabbit anti-B-actin primary antibody, both diluted 1:8000 in 5% BSA in tris-buffered saline-Tween-20 (TBST) and incubated overnight at 4° C. Horse-radish peroxidase conjugated secondary anti-mouse and anti-rabbit antibodies were diluted 1:10000 and incubated at room temperature for one hour. Signals were detected with Pierce ECL plus detection reagent and read on a gel imaging system configured to detect and capture signals from stained or labeled biomolecules, including chemiluminescent, fluorescent, or colorimetric emissions. Band intensities were calculated using image acquisition and processing software configured for quantitative analysis of gel-based and blot-based signals.

RNA Extraction and Quantification

Total RNA was extracted using RNeasy mini kit, followed by DNase I treatment (TURBO DNA-free Kit, Invitrogen). The cDNA was synthesized using PrimeScript 1st strand cDNA synthesis kit, and quantitative real-time PCR (qPCR) analysis was performed with a premixed polymerase chain reaction (PCR) reagent comprising a thermostable DNA polymerase, deoxynucleotide triphosphates, buffer components, and additives to facilitate nucleic acid amplification in a Fast Real-Time PCR System. Thermal conditions consisted of an initial 30 seconds at 95° C., 40 cycles of 95° C. for 5 seconds and 60° C. for 30 seconds, followed by melting curve drawing steps.

For Example 6, total RNA was extracted using RNeasy mini kit, then samples were quantified by UV-vis spectrophotometry. DNAse digestion was then performed adding 1 μl Turbo DNAseI and 1 μl of 10×DNAseI buffer to 800 ng of RNA in a 10 μl reaction and incubating for 15 minutes at room temperature. DNAse was inactivated by adding 1 μl of DNAseI stop solution and incubating for 10 minutes at 70° C. 5 μl of DNAse-treated RNA (approximately 400 ng) was retrotranscribed using a kit for synthesizing complementary DNA (cDNA) from RNA templates comprising a reverse transcriptase enzyme, primers, nucleotides, and reaction buffers suitable for reverse transcription according to instructions from the manufacturer, in a 20 μl reaction. RT-qPCR reactions were then set-up including 2 μl of cDNA, 5 μl of a PCR supermix comprising a thermostable DNA polymerase, deoxynucleotide triphosphates, buffering agents, and a fluorescent DNA-binding dye were used for nucleic acid amplification and detection, 0.4 μl of forward primer and 0.4 μl of reverse primer, in a total volume of 10 μl. RT-qPCR was run on a CFX96 Touch Real-Time PCR Detection System. Glyceraldehyde 3-phosphate dehydrogenase (GAPDH) gene was used as an internal reference to normalize the results.

RNA FISH (RNA Fluorescence in situ Hybridization)

RNA FISH was performed as previously described in Toki et al. (2019) bioRxiv, 664029. Briefly, cells were fixed with 4% paraformaldehyde followed by permeabilization with a nonionic surfactant detergent at room temperature for 5 minutes. RNA was hybridized with fluorescently labelled FISH probes and incubated overnight at 37° C. Cells were washed and imaged by using a confocal microscope.

Cell-Free Translation System

Rabbit reticulocyte lysate (RRL) and human cell lysate of Hela cells were purchased. In vitro translation was performed following the manufacturer's protocol. Briefly, for each reaction, 400 ng of SINEUP plasmids or 200 ng of (m) IVT SINEUP RNA was mixed with 120 ng of pcDNA3.1_EGFP. The mixture was incubated for 90 minutes at 30° C. Protein expression was measured by Western blotting assay as previously described.

RNA Extraction of Chemically Modified In-Cell Transcribed (mICT) SINEUP-GFP

HEK293T/17 cells were plated into a 10 cm dish and SINEUP-GFP plasmids were transfected after 24 hours and $2\times10^7$ cells were harvested by Trizol/chloroform extraction. Total RNAs contained SINEUP-GFP RNAs at the aqueous phase were extracted by RNeasy mini kit.

Pull Down of In-Cell Transcribed SINEUP-GFP RNAS

The eluent of total RNAs containing mICT SINEUP-GFP RNAs were adjusted up to 100 μL with lysis buffer and mixed with two volume of Hybridization buffer. For $2\times10^7$ cells, 100 μmol SINEUP-GFP probes were added and incubated at 37° C. overnight with agitation. After the probe hybridization to SINEUP-GFP RNAs, 100 UL of Tamavidin was added to the sample, and incubated at 37° C. for 30 minutes and washed 4 times with washing buffer. After removing all excess supernatant, the beads were resuspended with 100 μL of proteinase K buffer without proteinase K and incubated at 65° C. for 5 minutes with agitation. SINEUP-GFP RNAs were extracted by Trizol/chloroform and purified by RNeasy mini kit following the manufacturer's instructions. Pull-down extractions were repeated twice and the SINEUP-GFP RNAs were dissolved in the water.

Library Preparation of Oxford Nanopore Direct-RNA Sequencing

Both IVT (modified and unmodified) and mICT direct SINEUP-GFP RNA-seq libraries were prepared with SQK-RNA002 kit by following the manufacturer's protocol. The original reverse transcription adapter (RTA) and four barcoded RTA, which are described in Leger et al., 2019, bioRxiv (doi.org/10.1101/843136), were used for (m) IVT and mICT SINEUP-GFP RNAS respectively. The libraries were applied to Mk1C sequencer and sequenced for 72 hours.

Analysis of Oxford Nanopore Direct-RNA Sequencing

The sequencing data was processed by the methods published in Leger et al., 2019, bioRxiv (doi: doi.org/10.1101/843136). In brief, raw fast5 reads from direct-RNA seq were basecalled with Guppy. Nanocompore was used for each of the unmodified IVT SINEUP-GFP, 20% w mIVT SINEUP-GFP and mICT SINEUP-GFP. The output was first filtered to remove positions with a p-value of greater than 0.01 and an absolute log odds ratio (absLOR) of less than one (i.e. any value between-1 and +1). An absLOR of less than 1 would indicate that the position in question has a similar likelihood of being either modified or non-modified. A peak calling script was then called on the remaining positions to further filter the large number of modified positions found.

m6A RNA Immunoprecipitation

HEK293T, A549 ShCtrl or A549 ShMETTL3/2 cells were transfected with miniSINEUP-DJ1 as described above. 48 hours post-transfection, cells were washed twice with PBS and trypsinized to detach. Cell pellets were washed again once with PBS and total RNA was extracted with RNeasy mini kit following the manufacturer's protocol. All samples were subject to DNAse I treatment during extraction.

25 μg of total RNA was diluted to a final volume of 200 μL with IPP buffer (10 mM Tris-HCl pH 7.4, 150 mM NaCl, 0.1% of a neutral detergent) containing 2.5 μg of anti-m6A antibody and incubated on a rotating wheel at 4° C. for 2 hrs. The mixture was then immunoprecipitated incubating with 15 μL of magnetic beads functionalized with an affinity ligand for additional 2 hrs. Beads were then washed 5 times with IPP buffer and resuspended in 500 μL of a monophasic reagent comprising phenol and guanidine salts.

RNA was extracted according to manufacturer protocol and analyzed by qRT-PCR. IgG-coupled-beads and beads only samples were used as negative controls.

m6A RT-qPCR

Total RNA was extracted from cells 48 hrs post-transfection using RNA mini kit. All samples were subjected to DNAse I treatment during extraction.

For m6A-retrotranscription reaction, the protocol was adapted from Castellanos-Rubio et al. Briefly, 100 ng RNA, 100 nM of each primer, 50 UM dNTPs and 0.1 U Bstl or 0.8 U of MVL-MRT were used. Thermal cycler was set for 15 min at 50° C., 85° C. for 3 min, 4° C. ~. 1 μL of the retrotranscription reaction was used together with 100 nM of each primer and 2×iTaq SYBR green. Reactions were run on a CFX96 Real time PCR System and melting curves were analyzed to ensure the amplification of a single product.

Example 2

Figure 1:
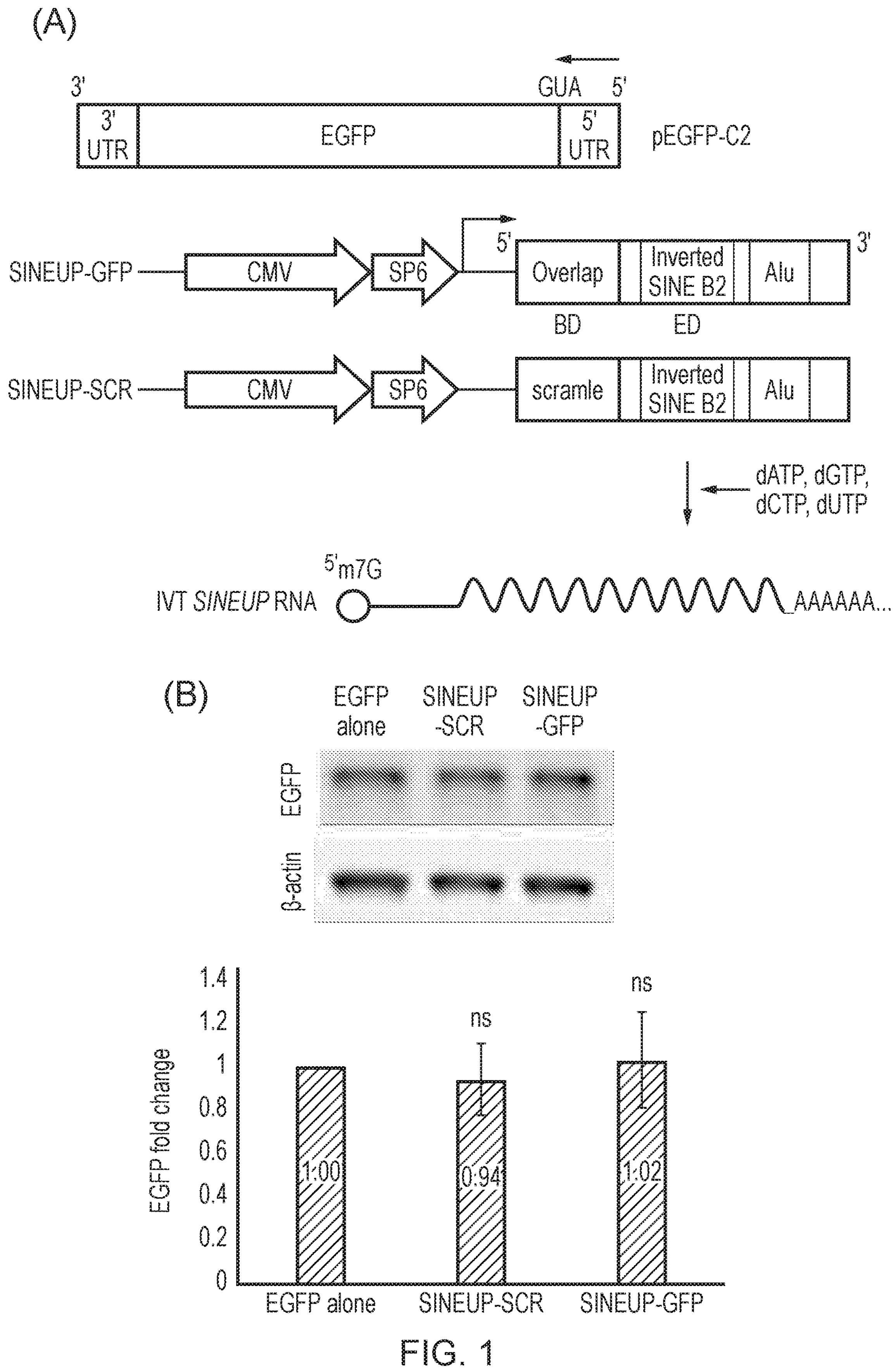
FIG. 1: Transfection of in vitro transcribed SINEUPs RNA in HEK293T/17 cells. (A) Schematic representation of the SINEUP constructs. SINEUP-GFP contains the overlapping region with EGFP mRNA as a binding domain (BD) and inverted SINEB2 element as an effector domain (ED). SINEUP-SCR contains a scrambled sequence replaced from the BD of SINEUP-GFP. (B) Translational up-regulation of EGFP by co-transfection of EGFP plasmid and IVT SINEUPs. Western blot image shows representative images of the effect of IVT SINEUPs on the EGFP level detected by using an anti-GFP rabbit polyclonal antibody. Data are shown as means+S.D. of at least 3 independent experiments, ns: not significant (two-tailed Student's t-test). (C) Quantification of the EGFP mRNA and the IVT SINEUP RNA levels following co-transfection with EGFP plasmid and IVT SINEUPs. ns: not significant (two-tailed Student's t-test). Data are shown as means±S.D. from at least 3 independent experiments.
Figure 1:
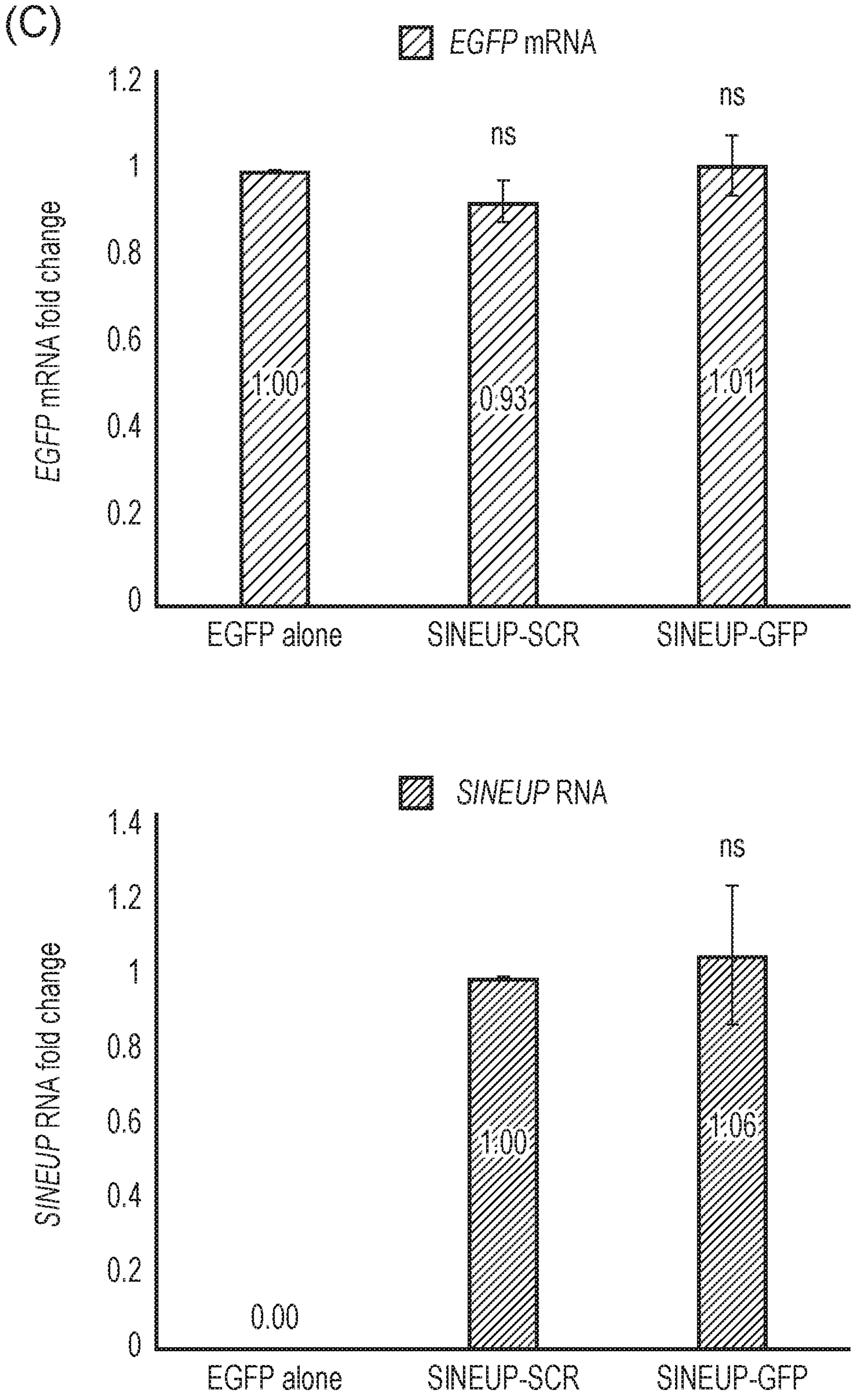

This Example shows that transfecting naked in vitro transcribed (IVT) SINEUP RNA showed negligible stimulation of protein synthesis. Previously, it was found that co-localization of target mRNAs and SINEUP RNAs in the cytoplasm was one of the key requirements for up-regulation of target mRNA translation (Toki et al. (2019) bioRxiv, 664029). The inventors hypothesized that direct transfection of IVT SINEUP RNAs into the cytoplasm would more efficiently enhance protein production than SINEUP plasmid transfection, which requires export of RNA transcribed in the nuclei. To investigate the efficiency of translational up-regulation using IVT SINEUPs, IVT RNAs were transfected into HEK 293T/17 cells with EGFP plasmids as a target sense transcript. IVT SINEUP-GFP RNA contains a binding domain (BD) designed to target EGFP mRNA (FIG. 1A), while IVT SINEUP-SCR RNA was designed as a negative control and contains a scrambled EGFP BD. Contrary to the hypothesis, IVT SINEUP-GFP did not stimulate translation of EGFP (FIG. 1B) although, consistent with previous studies, the RNA level of EGFP mRNAs and SINEUPs did not change among the cells (FIG. 1C). These findings were also confirmed by transfection of IVT miniSINEUP-DJ1 which contains a BD designed to target the mRNA of PARK-DJ1 (a gene found mutated in familial forms of Parkinson's Disease) into 293T/17 cells. MiniSINEUP-DJ1 did not cause any significant change in the endogenous levels of DJ-1 protein, regardless of the capping or polyadenylation status of the SINEUP RNA (data not shown).

To elucidate the subcellular distribution of IVT SINEUP RNAs, RNA FISH (fluorescence in situ hybridization) was performed, which revealed that most of the IVT SINEUP RNAs aggregated as intense spots within cells, or it was difficult to detect IVT SINEUP RNAs at all. This suggested that IVT SINEUP RNAs were partially degraded immediately after transfection, detected as fragmented RNAs or were not present in sufficient quantities to adequately co-localize with EGFP mRNA. Consequently, EGFP translation was not up-regulated.

Example 3

Figure 2:
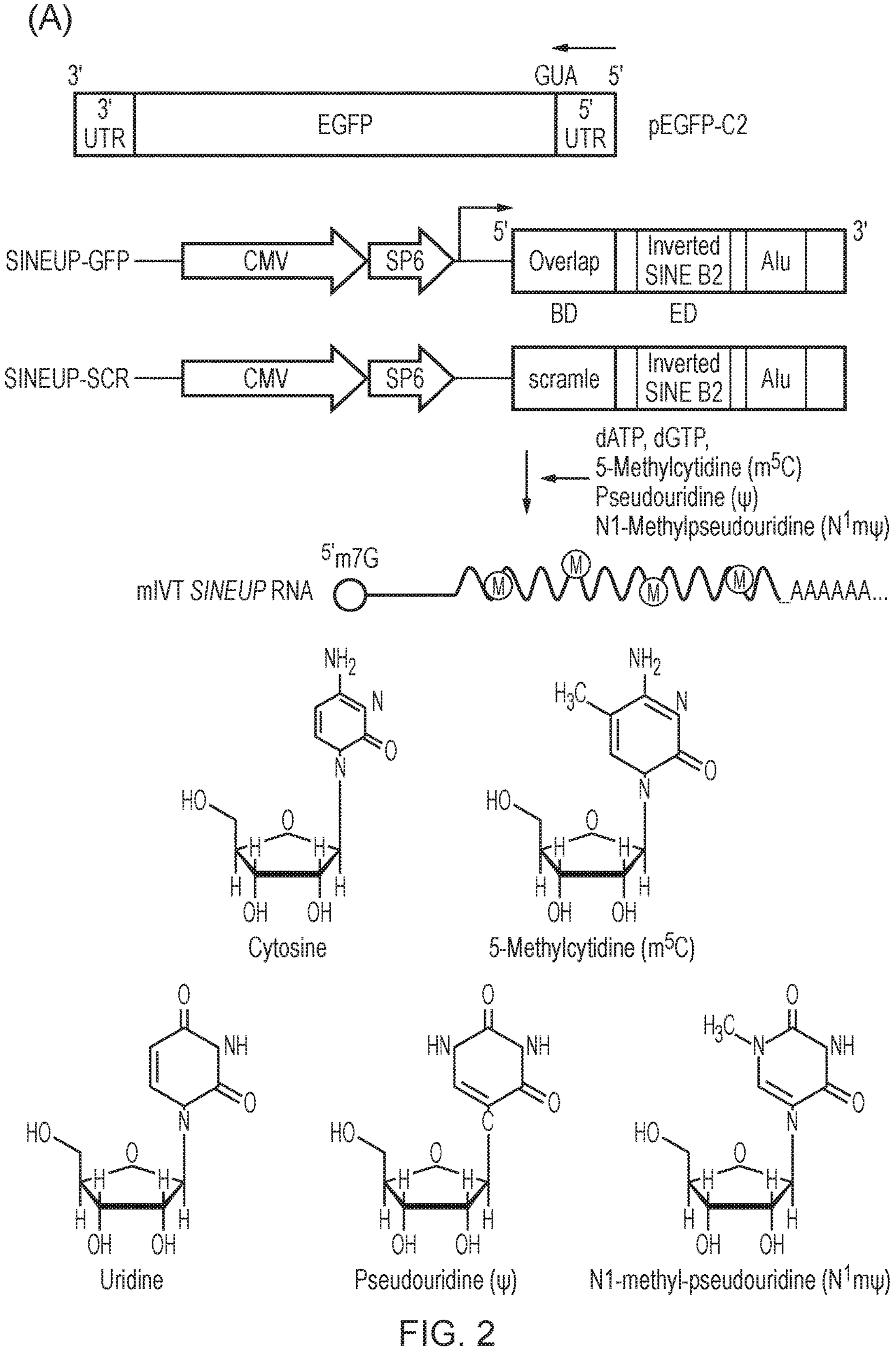
FIG. 2: Transfection of in vitro transcribed SINEUP-GFP RNA with chemically modified nucleotides in HEK293T/17 cells. (A) Schematic representation of nucleotide-modified SINEUPs. The nucleotides dCTP, dUTP were replaced with 5-Methylcytidine-5'-Triphosphate (m5C), and Pseudouridine-5'-Triphosphate (ψ) or N1-Methylpseudouridine-5'-Triphosphate (N1mψ), respectively. (B) Translational up-regulation of EGFP by co-transfection of EGFP plasmid and mIVT SINEUPs. Western blot images show representative images of the effect of mIVT SINEUPs on the EGFP level detected by using an anti-GFP rabbit polyclonal antibody. Up-regulation of EGFP levels was measured from at least three independent experiments. Data are shown as means±S.D. ** $p<0.01$, *$p<0.05$, ns: not significant (two-tailed Student's t-test). (C) Quantification of the EGFP mRNA and the mIVT SINEUP RNA levels following co-transfection with EGFP plasmid and mIVT SINEUPs. ns: not significant (two-tailed Student's t-test). Data are shown as means±SD from at least 3 independent experiments.
Figure 2:
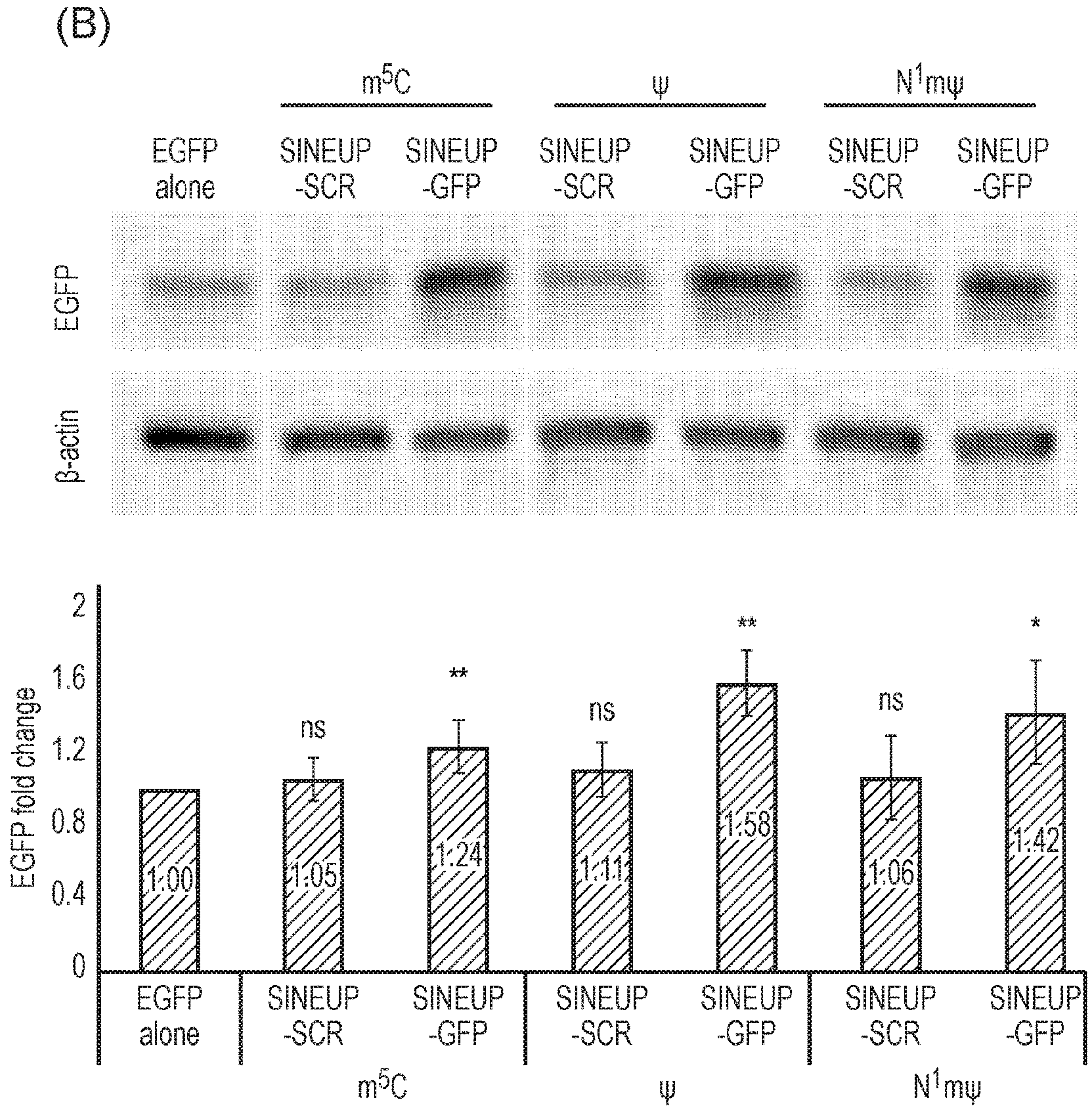
Figure 2:
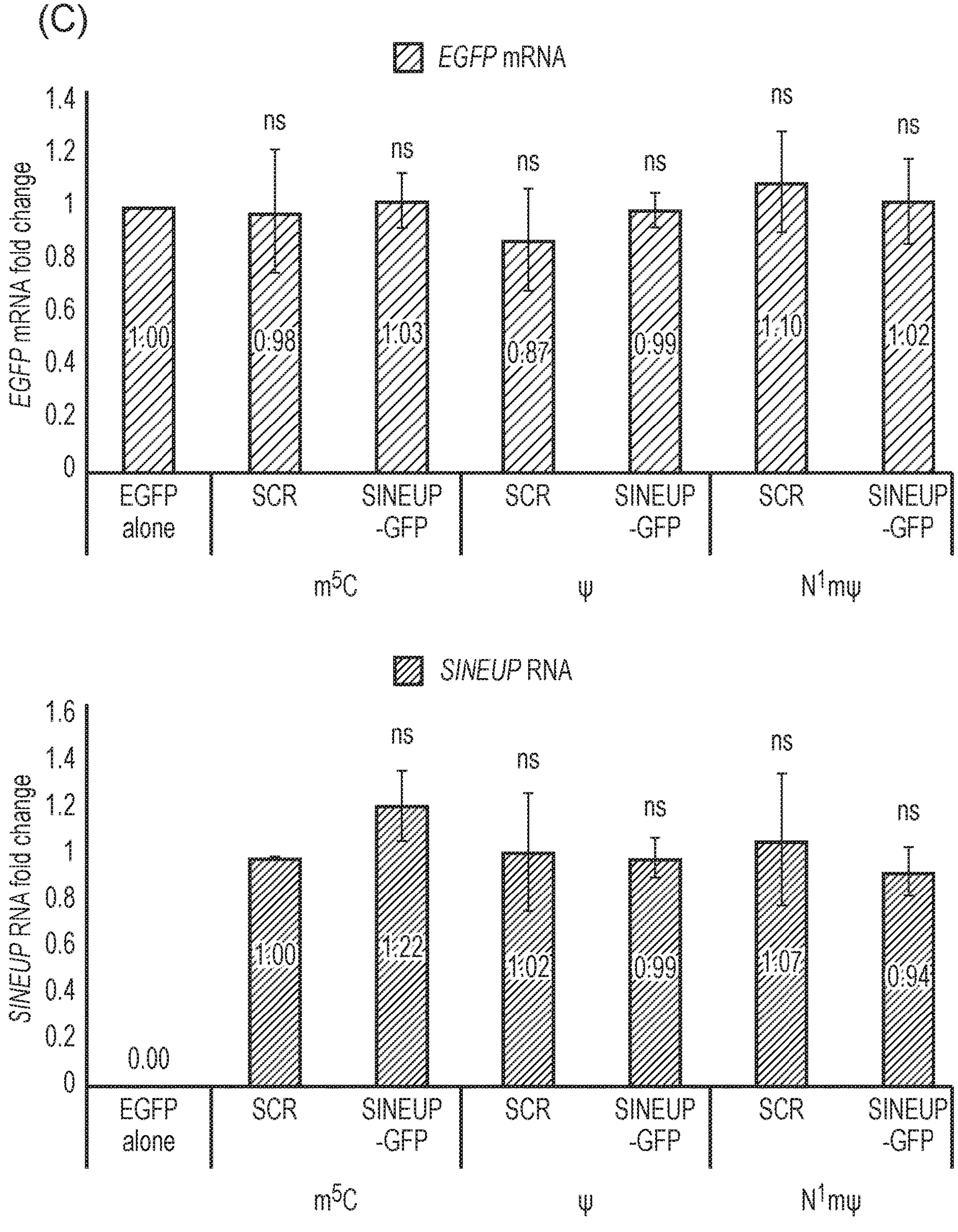
Figure 3:
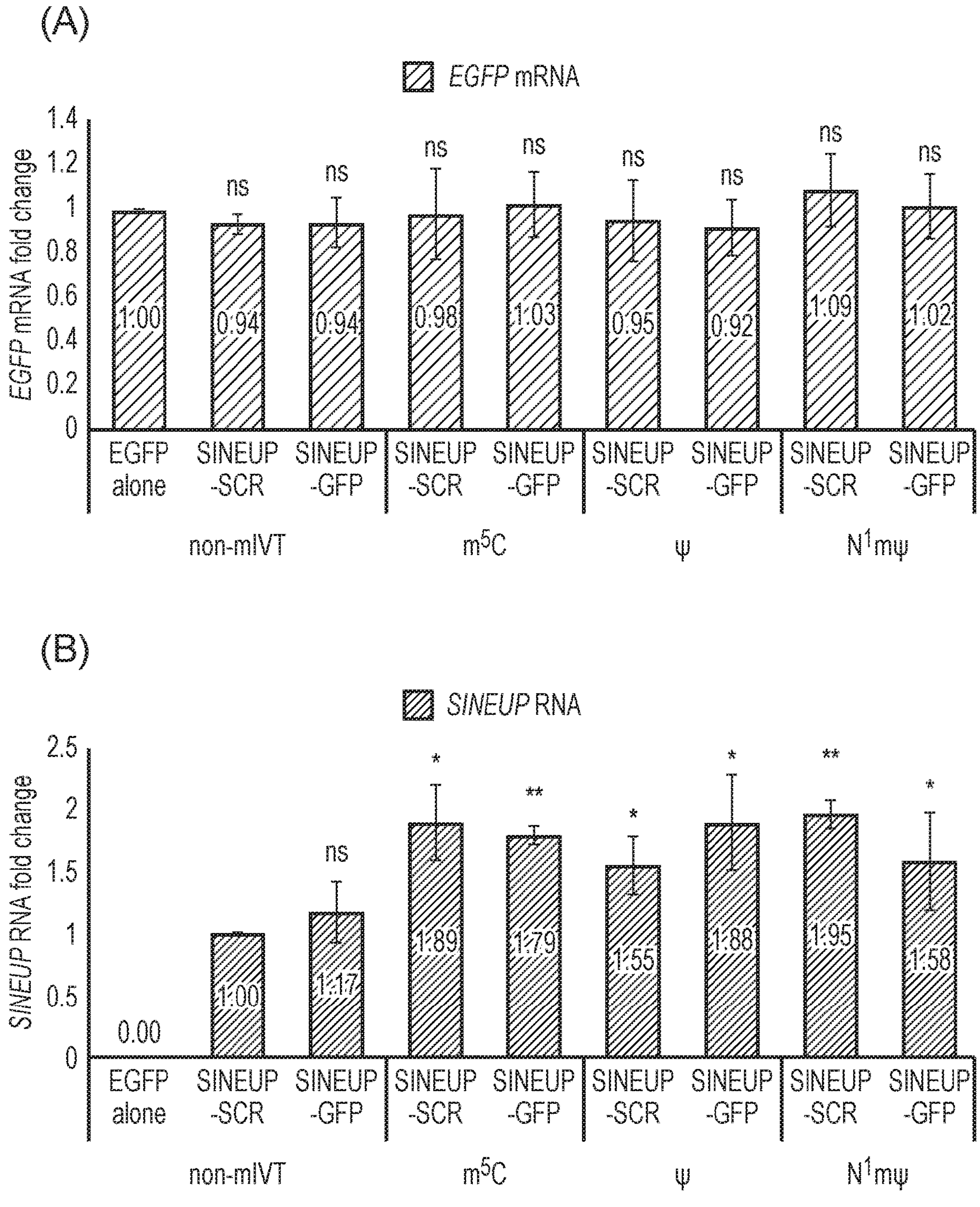
FIG. 3: (A) Quantification of the EGFP mRNA levels following co-transfection with pEGFP-C2 plasmid and each transcribed SINEUP. ns: not significant (two-tailed Student's t-test). Data are shown as means+S.D. from at least 3 independent experiments. (B) Quantification of the SINEUP RNA levels following co-transfection with EGFP vector and each transcribed SINEUP. ** $p<0.01$; * $p<0.05$; ns: not significant (two-tailed Student's t-test). Data are shown as means±S.D. from at least 3 independent experiments.

This Example shows that in vitro transcribed (IVT) SINEUP RNAs need to be stabilized with nucleotide modifications in the cells. RNA FISH experiments showed that non-modified IVT SINEUPs were likely aggregated after transfection into the cells. Chemically modified IVT (mIVT) SINEUP RNAs containing m5C, ψ and N1mψ modifications were prepared, and transfected directly with EGFP plasmid into HEK293T/17 cells (FIG. 2A). EGFP up-regulation and subcellular distribution of mIVT SINEUP RNAs was examined. All mIVT SINEUPs showed the characteristic up-regulation of EGFP compared to the control (EGFP alone; FIG. 2B), without affecting EGFP mRNA levels (FIG. 2C, FIG. 3A). Previously, it was found that SINEUP-GFP RNAs transcribed from a DNA plasmid localized both in the nucleus and the cytoplasm when EGFP and SINEUP-GFP plasmid were co-transfected. However, this data shows mIVT SINEUP-GFP localized in the cytoplasm regardless of EGFP plasmid transfection (indicated by RNA FISH images, data not shown). Consistent with this, up-regulation of EGFP mRNA translation did not significantly affect EGFP mRNA levels among the cells (FIG. 2C, FIG. 3A). Notably, the RNA level of mIVT SINEUPs were more than 1.5-fold greater than non-modified IVT SINEUP RNAS (FIG. 3B) implying that these modified nucleotides contributed not only to EGFP up-regulation, but also the stabilization of SINEUPs in the cells.

Example 4

Cell-free translation systems were used to observe SINEUP up-regulation activity separately from RNA stabilization. None of the SINEUP RNAs tested up-regulated EGFP in RRL, whereas mIVT SINEUPs with ψ and N1mψ)-up-regulated EGFP in HeLa cell lysate (data not shown). This result suggests that modified nucleotides contribute to the up-regulation of EGFP in a cell-free system, and are therefore not just required from RNA stabilistation. This also implies that the expression of cellular components is important for SINEUP activity.

Example 5

Figure 4:
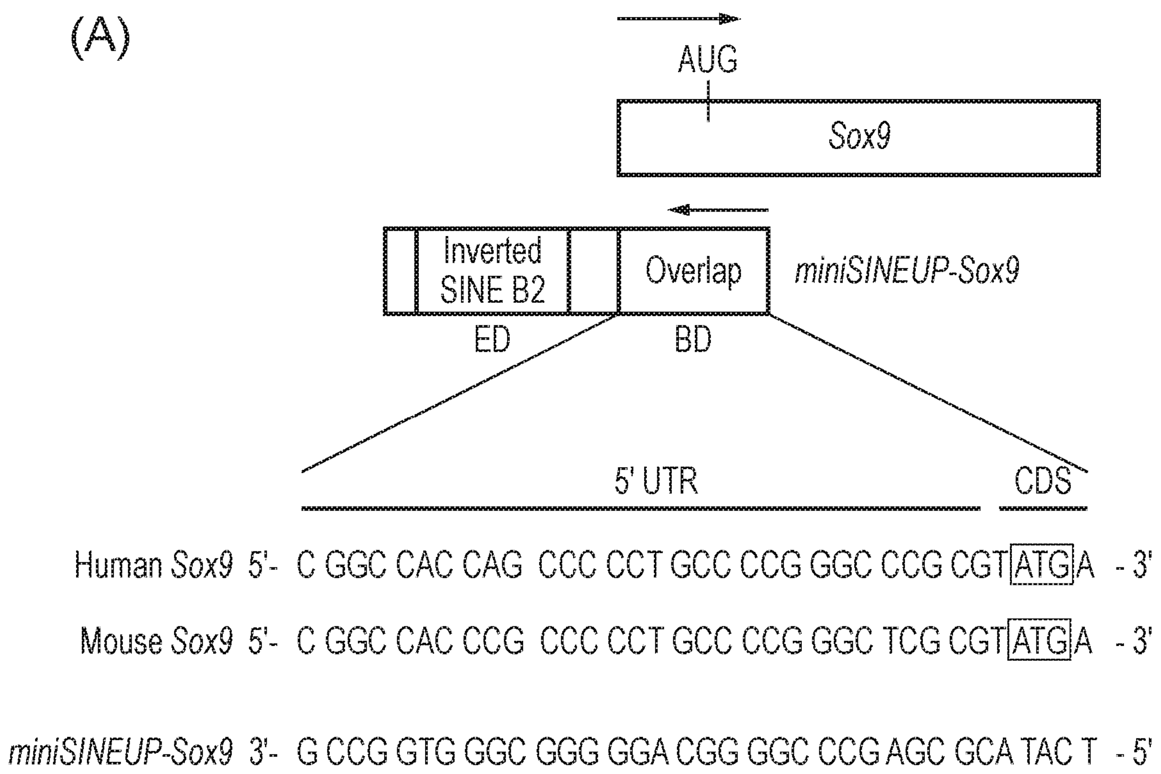
FIG. 4: miniSINEUP-SOX9 for endogenous target transfected into HepG2 and Hepa 1-6 cells. (A) Schematic representation of the miniSINEUP-SOX9 constructs-Human Sox9 (SEQ ID NO: 51), Mouse Sox9 (SEQ ID NO: 52), and miniSINEUP-Sox9 (SEQ ID NO: 53). The miniSINEUP-SOX9 contains the overlapping region with SOX9 mRNA as a binding domain (BD) and inverted SINE B2 from AS-Uchl1 RNA as an effector domain (ED). (B)
Figure 4:
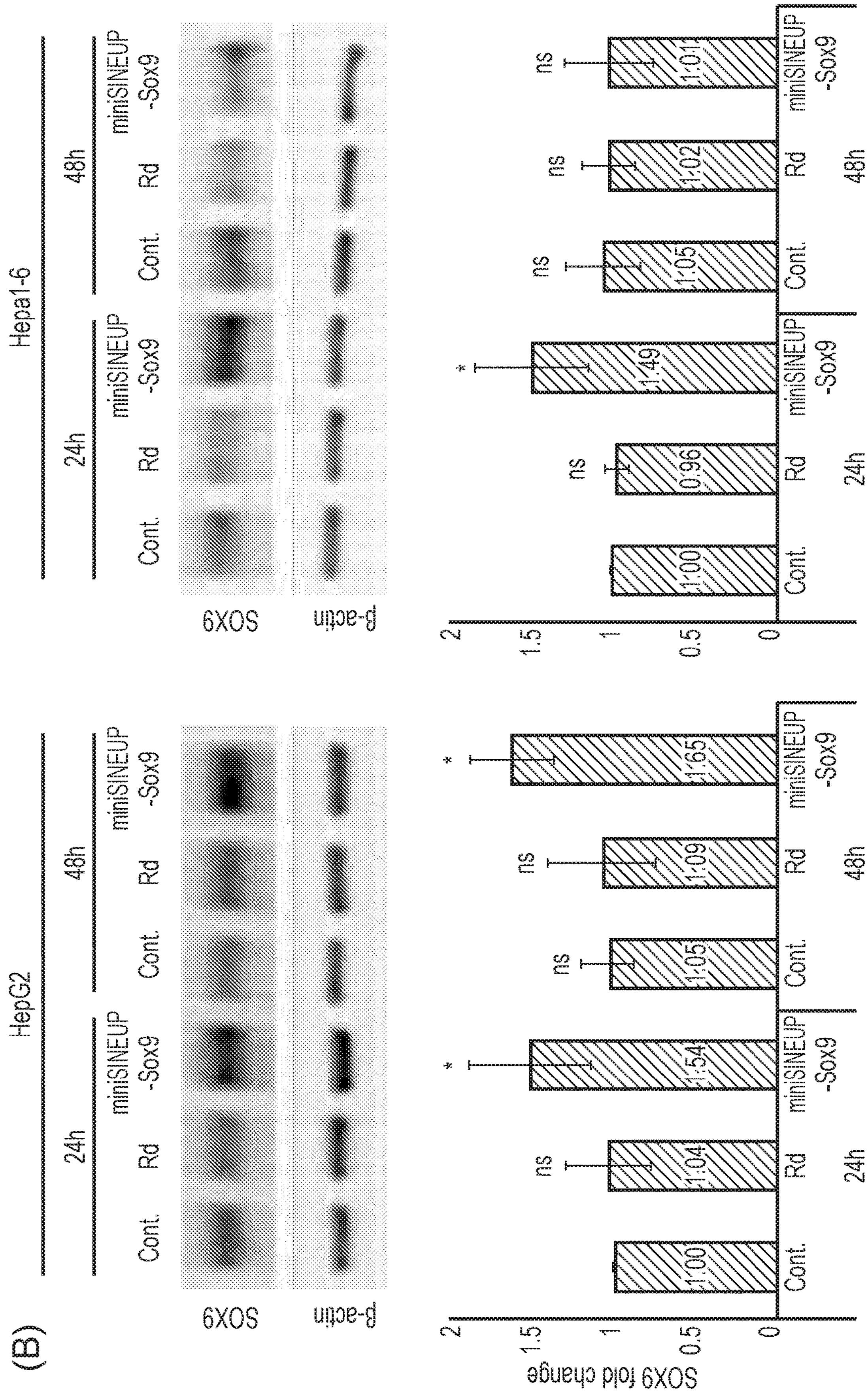
Figure 4:
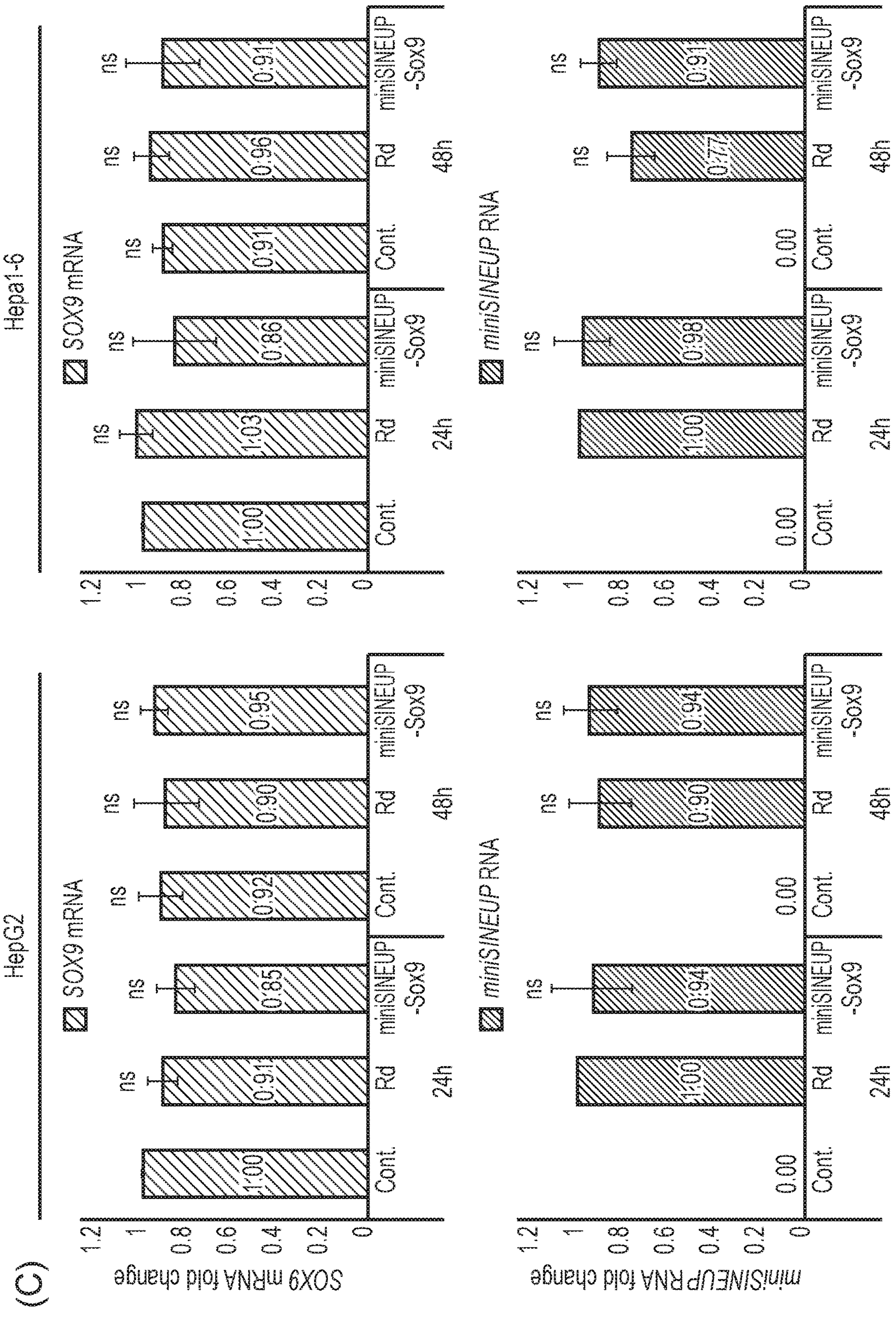

This Example shows that mIVT SINEUPs can be used to enhance endogenous target protein production. To test whether SINEUPs can increase production of endogenous target proteins, a SINEUP directed to SOX9 was developed. SOX9, sex-determining region Y (SRY)-box 9 (SOX9), is a transcription factor regulating cell differentiations, development and gene expression in several tissues and organs in vertebrates. In addition, SOX9-positive cells in adult liver have been shown to regenerate as hepatocytes after injury. The ultimate goal for SINEUPs is to use them for therapeutic applications, and for this a smaller sized functional SINEUP is desirable. A miniSINEUP-SOX9 plasmid containing a BD (−31/+4) overlapping the mouse SOX9 mRNA or miniSINEUP-Rd plasmid containing a random sequence, non-binding domain instead of the Sox9 binding domain, and an inverted SINE B2 ED from AS-Uchl1 RNA (FIG. 4A) was designed and transfected into human and mouse hepatocyte carcinoma cell lines (HepG2 and Hepa 1-6) to examine any enhancement of SOX9 protein production. Cells transfected with the miniSINEUP-SOX9 plasmid showed an approximate 1.5-fold up-regulation of SOX9 protein compared to the control (no SINEUPs) in HepG2 cells both 24 hours and 48 hours post-transfection, and in Hepa 1-6 cells 24 hours post-transfection (FIG. 4B). Consistent with previous studies targeting EGFP mRNA, endogenous target SOX9 mRNA levels did not change in the SINEUP transfected cells (FIG. 4C). This shows that miniSINEUP-SOX9 can effectively enhance protein levels of endogenous targets such as SOX9.

The efficiency of translation up-regulation when using mlVT miniSINEUP-SOX9, which contains m5C, ψ and N1mψ(FIG. 5A), was also tested in HepG2 cells. The mlVT miniSINEUP-SOX9 with ψ and N1mψalso showed around 1.5-fold up-regulation of SOX9 protein compared to the control without transfection of mlVT miniSINEUPs (FIG. 5B). Consistent with the plasmid transfection, the endogenous SOX9 mRNA level did not change among the cells transfected with mlVT miniSINEUP RNAs (FIG. 5C). This implies that nucleotide modifications might contribute to stabilization of miniSINEUP-SOX9 to enhance SOX9 protein level in culture cell.

Example 6

This Example shows that different combinations of modifications are suitable to preserve the functionality of miniSINEUP-DJ1. In order to further study the functionality of modified and unmodified in vitro transcribed SINEUPs, a model SINEUP named miniSINEUP-DJ1 which targets PARK7-DJ1 (a gene found mutated in familial forms of Parkinson's Disease (PD)) was used. MiniSINEUP-DJ1 was transcribed in vitro using modified or unmodified nucleotides and the different transcripts were transfected into 293T/17 cells in equimolar amounts. Unmodified in vitro transcripts were compared to transcripts including a few natural modifications, namely 2'-O-methyladenosine (Am), N6-methyladenosine (m6A), Pseudouridine (ip) and various combinations thereof. Note that, as a consequence of the different kinetic of incorporation of nucleotides bearing different modifications, the composition of the IVT mix does not necessarily reflect the percentage of modifications found in the final molecule. In the case of Am and m6A, the latter was incorporated by the T7 RNA polymerase several fold more efficiently than the former. For convenience, the composition of the reaction mix is reported.

FIG. 7 shows DJ1 fold change from Western blot quantification of at least 3 different experiments for cells transfected with miniSINEUP RNA carrying different modifications or with control miniSINEUP plasmid. As shown in FIG. 7, while unmodified transcripts did not show SINEUP activity, the best combinations of modifications to preserve and optimize SINEUP activity were three, namely: i) Am 100%; ii) Am 99%+m6A 1%; iii) m6A 100%+ψ 100%. As a positive control to RNA transfection, plasmid DNA coding for the same miniSINEUP was also transfected in parallel, and SINEUP activity assessed by Western blot (FIG. 7B).

Reverse-transcription quantitative PCR (RT-qPCR) on total RNA extracts from cells transfected with unmodified and modified transcripts was performed in order to investigate the stability of the transfected RNAs at the end-point of the experiment (48 hours). Initial experiments revealed that retrotranscription is severely slowed down by the presence of the modifications used in this study. However, the differences between unmodified and modified RNAs was still shown to be more marked in the latter. This discrepancy may reasonably be attributed to different stability of unmodified and modified RNAs at 48 hours post-transfection. To investigate this further, a time course was performed in which unmodified and modified IVT miniSINEUP RNAs were transfected in equimolar amounts and cells harvested at different time points (6, 18 and 48 hours after transfection). Total RNA extracts were analysed by RT-qPCR and showed that stability of unmodified transcripts drops to less than 50% at 48 hours after transfection (FIG. 8A). In contrast, in the presence of certain combinations of modifications, stability is slightly improved. This is particularly evident in the presence of the combination of m6A and w. The ratio between RT-qPCR on RNA extracts from transfected cells and RT-qPCR on RNA extracts from non-transfected cells spiked with the IVT RNAs gives a calculated "stabilization fold", shown in FIG. 8B, which varies between 2 and 20 fold, depending on the mix of modifications. This implicates that impaired activity of unmodified IVT SINEUPs is due, at least in part, to its decreased stability due to the susceptibility to the action of intracellular nucleases.

Example 7

This Example shows that the content of modifications in the IVT SINEUP RNA can affect functionality and the structure-activity relationship of modified IVT SINEUP RNA. As noted above, due to the different kinetic of incorporation of nucleotides bearing different modifications, the composition of the IVT mix does not necessarily reflect the percentage of modifications found in the final molecule. Therefore, better to characterize the content of modifications in the IVT miniSINEUP RNA containing Am and m6A competing for the same sites, mass spectrometry analysis of these transcripts was performed. It was found that, when using a ratio of Am to m6A of 99:1 in the IVT reaction mixture, the relative abundance of the two modifications in the final molecule is only 20:80 (FIG. 9A, left bar). Of note, IVT SINEUP-DJ1 RNAs containing lower ratios of Am to m6A were not functional, indicating that a threshold level of Am is needed for the activity of this SINEUP (data not shown).

Circular dichroism (CD) spectroscopy was employed as a tool to compare the conformations adopted in solution by the SINEUP RNA molecules under investigation and to evaluate the possible role played by the structure on SINEUP activity (FIGS. 9B and 9C). While the complex and varied 3D conformations adoptable by RNA make the identification of each secondary structure highly challenging, CD spectra in the range of 200 nm to 320 nm is extremely sensitive in offering an overall understanding of nucleic acid folding (Circular Dichroism Spectroscopy of Nucleic Acids (2021) *In Comprehensive Chiroptical Spectroscopy*, pp 575-586; Sosnick, T. R., (2001) *Curr Protoc Nucleic Acid Chem*, Chapter 11, Unit 11 5).

The unmodified SINEUP sequence showed the typical CD profile of an A-form RNA (Kypr, J. et al. (2009) *Nucleic acids research,* 37 (6): 1713-25); a maximum around 265 nm indicates the presence of right-handed helices, and a minimum at 210 nm suggests an 8 parallel orientation of the double-stranded regions. Comparable spectra were recorded for the RNA sequences comprising the m6A base alone. However, when m6A was present in combination with the Am modification on the ribose, a decrement in the intensity of both maximum and minimum compared to the unmodified miniSINEUP was evident, hinting at a possible contribution of other conformational arrangements (FIG. 9B). Noticeably, this decrement was more marked when the ratio of Am to m6A increased. The spectra of transcripts containing the "active" Am to m6A ratio of 20:80 showed a decrease in the 265 nm peak of 41% compared to the spectrum of transcripts containing m6A alone, while the spectra of transcripts containing the inactive ratio of 3:97 showed a decrease in the same peak of only 9.7%. Thus, the increased percentage of Am from 3% to 20%, as measured by mass spectrometry (FIG. 9B), was reflected by a CD spectrum that differed more markedly from that of the IVT RNA fully modified with m6A (inactive) and resembled that of the RNA fully modified with Am (active; see FIG. 9D). Strikingly, the fully Am modified sequence and the one containing m6A in combination with ip showed almost identical CD spectra, which markedly differed from that of the unmodified RNA (FIG. 9B). Such modified molecules share similar functionality, despite bearing different modifications. Their spectra were characterized by a broader, less intense maximum in the 270 nm-280 nm area and a minimum of comparable intensity at 245 nm, indicating spectral features similar to that of the B-form DNA Sekine, M. et al. (2011) *Org Biomol Chem,* 9 (1): 210-8), rather than the A-form, typical of RNA (Werner, D. et al. (1998) *Pharmaceutica Acta Helvetiae,* 73 (1), 3-10; Szabat, M. et al. (2015) PloS one, 10 (11), e0143354).

Noticeably, the spectrum of the IVT RNA containing m6A and ψ (functional) was very different from both the one containing m6A alone and that containing ψ alone (both not functional). Indeed, the spectrum of the miniSINEUP containing m6A was very similar to that of the unmodified RNA. On the contrary, the spectrum of the RNA fully modified with ψ reflected the distortion of the helix attributable to this particular nucleotide (Kierzek, E. et al. (2013) *Nucleic acids research,* 42 (5), 3492-3501; Sumita, M. et al. (2005) *RNA* (New York, N. Y.), 11 (9), 1420-9), with a pronounced negative band at 210 nm, a 0 at around 235 nm and a weak maximum that covers the region spanning between 240 nm and 237 nm. This spectrum cannot be associated to a singular conformation but rather is the overlap of several signals derived by the w-associated alterations on the most common conformations. This data therefore shows that the content of modifications in the IVT SINEUP RNA can affect the RNA structure and that modifications shown to be inactive, or contents of modifications which are inactive share structural characteristics of unmodified IVT SINEUP RNA.

Studies on the thermal stability of the unmodified and the modified miniSINEUPs were also performed by means of CD since structural stability is a crucial parameter when designing RNA for potential therapeutic applications (FIG. 9E). The apparent melting temperature (Tm) was determined by following the variation of the CD intensity at 270 nm as a function of temperature (Ranjbar, B. et al. (2009) *Chem Biol Drug Des,* 74 (2): 101-20). In accordance with literature, we found that the two miniSINEUPs displaying a spectrum similar to B-form conformation of DNA showed improved stability compared to the unmodified RNA sequence and increased the Tm by approx. 15° C. (Nowakowski, J. et al. (1997) *Seminars in Virology,* 8 (3): 153-165). Of the remaining SINEUP versions, Am+m6A RNA sequences had an apparent Tm comparable to the unmodified one, while the RNA with m6A displayed a 5° C. Tm increment.

Example 8

This Example shows the comparison between the modifications seen in in-cell transcribed (mICT) SINEUP-GFP RNA with those of unmodified or modified IVT SINEUP-GFP RNA. This allows the identification of modifications which are naturally introduced into SINEUP RNA when transcribed in-cell, and which may be artificially introduced into IVT SINEUP RNA in order to mimic the naturally occurring mICT SINEUP RNA.

Modified IVT SINEUP-GFP was generated with a reaction mixture containing 20% pseudouridine-5'-triphosphate (ψ). 32 kmer modified regions were identified in the mICT SINEUP-GFP from the Nanocompore with IVT SINEUP-GFP (Table 1). ψ at position 64 (between BD and inverted SINEB2), 103 (inverted SINEB2), 199 (inverted SINEB2), 399 (downstream of Alu) and 426 (downstream of Alu) were identified at the mICT SINEUP-GFP from the Nanocompore with 20% ψ mIVT SINEUP-GFP (Table 2).

TABLE 1

Nanocompore kmer Peaks for mICT SINEUP-GFP compared to unmodified IVT SINEUP-GFP

| Compare | kmer_start_position | kmer | peak_value | GMM_logit_pvalue |
|---|---|---|---|---|
| 0% modified IVT SINEUP-GFP | 13 | CCGGU | 0 | 7.23E-34 |
| | 37 | GUUCA | 0 | 0.001741139 |
| | 54 | GCCAC | 67.2821612 | 5.22E-68 |
| | 62 | GCUGG | 0 | 0.003034442 |
| | 103 | UCAGA | 0 | 7.84E-13 |
| | 124 | CCCAG | 0 | 1.12E-31 |
| | 166 | CCACC | 0 | 9.18E-55 |
| | 169 | CCAUG | 0 | 2.93E-35 |
| | 190 | UCCAA | 0 | 0.001978081 |
| | 198 | CUGGU | 0 | 3.58E-28 |
| | 284 | ACAGC | 0 | 6.50E-10 |
| | 390 | CCCCA | 0 | 5.82E-49 |
| | 398 | CUCCC | 0 | 2.24E-75 |
| | 400 | CCCCA | 86.5505727 | 2.81E-87 |
| | 426 | UCCUA | 0 | 1.21E-68 |
| | 451 | CCAAU | 0 | 9.12E-47 |
| | 465 | CCAAG | 0 | 5.15E-69 |
| | 496 | CAGAC | 0 | 8.22E-62 |
| | 497 | AGACU | 0 | 5.99E-197 |
| | 539 | GGACA | 0 | 9.65E-27 |
| | 583 | AGACU | 0 | 1.26E-176 |
| | 591 | UUCCU | 0 | 3.65E-102 |
| | 600 | AAACU | 0 | 2.04E-109 |
| | 691 | AGACU | 304.843096 | 1.44E-305 |
| | 703 | CCAAC | 0 | 9.31E-81 |
| | 830 | CAGCC | 0 | 3.96E-155 |
| | 895 | AGACG | 0 | 4.22E-111 |
| | 969 | AGACU | 0 | 1.16E-125 |
| | 1148 | GCUUG | 0 | 1.44E-305 |
| | 1151 | UGUAU | 0 | 3.75E-102 |
| | 1156 | GCAAG | 0 | 8.22E-22 |
| | 1187 | AUCUU | 0 | 2.34E-192 |

TABLE 2

Nanocompore kmer Peaks for mICT SINEUP-GFP compared to 20% Ψ modified IVT SINEUP-GFP

| Compare | kmer_start_position | kmer | peak_value | GMM_logit_pvalue |
|---|---|---|---|---|
| 20% Ψ modified IVT SINEUP-GFP | 4 | UGGUG | 47.97771895 | 1.05E-48 |
| | 14 | CGGUA | 0 | 8.69E-35 |
| | 21 | GCUAG | 0 | 2.30E-22 |
| | 31 | CUGAC | 0 | 2.85E-18 |
| | 32 | UGACG | 0 | 8.27E-25 |
| | 33 | GACGG | 0 | 4.77E-13 |
| | 35 | CGGUU | 0 | 1.28E-19 |
| | 37 | GUUCA | 0 | 4.38E-25 |
| | 38 | UUCAC | 0 | 1.56E-17 |
| | 41 | ACUAG | 0 | 1.73E-19 |
| | 45 | GAUGC | 0 | 1.02E-06 |
| | 46 | AUGCG | 49.8122061 | 1.54E-50 |
| | 58 | CUGUG | 0 | 1.49E-37 |
| | 67 | AUAUC | 0 | 4.00E-25 |
| | 68 | UAUCU | 0 | 5.25E-38 |
| | 76 | GAAUU | 0 | 4.91E-21 |
| | 77 | AAUUC | 0 | 0.000652826 |
| | 78 | AUUCG | 0 | 1.25E-13 |
| | 84 | CCUUC | 0 | 1.46E-16 |
| | 85 | CUUCA | 0 | 1.52E-11 |
| | 91 | UGCUA | 0 | 5.05E-27 |
| | 92 | GCUAG | 0 | 2.03E-13 |
| | 114 | CAUUG | 0 | 1.52E-27 |
| | 124 | CCCAG | 39.61205817 | 2.44E-40 |
| | 127 | AGAAC | 0 | 1.83E-36 |
| | 135 | AGUUA | 0 | 4.52E-25 |
| | 136 | GUUAU | 0 | 3.42E-24 |
| | 139 | AUACG | 0 | 1.59E-17 |
| | 140 | UACGG | 0 | 1.81E-11 |
| | 141 | ACGGU | 0 | 9.36E-39 |
| | 142 | CGGUA | 0 | 1.12E-44 |
| | 153 | UGGUG | 0 | 4.13E-26 |
| | 156 | UGGUU | 0 | 2.43E-24 |
| | 164 | AACCA | 0 | 5.85E-74 |
| | 166 | CCACC | 0 | 1.66E-73 |
| | 169 | CCAUG | 82.45728653 | 3.49E-83 |
| | 170 | CAUGU | 0 | 8.44E-36 |
| | 187 | AGUUC | 0 | 0.001735908 |
| | 190 | UCCAA | 0 | 3.36E-05 |
| | 191 | CCAAA | 0 | 1.53E-38 |
| | 201 | GUCCU | 0 | 7.78E-12 |
| | 204 | CUGUG | 0 | 9.24E-46 |
| | 218 | CCAGU | 0 | 1.30E-59 |
| | 219 | CAGUG | 0 | 7.81E-50 |
| | 222 | UGCUC | 0 | 0.001230453 |
| | 249 | AGCUC | 0 | 4.74E-12 |
| | 282 | GAACA | 0 | 1.22E-48 |
| | 294 | AGCUG | 0 | 1.01E-07 |
| | 311 | CATAC | 0 | 8.89E-28 |
| | 312 | AUACU | 65.93600551 | 1.16E-66 |
| | 314 | ACUAU | 0 | 7.45E-18 |
| | 315 | CUAUA | 0 | 2.73E-59 |
| | 318 | UAAUU | 0 | 8.73E-35 |
| | 321 | UUCUA | 0 | 2.74E-71 |
| | 322 | UCUAG | 0 | 8.39E-48 |
| | 325 | AGUAC | 0 | 3.59E-28 |
| | 359 | ACUGG | 0 | 6.64E-25 |
| | 376 | GAAUC | 0 | 3.76E-44 |
| | 377 | AAUCU | 0 | 5.87E-42 |
| | 378 | AUCUG | 0 | 6.59E-76 |
| | 380 | CUGUU | 75.83085239 | 1.48E-76 |
| | 384 | UGUCA | 0 | 5.72E-53 |
| | 390 | CCCCA | 0 | 2.16E-49 |
| | 400 | CCCCA | 0 | 2.65E-83 |
| | 428 | CUAUA | 0 | 2.33E-109 |
| | 451 | CCAAU | 0 | 6.95E-42 |
| | 452 | CAAUA | 0 | 3.57E-41 |
| | 465 | CCAAG | 0 | 5.98E-48 |
| | 481 | UUUUC | 0 | 1.71E-108 |
| | 482 | UUUCU | 0 | 1.64E-64 |
| | 488 | UGCUU | 0 | 6.53E-61 |
| | 496 | CAGAC | 0 | 2.86E-48 |
| | 497 | AGACU | 172.3719902 | 4.25E-173 |
| | 500 | CUUUG | 0 | 4.73E-123 |

TABLE 2-continued

Nanocompore kmer Peaks for mICT SINEUP-GFP compared to 20% Ψ modified IVT SINEUP-GFP

| Compare | kmer_start_position | kmer | peak_value | GMM_logit_pvalue |
|---|---|---|---|---|
| | 502 | UUGUA | 0 | 1.59E-68 |
| | 505 | UAAUA | 0 | 4.52E-51 |
| | 518 | UGGAG | 0 | 8.50E-46 |
| | 522 | GUGCA | 0 | 9.21E-42 |
| | 530 | UAUUC | 0 | 4.71E-124 |
| | 539 | GGACA | 0 | 5.89E-22 |
| | 562 | CAGUU | 0 | 9.22E-72 |
| | 564 | GUUCU | 0 | 1.15E-39 |
| | 567 | CUUUC | 0 | 1.81E-66 |
| | 568 | UUUCU | 0 | 2.33E-133 |
| | 583 | AGACU | 0 | 5.00E-05 |
| | 584 | GACUA | 0 | 1.79E-64 |
| | 589 | UGUUC | 0 | 4.12E-83 |
| | 591 | UUCCU | 248.9895093 | 1.02E-249 |
| | 593 | CCUUA | 0 | 5.12E-190 |
| | 602 | ACUGG | 0 | 1.06E-90 |
| | 603 | CUGGU | 0 | 1.61E-120 |
| | 604 | UGGUG | 0 | 5.34E-108 |
| | 609 | UGUAU | 0 | 1.50E-112 |
| | 610 | GUAUU | 0 | 4.99E-106 |
| | 614 | UAUCU | 0 | 1.65E-197 |
| | 620 | UUAUG | 0 | 4.80E-97 |
| | 621 | UAUGC | 0 | 1.83E-47 |
| | 623 | UGCAA | 96.06505577 | 8.61E-97 |
| | 647 | CAGCC | 0 | 1.65E-67 |
| | 649 | GCCAC | 0 | 3.03E-89 |
| | 658 | GAUGG | 0 | 3.28E-72 |
| | 665 | CAGCA | 0 | 1.95E-97 |
| | 667 | GCAUG | 0 | 4.32E-198 |
| | 675 | GGAUG | 0 | 1.33E-79 |
| | 676 | GAUGG | 0 | 9.01E-53 |
| | 677 | AUGGU | 0 | 7.31E-62 |
| | 678 | UGGUA | 0 | 3.61E-101 |
| | 691 | AGACU | 305.2423846 | 5.72E-306 |
| | 703 | CCAAC | 0 | 6.65E-148 |
| | 707 | CUGUG | 0 | 3.96E-158 |
| | 718 | UGACU | 0 | 9.75E-40 |
| | 719 | GACUG | 0 | 1.49E-67 |
| | 720 | ACUGG | 0 | 7.76E-109 |
| | 724 | GCAUG | 0 | 7.64E-247 |
| | 725 | CAUGG | 0 | 1.22E-117 |
| | 732 | GGUUC | 0 | 6.37E-28 |
| | 734 | UUCAG | 0 | 8.05E-68 |
| | 743 | GAAUU | 0 | 5.24E-155 |
| | 751 | CUGUG | 0 | 1.22E-133 |
| | 758 | GAAAA | 0 | 6.20E-99 |
| | 759 | AAAAU | 0 | 6.66E-75 |
| | 763 | UGUUC | 0 | 2.72E-217 |
| | 764 | GUUCU | 0 | 1.25E-117 |
| | 802 | GGUCC | 0 | 2.01E-115 |
| | 830 | CAGCC | 305.2423846 | 5.72E-306 |
| | 833 | CCUCA | 0 | 2.45E-36 |
| | 855 | GGUCU | 0 | 1.54E-109 |
| | 856 | GUCUG | 0 | 1.24E-274 |
| | 857 | UCUGU | 0 | 1.78E-176 |
| | 863 | GAUGC | 0 | 6.90E-32 |
| | 879 | UGACC | 0 | 3.67E-157 |
| | 888 | UGCCA | 0 | 1.96E-186 |
| | 891 | CAAUA | 0 | 2.27E-135 |
| | 902 | CAAGA | 0 | 4.00E-124 |
| | 905 | GAAUG | 0 | 1.89E-165 |
| | 918 | AUCAU | 0 | 1.51E-138 |
| | 961 | CCCUG | 0 | 2.65E-70 |
| | 969 | AGACU | 0 | 4.74E-104 |
| | 972 | CUUCC | 196.1436202 | 7.18E-197 |
| | 975 | CCAUU | 0 | 1.28E-142 |
| | 978 | UUGAA | 0 | 1.40E-113 |
| | 990 | GUUCU | 0 | 2.79E-235 |
| | 995 | GAAUA | 0 | 1.38E-106 |
| | 998 | UAGAA | 0 | 1.02E-144 |
| | 1000 | GAAGA | 0 | 2.51E-63 |
| | 1003 | GAUGC | 0 | 4.53E-38 |
| | 1019 | CCCAC | 0 | 7.59E-229 |
| | 1022 | ACCAG | 0 | 0.002415308 |

TABLE 2-continued

Nanocompore kmer Peaks for mICT SINEUP-GFP compared to 20% Ψ modified IVT SINEUP-GFP

| Compare | kmer_start_ position | kmer | peak_value | GMM_logit_ pvalue |
|---|---|---|---|---|
| | 1023 | CCAGU | 0 | 3.11E-250 |
| | 1024 | CAGUG | 285.5929968 | 2.55E-286 |
| | 1031 | GAAUC | 0 | 1.05E-170 |
| | 1033 | AUCUG | 0 | 1.66E-42 |
| | 1048 | UAUAU | 0 | 1.99E-73 |
| | 1056 | CCUAU | 0 | 2.43E-186 |
| | 1057 | CUAUA | 0 | 2.15E-165 |
| | 1065 | CUCUG | 0 | 5.72E-306 |
| | 1103 | CCAUA | 0 | 8.68E-194 |
| | 1138 | AGUUC | 0 | 2.63E-133 |
| | 1139 | GUUCC | 0 | 3.42E-151 |
| | 1145 | UUUGC | 0 | 1.86E-190 |
| | 1147 | UGCUU | 0 | 3.72E-198 |
| | 1148 | GCUUG | 305.2423846 | 5.72E-306 |
| | 1151 | UGUAU | 0 | 4.66E-127 |
| | 1156 | GCAAG | 0 | 2.08E-25 |
| | 1166 | GCUCA | 0 | 2.81E-100 |
| | 1180 | GAAUU | 0 | 2.56E-203 |
| | 1182 | AUUUA | 0 | 1.41E-189 |
| | 1183 | UUUAA | 0 | 4.66E-156 |
| | 1184 | UUAAU | 0 | 1.83E-154 |
| | 1185 | UAAUC | 0 | 5.21E-90 |
| | 1187 | AUCUU | 305.2423846 | 5.72E-306 |

mICT miniSINEUP-DJ1 was analysed by RT-qPCR using the method described in Castellanos-Rubio et al. (2019) *Sci. Rep.,* 9 (4220) (doi.org/10.1038/s41598-019-40018-6) to quantify candidate m6A regions. This method utilises the diminished capacity of the Bstl enzyme to 5 retrotranscribe m6A residues and the m6A-induced reduction in Bstl retrotranscription efficiency can be assessed by quantitative PCR (qPCR). Four m6A putative sites were identified, m6A 46, m6A 63, m6A 81 and m6A 111 (FIG. 11A). Among these, m6A 46 and m6A 111 showed a statistically significant alteration of Bstl retrotranscription efficiency, indicating the presence of m6A modification in the sites (FIG. 11B, left panel) m6A 46 and/or the region surrounding m6A 111 (bases 109-111) were then mutated to uracil residues to prevent methylation at these sites in both miniSINEUP-DJ1 and miniSINEUP-GFP and their ability to upregulate the translation of DJ1 and GFP, respectively, were tested. FIGS. 11C and 11D show the fold-change in DJ1 protein expression and amount of SINEUP activity, respectively, of the mutated miniSINEUP-DJ1 relative to control or unmutated miniSINEUP-DJ1 (i.e. with A residues present at positions 46 and 109-111, referred to as "WT" throughout FIG. 11). FIGS. 11E and 11F show the fold-change in GFP protein expression and amount of SINEUP activity, respectively, of the mutated miniSINEUP-GFP relative to control or unmutated mini-SINEUP-GFP. Preventing methylation at position 46 or 111 of both miniSINEUP-DJ1 and miniSINEUP-GFP reduced the upregulation of DJ1 and GFP translation and reduced the SINEUP activity relative to the unmutated molecules (i.e. with methylation at positions 46 and 111). Mutation of both positions 46 and 111 of miniSINEUP-DJ1 had a greater effect on the SINEUP activity than either position alone (FIGS. 11C and 11D). However, position 111 of miniSINEUP-GFP appeared to have a greater effect on SINEUP activity than position 46 as preventing methylation at this position alone had the greatest effect on SINEUP activity (FIGS. 11E and 11F).

FIG. 11G shows the amount of methylated unmutated or mutated miniSINEUP-GFP immunoprecipitated by MeRIP in either control cells or cells in which the N6-adenosine-methyltransferase 70 kDa subunit METTL3 has been knocked-down by shRNA (shMETTL3). When positions 46 or 109-111 are mutated to prevent methylation the amount of methylated miniSINEUP-GFP immunoprecipitated by MeRIP is reduced and when both m6A 46 and positions 109-111 are mutated, methylation of miniSINEUP-GFP is completely abrogated.

This data therefore identifies multiple modifications in mICT SINEUP RNA and shows that these may be found throughout the SINEUP RNA molecule, in particular within the regulatory sequence (also referred to as "effector domain" and "ED"). They contribute to the activity of the SINEUP RNA molecule and may therefore be useful to mimic in IVT SINEUP molecules.

The invention claimed is:

1. A functional nucleic acid molecule comprising:

(a) at least one target determinant sequence comprising a sequence reverse complementary to a target mRNA sequence for which protein translation is to be enhanced; and (b) at least one regulatory sequence comprising a SINE B2 element or a functionally active fragment of a SINE B2 element, wherein the functional nucleic acid molecule comprises one or more chemical modifications, wherein the chemical base modification comprises N6-Methyladenosine and 2'-O-methyladenosine modifications, and wherein the amount of 2'-O-methyladenosine compared to N6-Methyladenosine is greater than 3:97.

* * * * *

SEQUENCE LISTING

```
<160> NUMBER OF SEQ ID NOS: 54

<210> SEQ ID NO 1
<211> LENGTH: 183
<212> TYPE: RNA
<213> ORGANISM: Mus musculus
<220> FEATURE:
<223> OTHER INFORMATION: Full length inverted SINE B2 transposable
      element derived from AS Uchl1

<400> SEQUENCE: 1

gggcagugcu agaggagguc agaagagggc auuggauccc ccagaacugg aguuauacgg      60

uaaccucgug gugguuguga accaccaugu ggauggauau ugaguuccaa acacuggucc     120

ugugcaagag cauccagugc ucuuaagugc ugagccaucu cuuuagcucc agucucuuaa     180

gcu                                                                   183


<210> SEQ ID NO 2
<211> LENGTH: 167
<212> TYPE: RNA
<213> ORGANISM: Mus musculus
<220> FEATURE:
<223> OTHER INFORMATION: 167nt inverted SINE B2 transposable element
```

derived from AS Uchl1

<400> SEQUENCE: 2
cagugcuaga ggaggucaga agagggcauu ggaucccca gaacuggagu uauacgguaa 60
ccucguggug guugugaacc accaugugga uggauauuga guuccaaaca cugguccugu 120
gcaagagcau ccagugcucu uaagugcuga gccaucucuu uagcucc 167

<210> SEQ ID NO 3
<211> LENGTH: 77
<212> TYPE: RNA
<213> ORGANISM: Mus musculus
<220> FEATURE:
<223> OTHER INFORMATION: nt 44-120 of inverted SINE B2 transposable element derived from AS Uchl1

<400> SEQUENCE: 3
gaacuggagu uauacgguaa ccucguggug guugugaacc accaugugga uggauauuga 60
guuccaaaca cugguccc 77

<210> SEQ ID NO 4
<211> LENGTH: 38
<212> TYPE: RNA
<213> ORGANISM: Mus musculus
<220> FEATURE:
<223> OTHER INFORMATION: nt 59-96 of inverted SINE B2 transposable element derived from AS Uchl1

<400> SEQUENCE: 4
gguaaccucg uggugguugu gaaccaccau guggaugg 38

<210> SEQ ID NO 5
<211> LENGTH: 29
<212> TYPE: RNA
<213> ORGANISM: Mus musculus
<220> FEATURE:
<223> OTHER INFORMATION: nt 64-92 of inverted SINE B2 transposable element derived from AS Uchl1

<400> SEQUENCE: 5
ccucguggug guugugaacc accaugugg 29

<210> SEQ ID NO 6
<211> LENGTH: 61
<212> TYPE: RNA
<213> ORGANISM: Mus musculus
<220> FEATURE:
<223> OTHER INFORMATION: nt 52-112 of inverted SINE B2 transposable element derived from AS Uchl1

<400> SEQUENCE: 6
guuauacggu aaccucgugg ugguugugaa ccaccaugug gauggauauu gaguuccaaa 60
c 61

<210> SEQ ID NO 7
<211> LENGTH: 98
<212> TYPE: RNA
<213> ORGANISM: Mus musculus
<220> FEATURE:
<223> OTHER INFORMATION: nt 36-133 of inverted SINE B2 transposable element derived from AS Uchl1

<400> SEQUENCE: 7
aucccccaga acuggaguua uacgguaacc ucgugguggu ugugaaccac cauguggaug 60
gauauugagu uccaaacacu gguccugugc aagagcau 98

<210> SEQ ID NO 8
<211> LENGTH: 129
<212> TYPE: RNA
<213> ORGANISM: Mus musculus
<220> FEATURE:
<223> OTHER INFORMATION: nt 22-150 of inverted SINE B2 transposable element derived from AS Uchl1

<400> SEQUENCE: 8
gaagagggca uuggaucccc cagaacugga guuauacggu aaccucgugg ugguugugaa 60
ccaccaugug gauggauauu gaguuccaaa cacugguccu gugcaagagc auccagugcu 120
cuuaagugc 129

<210> SEQ ID NO 9
<211> LENGTH: 67
<212> TYPE: RNA
<213> ORGANISM: Mus musculus
<220> FEATURE:
<223> OTHER INFORMATION: nt 44-110 of inverted SINE B2 transposable element derived from AS Uchl1

<400> SEQUENCE: 9
gaacuggagu uauacgguaa ccucguggug guugugaacc accaugugga uggauauuga 60
guuccaa 67

<210> SEQ ID NO 10
<211> LENGTH: 107
<212> TYPE: RNA
<213> ORGANISM: Mus musculus
<220> FEATURE:
<223> OTHER INFORMATION: nt 34-140 of inverted SINE B2 transposable element derived from AS Uchl1

<400> SEQUENCE: 10 ggaucccca gaacuggagu uauacgguaa ccucguggug guugugaacc accaugugga 60
uggauauuga guuccaaaca cugguccugu gcaagagcau ccagugc 107

<210> SEQ ID NO 11
<211> LENGTH: 127
<212> TYPE: RNA
<213> ORGANISM: Mus musculus
<220> FEATURE:
<223> OTHER INFORMATION: nt 24-150 of inverted SINE B2 transposable element derived from AS Uchl1

<400> SEQUENCE: 11
agagggcauu ggaucccca gaacuggagu uauacgguaa ccucguggug guugugaacc 60
accaugugga uggauauuga guuccaaaca cugguccugu gcaagagcau ccagugcucu 120
uaagugc 127

<210> SEQ ID NO 12
<211> LENGTH: 116
<212> TYPE: RNA
<213> ORGANISM: Mus musculus
<220> FEATURE:
<223> OTHER INFORMATION: nt 27-142 of inverted SINE B2 transposable element derived from AS Uchl1

<400> SEQUENCE: 12
gggcauugga uccccagaa cuggaguuau acgguaaccu cgugguggu gugaaccacc 60 auguggaugg auauugaguu ccaaacacug guccugugca agagcaucca gugcuc 116

<210> SEQ ID NO 13
<211> LENGTH: 206
<212> TYPE: RNA
<213> ORGANISM: Artificial sequence
<220> FEATURE:
<223> OTHER INFORMATION: SINEUP 071 and miniSINEUP 071 effector domain

<400> SEQUENCE: 13
uuauuuuaaa uauaugagua uuucaccugc auaggcgcac aguacccaca gagacuagaa 60
gaggguagua gauccccuag aacuggaguu auacgguaac cucgugugg uugugagcua 120 ccauguggau ggauacuggg aaucaaaccc agguccugug gaaggcaggc aggugcucuc 180
aagcacugag ccaucucuuc agcucc 206

<210> SEQ ID NO 14
<211> LENGTH: 206
<212> TYPE: RNA
<213> ORGANISM: Artificial sequence
<220> FEATURE:
<223> OTHER INFORMATION: SINEUP 072 and miniSINEUP 072 effector domain

<400> SEQUENCE: 14
uuauuuuaaa uauaugagua uuucaccugc auaggcgcac agugcucaag gagaucagaa 60
gagggcauca gaucuccuga gacuggaguu auacgguaac cucgugaugg uugugaacua 120
ccauguggau ggauauugag uuccaaacac agguccugug caagagcagc aggugcucuu 180
aagcacggaa ccaucucuuu agcucc 206

<210> SEQ ID NO 15
<211> LENGTH: 156
<212> TYPE: RNA
<213> ORGANISM: Artificial sequence
<220> FEATURE:
<223> OTHER INFORMATION: SINEUP 073 and miniSINEUP 073 effector domain

<400> SEQUENCE: 15
gaggcuagaa gaggguauca gauccccuga gacuggaguu auacgguaac cucguggugg 60
uugugagcca ccauguggau ggauacugag aaccaaaccc ugguccugug caagagcauc 120
aggugcucuu aagcacggaa ccaucucuuc agcucc 156

<210> SEQ ID NO 16
<211> LENGTH: 68
<212> TYPE: RNA
<213> ORGANISM: Artificial sequence
<220> FEATURE:
<223> OTHER INFORMATION: SINEUP 074 and miniSINEUP 074 effector domain

<400> SEQUENCE: 16
guccugugca agagcaucga acucggugcu cuuaagcaca gaagccacca agccaucucu 60
ucagcccc 68

<210> SEQ ID NO 17
<211> LENGTH: 110
<212> TYPE: RNA
<213> ORGANISM: Artificial sequence
<220> FEATURE:
<223> OTHER INFORMATION: SINEUP 075 and miniSINEUP 075 effector domain

<400> SEQUENCE: 17
cagugcuaga ggaggucaga agagggcauc ccccagccuc gugguguug ugaaccacca 60 uguggcugug caagagcaug cucuuaagug cugagccauc ucuuuagcuc 110

<210> SEQ ID NO 18
<211> LENGTH: 126
<212> TYPE: RNA
<213> ORGANISM: Artificial sequence
<220> FEATURE:
<223> OTHER INFORMATION: 24-150 effector domain

<400> SEQUENCE: 18
gagggcauug gaucccccag aacuggaguu auacgguaac cucguggugg uugugaacca 60
ccauguggau ggauauugag uuccaaacac ugguccugug caagagcauc cagugcucuu 120
aagugc 126

<210> SEQ ID NO 19
<211> LENGTH: 89
<212> TYPE: RNA
<213> ORGANISM: Artificial sequence
<220> FEATURE:
<223> OTHER INFORMATION: C_34-122 effector domain

<400> SEQUENCE: 19 ggaucccca gaacuggagu uauacgguaa ccucguggug guugugaacc accaugugga 60
uggauauuga guuccaaaca cugguccug 89

<210> SEQ ID NO 20
<211> LENGTH: 72
<212> TYPE: RNA
<213> ORGANISM: Artificial sequence
<220> FEATURE:
<223> OTHER INFORMATION: TM effector domain

<400> SEQUENCE: 20
ugcuagagga ggucagaaga gggcauugga ugcaaaucca gugcucuuaa gugcugagcc 60
aucucuuuag cu 72

<210> SEQ ID NO 21
<211> LENGTH: 94
<212> TYPE: RNA
<213> ORGANISM: Artificial sequence
<220> FEATURE:
<223> OTHER INFORMATION: MC2 effector domain

<400> SEQUENCE: 21
gagggcauug gaucccccag aacuggaguu auacgguaac gauggauauu gaguuccaaa 60
cacugguccu gugcaagagc auccagugcu cuua 94

<210> SEQ ID NO 22
<211> LENGTH: 180
<212> TYPE: RNA
<213> ORGANISM: Artificial sequence
<220> FEATURE:
<223> OTHER INFORMATION: G60A mutant of inverted SINE B2 transposable
element derived from AS Uchl1

<400> SEQUENCE: 22
cagugcuaga ggaggucaga agagggcauu ggaucccca gaacuggagu uauacgauaa 60
ccucguggug guugugaacc accaugugga uggauauuga guuccaaaca cugguccugu 120
gcaagagcau ccagugcucu uaagugcuga gccaucucuu uagcuccagu cucuuaagcu 180

<210> SEQ ID NO 23
<211> LENGTH: 180
<212> TYPE: RNA
<213> ORGANISM: Artificial sequence
<220> FEATURE:
<223> OTHER INFORMATION: G60C mutant of inverted SINE B2 transposable element derived from AS Uchl1

<400> SEQUENCE: 23
cagugcuaga ggaggucaga agagggcauu ggaucccccca gaacuggagu uauacgcuaa 60
ccucguggug guugugaacc accaugugga uggauauuga guuccaaaca cugguccugu 120
gcaagagcau ccagugcucu uaagugcuga gccaucucuu uagcuccagu cucuuaagcu 180

<210> SEQ ID NO 24
<211> LENGTH: 180
<212> TYPE: RNA
<213> ORGANISM: Artificial sequence
<220> FEATURE:
<223> OTHER INFORMATION: A51C mutant of inverted SINE B2 transposable element derived from AS Uchl1

<400> SEQUENCE: 24
cagugcuaga ggaggucaga agagggcauu ggaucccccca gaacuggcgu uauacgguaa 60
ccucguggug guugugaacc accaugugga uggauauuga guuccaaaca cugguccugu 120
gcaagagcau ccagugcucu uaagugcuga gccaucucuu uagcuccagu cucuuaagcu 180

<210> SEQ ID NO 25
<211> LENGTH: 180
<212> TYPE: RNA
<213> ORGANISM: Artificial sequence
<220> FEATURE:
<223> OTHER INFORMATION: C47G and G117C mutant of inverted SINE B2 transposable element derived from AS Uchl1

<400> SEQUENCE: 25
cagugcuaga ggaggucaga agagggcauu ggaucccccca gaaguggagu uauacgguaa 60
ccucguggug guugugaacc accaugugga uggauauuga guuccaaaca cugcuccugu 120
gcaagagcau ccagugcucu uaagugcuga gccaucucuu uagcuccagu cucuuaagcu 180

<210> SEQ ID NO 26
<211> LENGTH: 180
<212> TYPE: RNA
<213> ORGANISM: Artificial sequence
<220> FEATURE:
<223> OTHER INFORMATION: 46-49/115-118 stem swap mutant of inverted SINE B2 transposable element derived from AS Uchl1

<400> SEQUENCE: 26
cagugcuaga ggaggucaga agagggcauu ggaucccccca gauggugagu uauacgguaa 60
ccucguggug guugugaacc accaugugga uggauauuga guuccaaaca cgucaccugu 120
gcaagagcau ccagugcucu uaagugcuga gccaucucuu uagcuccagu cucuuaagcu 180

<210> SEQ ID NO 27
<211> LENGTH: 180
<212> TYPE: RNA
<213> ORGANISM: Artificial sequence
<220> FEATURE:
<223> OTHER INFORMATION: 50-53 and 112-114 base swap mutant of inverted SINE B2 transposable element derived from AS Uchl1

<400> SEQUENCE: 27
cagugcuaga ggaggucaga agagggcauu ggaucccccca gaacugcacu auacgguaac 60
cucguggugg uugugaacca ccauguggau ggauauugag uuccaaauga gugguccugu 120
gcaagagcau ccagugcucu uaagugcuga gccaucucuu uagcuccagu cucuuaagcu 180

<210> SEQ ID NO 28
<211> LENGTH: 77
<212> TYPE: RNA
<213> ORGANISM: Artificial sequence
<220> FEATURE:
<223> OTHER INFORMATION: nt 44-120 A45G mutant of inverted SINE B2
transposable element derived from AS Uchl1

<400> SEQUENCE: 28
ggacuggagu uauacgguaa ccucguggug guugugaacc accaugugga uggauauuga 60
guuccaaaca cugguce 77

<210> SEQ ID NO 29
<211> LENGTH: 77
<212> TYPE: RNA
<213> ORGANISM: Artificial sequence
<220> FEATURE:
<223> OTHER INFORMATION: nt 44-120 A51C mutant of inverted sine B2
transposable element derived from AS Uchl1

<400> SEQUENCE: 29
gaacuggcgu uauacgguaa ccucguggug guugugaacc accaugugga uggauauuga 60
guuccaaaca cugguce 77

<210> SEQ ID NO 30
<211> LENGTH: 77
<212> TYPE: RNA
<213> ORGANISM: Artificial sequence
<220> FEATURE:
<223> OTHER INFORMATION: 44-120 U78G SINEUP

<400> SEQUENCE: 30
gaacuggagu uauacgguaa ccucguggug guugggaacc accaugugga uggauauuga 60
guuccaaaca cugguce 77

<210> SEQ ID NO 31
<211> LENGTH: 77
<212> TYPE: RNA
<213> ORGANISM: Artificial sequence
<220> FEATURE:
<223> OTHER INFORMATION: 44-120 GUG77-79CCC SINEUP

<400> SEQUENCE: 31
gaacuggagu uauacgguaa ccucguggug guucccaacc accaugugga uggauauuga 60
guuccaaaca cugguce 77

<210> SEQ ID NO 32
<211> LENGTH: 77
<212> TYPE: RNA
<213> ORGANISM: Artificial sequence
<220> FEATURE:
<223> OTHER INFORMATION: 44-120 SINEUP strong

<400> SEQUENCE: 32
ggaccggagu uauacgguaa ccgcguggug guugugaacc accacgcgga uggauauuga 60
guuccaaaca ccggucc 77

<210> SEQ ID NO 33

<211> LENGTH: 77
<212> TYPE: RNA
<213> ORGANISM: Artificial sequence
<220> FEATURE:
<223> OTHER INFORMATION: 44-120 SINEUP weak

<400> SEQUENCE: 33
gaacuagagu uauacgguaa ccacauggug guugugaacc accaugugga uggauauuga 60
guuccaaaca cuaguuc 77

<210> SEQ ID NO 34
<211> LENGTH: 228
<212> TYPE: RNA
<213> ORGANISM: Mus musculus
<220> FEATURE:
<223> OTHER INFORMATION: SINEB2/B3 consensus sequence from RepBase

<400> SEQUENCE: 34
uuuuuuuaaa aauuuauuuu uauuuuaugu guaugagugu uuugccugca uguaugucug 60
uguaccacgu gcgugccugg ugcccgcgga ggccagaaga gggcgucgga uccccuggaa 120
cuggaguuac agaugguugu gagccgccau gugggugcug ggaaucgaac ccgggucc uc 180 uggaagagca gccagugcuc uuaaccgcug agccaucucu ccagcccc 228

<210> SEQ ID NO 35
<211> LENGTH: 107
<212> TYPE: RNA
<213> ORGANISM: Mus musculus
<220> FEATURE:
<223> OTHER INFORMATION: AS Txnip SINEB2

<400> SEQUENCE: 35
gaugccuuag aaguggaguu aagaguugug agcugccguu uuuugguucu gggacucgaa 60
cucguuuccu cugauacuau caaccaccaa gccaucucuu cagcccc 107

<210> SEQ ID NO 36
<211> LENGTH: 131
<212> TYPE: RNA
<213> ORGANISM: Mus musculus
<220> FEATURE:
<223> OTHER INFORMATION: AS Uxt SINEB2 a

<400> SEQUENCE: 36
gccagaagaa guugugggau ucccuggaac uggagcaacc aacaguuugu gugcaccaug 60
uggguaaugg gaaucgaacc ugggucc ucu auaagacugg ccagugcucu uaacuacuga 120
ggugcauuuc u 131

<210> SEQ ID NO 37
<211> LENGTH: 187
<212> TYPE: RNA
<213> ORGANISM: Mus musculus
<220> FEATURE:
<223> OTHER INFORMATION: AS Uxt SINEB2 b

<400> SEQUENCE: 37
uuauuuuaaa uauaugagua uuucaccugc auaggcgcac aguacccaca gagacuagaa 60
gaggguggca gaucuccuga gacuggaguu aaugcuugug agcugccaug uggaugcugg 120
aaaucaaacc cagguccuuu ggaaggcagg caggugcucu uaaucaugga agcaucucuu 180
cagcucc 187

<210> SEQ ID NO 38
<211> LENGTH: 131
<212> TYPE: RNA
<213> ORGANISM: Mus musculus
<220> FEATURE:
<223> OTHER INFORMATION: AS Gadd45alpha SINEB2 a

<400> SEQUENCE: 38
cagcgacauc agaagaggau auuggauccc auuacagaug guugaaggcc accaugucgu 60
ugcugggaau gaacucaaga ccucuggaag agcagucagu gcucuuaacc ucugagccau 120
cucuccagcc c 131

<210> SEQ ID NO 39
<211> LENGTH: 114
<212> TYPE: RNA
<213> ORGANISM: Mus musculus
<220> FEATURE:
<223> OTHER INFORMATION: AS Gadd45alpha SINEB2 b

<400> SEQUENCE: 39
auccccucca aagcucaaga ugguuguaag ccacccugug auugcuggga uuugaacuca 60
agaccuccgg aagagcaauu agugcucuua accgcugagc aaucucucca gccc 114

<210> SEQ ID NO 40
<211> LENGTH: 214
<212> TYPE: RNA
<213> ORGANISM: Mus musculus
<220> FEATURE:
<223> OTHER INFORMATION: AS Nars2 SINEB2/B3

<400> SEQUENCE: 40
uuuuuuuuac uuguauaggu guuuugccug cauguguauc uaucuaugua ccgaauaugu 60
uccugguauc cacagagacc aaaaguggau guuguaucuc cugaaauugg agucauagac 120
aguuaugagc ugccauuuga gugcuuggaa uagaacccag guccucuuaa agagcaucca 180
gugcucuuaa aaacugagac aucucuguag ccuc 214

<210> SEQ ID NO 41
<211> LENGTH: 200
<212> TYPE: RNA
<213> ORGANISM: Mus musculus
<220> FEATURE:
<223> OTHER INFORMATION: AS Abhd11 SINEB2/B3

<400> SEQUENCE: 41
uuuauuuugc uuuaugugue ugaguguuug cuugaaugua ugucugugua ccacgccugu 60
accuugugcc uucagaguug agaggagggc auaggaucuc cuggaacugg aauugcaggu 120
gguugugagc cacccugugg guccugggga ccauacucca gcaagaacau caugugcucu 180
uaauuccuga gucuccaacc 200

<210> SEQ ID NO 42
<211> LENGTH: 214
<212> TYPE: RNA
<213> ORGANISM: Mus musculus
<220> FEATURE:
<223> OTHER INFORMATION: AS Ebp4.9 SINEB2/B3

<400> SEQUENCE: 42
uuuauuuacu uaucuuuaug uguaugagug uguugucaga cuguuauguc ugugugucac 60
augcaugccu gcuguucaug gaguccagaa gagggcaucg gauccccugg aacuggaguu 120
acagaugagu ggccauguga auguuaagaa ccaaaccugg guccucugaa agagcagaca 180
augcucuuaa cuacugagcu gucucuccag cccc 214

<210> SEQ ID NO 43
<211> LENGTH: 205
<212> TYPE: RNA
<213> ORGANISM: Mus musculus
<220> FEATURE:
<223> OTHER INFORMATION: AS Wfdc5 SINEB2/B3

<400> SEQUENCE: 43
uuauuuuauu cguguaagug uuuugccagc aucuaugucu ucgcacuaug ugcaggucug 60
gugccugagg gguccagacg agagcacugg gucuccggga acuggaguua cagaucauug 120
ugagccacca ugugggugca gggaaucgaa ccugggaccu cuggaggagc agccacugcu 180
cuuaaccacu acacuauuuc uccag 205

<210> SEQ ID NO 44
<211> LENGTH: 121
<212> TYPE: RNA
<213> ORGANISM: Mus musculus
<220> FEATURE:
<223> OTHER INFORMATION: AS Pgbd1 SINEB2/B3

<400> SEQUENCE: 44
ucuguggacc acuguguaca gaagccugag aaggcuagca gauccccaga acuggaacug 60
ugagacgcug ugcuauggag gugcuaggaa cugaaaaugg augggguccuc ugcaagagca 120 g 121

<210> SEQ ID NO 45
<211> LENGTH: 191
<212> TYPE: RNA
<213> ORGANISM: Mus musculus
<220> FEATURE:
<223> OTHER INFORMATION: AS Gsk3b SINEB2/B3

<400> SEQUENCE: 45
uuguuuuaau ugaauggcua uagggguguuu cuucuguaug uauaucuaug uuugguaccu 60
acagaggcau cagauccucu ggaacuguag uugcugacag uugugagcug ucauggggau 120
gcuggaauug aaccuggauc cuaugaaaga acagccagug uucuuaaccg cugagcuauc 180
ucuccaggcc c 191

<210> SEQ ID NO 46
<211> LENGTH: 205
<212> TYPE: RNA
<213> ORGANISM: Mus musculus
<220> FEATURE:
<223> OTHER INFORMATION: AS Rhod SINEB2_Mm2

<400> SEQUENCE: 46
uuuuuuuuuu aauuuuaaaa aaaaagauuu uauuuauuua uuuuauauau gaugaguaca 60
cugucacucu uuucagacac ccuagaaaag gggggcauca gaucccauua cagaugguug 120
ugagccacau gguugcuggg aauugaccuc aggaccucug aaagagcagu cagugcucuc 180
aaccuuugag ucaucucucc agccc 205

<210> SEQ ID NO 47
<211> LENGTH: 190
<212> TYPE: RNA
<213> ORGANISM: Mus musculus
<220> FEATURE:
<223> OTHER INFORMATION: AS Rhod SINEB2/B3A

<400> SEQUENCE: 47
auguauaucu guaaugggac auacucacau acaugggcac gugaguauaa aaggccagaa 60
gagagcacug gacccucugg aguugagauu cuaagcaguu gugaaccauc ugauguaggu 120
gcugggaacu gaacuugggu ccuuugcuag agaaguaugu cucuuaacca cugagccgua 180
ucuccauccc 190

<210> SEQ ID NO 48
<211> LENGTH: 169
<212> TYPE: RNA
<213> ORGANISM: Mus musculus
<220> FEATURE:
<223> OTHER INFORMATION: AS E4f1 SINEB2_Mm2

<400> SEQUENCE: 48
uaaagauuua uucauuaagu acacuguagc uaucuucaga cgcaucagaa gagggcguca 60
gaucucuuua cagguguug ugagccacca ugugguugcu ggaauuugaa cucaggaccu 120
ucaaaagagc agucaguguu cuuaaccgcu gagccaucuc uccaacccc 169

<210> SEQ ID NO 49
<211> LENGTH: 159
<212> TYPE: RNA
<213> ORGANISM: Mus musculus
<220> FEATURE:
<223> OTHER INFORMATION: AS E4f1 SINEB2_Mm1t

<400> SEQUENCE: 49
uuauuuauua uaaguacacu guagcugucu ucagacacaa caaaagaggg cgucagaucu 60
cauuacaggu gguugagcca ccaugugguu gcugggauuu gaacucagga ccuucagaac 120
agucagugcu cuuacccacu gagccagcga gccagcccc 159

<210> SEQ ID NO 50
<211> LENGTH: 13
<212> TYPE: RNA
<213> ORGANISM: Artificial sequence
<220> FEATURE:
<223> OTHER INFORMATION: Linker sequence

<400> SEQUENCE: 50
aucugcagaa uuc 13

<210> SEQ ID NO 51
<211> LENGTH: 35
<212> TYPE: DNA
<213> ORGANISM: Homo sapiens
<220> FEATURE:
<223> OTHER INFORMATION: Human Sox9

<400> SEQUENCE: 51
cggccaccag ccccctgccc cgggcccgcg tatga 35

<210> SEQ ID NO 52
<211> LENGTH: 35
<212> TYPE: DNA
<213> ORGANISM: Mus musculus
<220> FEATURE:
<223> OTHER INFORMATION: Mouse Sox9

<400> SEQUENCE: 52

-continued

```
cggccacccg ccccctgccc cgggctcgcg tatga                            35


<210> SEQ ID NO 53
<211> LENGTH: 35
<212> TYPE: DNA
<213> ORGANISM: Artificial sequence
<220> FEATURE:
<223> OTHER INFORMATION: miniSINEUP-Sox9

<400> SEQUENCE: 53

gccggtgggc gggggacggg gcccgagcgc atact                            35


<210> SEQ ID NO 54
<211> LENGTH: 255
<212> TYPE: DNA
<213> ORGANISM: Artificial sequence
<220> FEATURE:
<223> OTHER INFORMATION: miniSINEUP-Sox9

<400> SEQUENCE: 54

ctcgagtcat acgcgagccc ggggcagggg gcgggtggcc ggatgcggcc gccactgtgc    60

tggaattcca gtgctagagg aggtcagaag agggcattgg atcccccaga actggagtta   120

tacggtaacc tcgtggtggt tgtgaaccac catgtggatg gatattgagt tccaaacact   180

ggtcctgtgc aagagcatcc agtgctctta agtgctgagc catctcttta gctccagtct   240

cttaagcttt ctaga                                                    255
```